(12) United States Patent
Rubin et al.

(10) Patent No.: US 6,777,177 B1
(45) Date of Patent: *Aug. 17, 2004

(54) MAMMALIAN GENES INVOLVED IN VIRAL INFECTION AND TUMOR SUPPRESSION

(75) Inventors: Donald H. Rubin, Nashville, TN (US); Edward L. Organ, Nashville, TN (US); Raymond N. Dubois, Franklin, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/509,712

(22) PCT Filed: Oct. 8, 1998

(86) PCT No.: PCT/US98/21276

§ 371 (c)(1), (2), (4) Date: Mar. 31, 2000

(87) PCT Pub. No.: WO99/19481

PCT Pub. Date: Apr. 22, 1999

Related U.S. Application Data

(60) Provisional application No. 60/062,021, filed on Oct. 10, 1997.

(51) Int. Cl.[7] ............................. C12Q 1/70; C12Q 1/68; C12Q 1/18; I12N 5/00; I12N 5/02
(52) U.S. Cl. ............................. 435/5; 435/6; 435/7.2; 435/32; 435/325
(58) Field of Search ........................... 435/5, 6, 72, 32, 435/325

(56) References Cited

U.S. PATENT DOCUMENTS

| | | |
|---|---|---|
| 5,364,783 A | 11/1994 | Ruley |
| 5,627,058 A | 5/1997 | Ruley et al. |
| 6,448,000 B1 * | 9/2002 | Rubin et al. ............... 435/6 |

FOREIGN PATENT DOCUMENTS

| | | |
|---|---|---|
| WO | WO 90/09192 | 8/1990 |
| WO | WO 93/09230 | 5/1993 |
| WO | WO 97/39119 | 10/1997 |

OTHER PUBLICATIONS sequence alignment in SEQ ID No.: 75 with SEQ ID No.: 1 of Morris et al. (US 6,027,915) of 2A5–3 lambda CHO sequence file on Jan. 11, 1996 in application No.: 08/785150. Database Issued_Patents_NA.* sequence alignment of SEQ ID No.: 75 with SEQ ID No.: 27 of Dubois et al. (WO 99/19481). Jul. 24, 1999. Identification No.: AAX57445. Database: N_Geneseq_1101.*

Evans et al. "Gene Trapping and Functional Genomics" TIG, 13(9):370–374, Sep., 1997.

Organ et al. "U3 Gene–Trap Retrovirus Selection of Cellular Mutants Resistant to Lytic Reovirus Infection" J. Invest. Med., 44(3):320A, Annual Meeting of the Association of American Physicians, May 3–6, 1996.

Watson, JD, M Gilman, J Witkowski and M Zoller 1992 "The Isolation of Cloned Genes", in Recombinant DNA, 2$^{nd}$ Ed., WH Freeman &Co., New York.

Dermody, TS, ML Nibert, JD Wetzel, X Tong and BN Fields 1993 Cells and Viruses with Mutations Affecting Viral Entry Are Selected during Persistent Infections of L Cells with Mammalian Reoviruses. J Virol 67:2055–2063.

Skarnes, W.C. "The Identification of New Genes: Gene Trapping in Transgenic Mice" Current Opinion in Biotechnology 4:684–689, Jan. 1, 1993.

Pérez, L and L Carrasco 1994 Involvement of the vacuolar H$^+$–ATPase in animal virus entry. J Gen Virol 75:2595–2606.

Wright, JF, A Kurosky, and S Wasi 1994 An endothelial cell–surface form of annexin II binds human cytomegalovirus. Biochem. Biophys. Res. Comm. 198:983–989.

Brunetti, CR, RL Burke, S Kornfeld, W Gregory, FR Masiarz, KS Dingwell, and DC Johnson 1994 Herpes simplex virus glycoprotein D acquires mannose 6–phosphate residues and binds to mannose 6–phosphate receptors. J Biol Chem 269:17067–17074.

Wright, JF, A Kurosky, ELG Pryzdial, and S Wasi 1995 Host cellular annexin II is associated with cytomegalovirus particles isolated from cultured human fibroblasts J. Virol 69:4784–4791.

Brunetti, CR, RL Burke, B Hoflack, T Ludwig, KS Dingwell, and DC Johnson 1995 Role of mannose–6–phosphate receptors in herpes simplex virus entry into cells and cell–to–cell transmission. J Virol 69: 3517–3528.

* cited by examiner

*Primary Examiner*—James Housel
*Assistant Examiner*—Shanon Foley
(74) *Attorney, Agent, or Firm*—Needle & Rosenberg, PC

(57) ABSTRACT

The present invention provides methods of identifying cellular genes necessary for viral growth and cellular genes that function as tumor suppressors. Thus, the present invention provides nucleic acids related to and methods of reducing or preventing viral infection or cancer. The invention also provides methods of producing substantially virus-free cell cultures and methods for screening for additional such genes.

13 Claims, No Drawings

SEQUENCE LISTING

<160> NUMBER OF SEQ ID NOS: 127

<210> SEQ ID NO 1
<211> LENGTH: 925
<212> TYPE: DNA
<213> ORGANISM: Rattus norvegicus
<220> FEATURE:
<221> NAME/KEY: misc_feature
<222> LOCATION: 1- 925
<223> OTHER INFORMATION: n = g, a, c or t(u)

<400> SEQUENCE: 1 ggggaaaac cnggnaattg tttttttgacg anccaaaaag gggncnagna gcnnttntcc    60

-continued

| | |
|---|---|
| tanatggggn cgggatcntn tccnaggana gattnatgga gtatnccttt tttgcncnaa | 120 |
| ggttgattgc tcttgaaagg ntttgaggtg naattcctcc gtnagtttga ccgtagtcgg | 180 |
| atntgaagag ggattgttna gcagncataa tttcattccc tgnacaccca gtaacnnttt | 240 |
| accgtcattt ggttgggaat tgatntcggg aggtancaan ggccacagtt atttattgtt | 300 |
| ncggaggatt gcaccaattn ggccggctgc ctctganatc tgtttctcat ccatgccggt | 360 |
| tcacccagac gaaagccgaa agcntcggga gtcctaactn tagtccntga aagtcattcc | 420 |
| cagctgcgta attgggctgt gcagagtccc agctcggtaa atatttgccc cgtgactgag | 480 |
| ctggagagaa tgctcctttc ttggtcctgg gcagctcttg gcagctcaca tgcactgttt | 540 |
| acctatcctc ccacattccc ccctgaggaa tcatcgtgcc tcggttccct taagtcctct | 600 |
| caacagaaaa caaggcagag tggaacgaag gaaagtgcgt ggccgttaga aagcctgtct | 660 |
| cgaatctgtc ccacgtgcct caggtagcgt tccaaacagc aaagattcta gtgaagaaaa | 720 |
| ataccgtccg gtcaattagt caggtggaca gagcaggacc cggtgtcttg gaagcctcgt | 780 |
| ccattcctct ggggaaggtg ggggggggcg tgtaatgcag ctctcaagaa gaaggtattt | 840 |
| ttgttttcct ggagaaactg ccatcccagg agctgagagt ggatcagtag gaaggcctgt | 900 |
| gacaggaagc agggaggttc agcng | 925 |

<210> SEQ ID NO 2
<211> LENGTH: 554
<212> TYPE: DNA
<213> ORGANISM: Rattus norvegicus
<220> FEATURE:
<221> NAME/KEY: misc_feature
<222> LOCATION: 1- 554
<223> OTHER INFORMATION: n = g, a, c or t(u)

<400> SEQUENCE: 2

| | |
|---|---|
| caagatngan ggggcggcgg ttcgnccaga gagcgggtag ggaagggaac gcgccggatg | 60 |
| agccnggggtg cgganagcca gaccccaggc gtgggaaggg gagagagata gagcggccgg | 120 |
| ttgggaagag gaggaccgtg gttnataaat aacagaaagc ccagagggac gtanccatcc | 180 |
| gggatggaga gaggtaggga atccagntgt aagtcccaaa ctgccaccac cttcatnaga | 240 |
| actgcttcgt gtaaggtcac gcaccgggcc agctgtccng agtggcggtc ctggcgtgtt | 300 |
| aagttagcta aagtnactgc aactccgnct gtgcagactg ntcgtaaatt ctctctgtcc | 360 |
| gccaaattct ccctcctatt aaacttttca cttcctttca cttagtttcc tnacttcttt | 420 |
| caaacggaag ctgtaactga gcctgccacc cnganacntt gtggttgcca tttttatgct | 480 |
| aaagtaatcg tgtttttat gcctgtcaac tccctttttca tntaaagcag ggcntaccct | 540 |
| attataactc tgcc | 554 |

<210> SEQ ID NO 3
<211> LENGTH: 891
<212> TYPE: DNA
<213> ORGANISM: Rattus norvegicus
<220> FEATURE:
<221> NAME/KEY: misc_feature
<222> LOCATION: 1- 878
<223> OTHER INFORMATION: n = g, a, c or t(u)

<400> SEQUENCE: 3

| | |
|---|---|
| ttngaaanaa tttccgtnaa ggtcngnaat nggccccgga aaaatgngt tcctcccac | 60 |
| cttcattggn gcggatcctg ccngggaggc caatggttta acaaataatc tttnggagnt | 120 |
| ntggtngggg gggagggac ncccacagan tcatgnggtg gttngggngg nggcatcgt | 180 |

-continued

| | |
|---|---|
| tnngatatta tcacattntg ngaanctatg tngggcttc ctttcngaca ggtggtggtt | 240 |
| nnacangngg atgtgtgctt cttttttcag cagtggtgga cccggattct aagacccta | 300 |
| cngtaacaat gccctnttt cctaagccta accagtcctt tangaggant gctcttgggn | 360 |
| acccatgctg nntcacctag ccttggntca catnttnnac acaggaaaag gcagcatgtc | 420 |
| ttntnggagc tcagcttatt cccttcccnt cccatccagn atctccctgg gntggatgag | 480 |
| gtggatgacg catcttcaaa gcaccccacg tntcatggga tgtgcacagg agcttcgttg | 540 |
| gaaatgtgtt gcgcgaccag gcttgtgtag gaaacaacag actactcgaa attaaagtcn | 600 |
| taccttgcag ggttctcaga ggcttttacg cattaataaa catttgaatc ntaagaaggg | 660 |
| agcacagcat gtaatattnt tcaaattatc aggcnttgca accttcatta gtttctctta | 720 |
| cgcagctggg ngtggtggtg tgtacccttta atctcagcac tgaggaggca cngatatctc | 780 |
| catctctgtg acttccagac cggcntcgcc agagcaagtt ccaggccacc cagatgagat | 840 |
| gctcacagag gggaccttt tntgatgacc aacgnagnat gcaagtaagg a | 891 |

<210> SEQ ID NO 4
<211> LENGTH: 974
<212> TYPE: DNA
<213> ORGANISM: Rattus norvegicus
<220> FEATURE:
<221> NAME/KEY: misc_feature
<222> LOCATION: 1- 974
<223> OTHER INFORMATION: n = g, a, c or t(u)

<400> SEQUENCE: 4

| | |
|---|---|
| aaaanaanat attccgnntc tnntagcnna gaagttntnc gagcnntccc ccgtntttt | 60 |
| aaaaacccnc ggattccggn nntcgggntt taanngnttt tttaaggcc cnaagncccn | 120 |
| nttattgccg ncntttcccc cccgctnttg cncccctta cttngagant ngtgntncna | 180 |
| agatttnaag gttnttgccc ccccggcttt tnttcccctn nttttccccn nagnttaaaa | 240 |
| accggtntgg gttncnantt nnttgnancc nccnattggg gtttccgntt accngggtt | 300 |
| ttccccatgn ccgttccctc caatnttgna cttcccnggt cngggtccna atnccnngna | 360 |
| acngntcnan ccttattgac aattaatttt tccttgngna ntctgncccc cngnantttg | 420 |
| gggttcttgg gngcagggcc ttttttttcnt tggnngcaan ncataaatn ttaccagntt | 480 |
| gattgctaag gaagtancca tggttgngaa cccccccttn ttntctccca gatggaaccc | 540 |
| aggatttgg aactgcagag gcttcagggt cttgggaagc ggaggcagnn aaagattgga | 600 |
| gtgcactgtc cttttgcaat atggggtttg cctgcctgct ggctcntctc ctgctntntc | 660 |
| agatggtgac tgaggctact tcngcaggac tnggaataat catgtccagg tggctgccct | 720 |
| tccgagcaga aagggacaga cgtggggcga tgaagttgct atcgtttntt ttttttctg | 780 |
| cacagactgc aaagtgtgca gagggaggga ggctgtgcaa aaaaaaaaaa aaaaaaaa | 840 |
| aaaaaaaaaa ccgaggacgc agaagttaga ctgctgaccc atttggtgca tgtgtgccca | 900 |
| tggaggggg ggacctntt taagggttc acgcggcacg cantgggnaa nngnnctnt | 960 |
| acgnnctcc caga | 974 |

<210> SEQ ID NO 5
<211> LENGTH: 850
<212> TYPE: DNA
<213> ORGANISM: Rattus norvegicus
<220> FEATURE:
<221> NAME/KEY: misc_feature
<222> LOCATION: 1- 850

<223> OTHER INFORMATION: n = g, a, c or t(u)

<400> SEQUENCE: 5

| | | | | | |
|---|---|---|---|---|---|
| antttccct | caagnaaant | ntggtttggg | caacttgaag | acgcttnnac | cnaaaccct | 60 |
| tgnggagntt | ggngacctn | ttaccgnaan | gagtgggaaa | cgttttcctc | cgggttnang | 120 |
| gttaggggga | cccgnnggaa | aattttaaaa | ccnngnnggc | ttttttcgaat | taagggaaa | 180 |
| ngcggttng | gtnnntgaag | ggcgggnggt | tggagtcnna | gtccagagtt | gatttccacc | 240 |
| cacaaatntg | ggaggtgncg | gggaatgntg | ncnttttctt | gngatgaggg | ntgccgtncc | 300 |
| ggantaacag | ngnttgcntt | gtntngcaa | acgaagagtn | tcctgnttgg | aataggngtt | 360 |
| cngttcgang | ganccagatt | tangngntgg | agnaaggatt | nggcagataa | angcntgaga | 420 |
| natgnancnt | ggancaggtc | nggncnnagn | ntacagatga | tgnncccana | canganataa | 480 |
| ntncagatca | cagtcgtacc | cgnggctggg | ccatgaanag | ggcatcccca | gacnnacaca | 540 |
| ngccttnana | antgntcaga | gaaccancag | tggntanggg | ntgcccnnnn | naccagggaa | 600 |
| gacccggggc | gtgncggata | ttgacacanc | agatnncatt | tggggncggt | tcgagggttn | 660 |
| atgntcnccg | agtacnagan | angatcntcc | aacccggaat | ncggtgctcc | ngtcgtccga | 720 |
| tgnaatgagt | cgnccggnaa | cctcatatcc | aagaaacnat | acagcagtgg | nntccgagtc | 780 |
| tcgtatanc | ntgcgggng | gaggctatnt | tcagaggnca | agattaccgt | tagcgggana | 840 |
| aagtngaana | | | | | | 850 |

<210> SEQ ID NO 6
<211> LENGTH: 531
<212> TYPE: DNA
<213> ORGANISM: Rattus norvegicus
<220> FEATURE:
<221> NAME/KEY: misc_feature
<222> LOCATION: 1- 531
<223> OTHER INFORMATION: n = g, a, c or t(u)

<400> SEQUENCE: 6

| | | | | | |
|---|---|---|---|---|---|
| ttgnggcngg | gtctcctctg | ngtgngngtn | tccccnanag | gggggtctc | acagtgtnng | 60 |
| ngtctnntgt | ctgtgtngtg | cccctgtccn | catctctcac | nccagggaga | gagatgtgag | 120 |
| ananacatca | gagatctctn | gnacagtgtt | tcacaagagt | ctatcncana | gagcacatct | 180 |
| gcccggggng | anacacaact | ctaaatgtgt | ctcanntgat | ctctctntg | tgtctctnac | 240 |
| atatgnggac | atgctctcag | agtatnggnt | ctcttgngcn | cttntgcaca | cacacacaca | 300 |
| cacacacaca | cacacacaca | cacncttctc | tctggcacag | ggntatggca | nagcacatnt | 360 |
| tnngagntca | nagctntata | tgagtgtgtg | gcgaaaggng | tnatnanann | gacnncccca | 420 |
| gcnnatatag | gggggngnnc | tctngggctc | tcttnggnaa | tntgnggng | agtctgcnca | 480 |
| cacaggcgct | cnnacccanc | nnnttgggc | ccccaggng | ttttttcnccc | c | 531 |

<210> SEQ ID NO 7
<211> LENGTH: 572
<212> TYPE: DNA
<213> ORGANISM: Rattus norvegicus
<220> FEATURE:
<221> NAME/KEY: misc_feature
<222> LOCATION: 1- 572
<223> OTHER INFORMATION: n = g, a, c or t(u)

<400> SEQUENCE: 7

| | | | | | |
|---|---|---|---|---|---|
| tttttntgtg | gccctttaaa | ctctgngtgn | ccgtntnccc | nagaggggg | gtctcacaag | 60 |
| gagacancgg | nnacacagag | gttttgngnn | tattgngagt | ctctgcgcac | nccananttt | 120 |

```
aaccncgggg nctcntgttt tattttaaaa aaaaagagtc ncatgtntat ttctctnatg    180
tgaaaatcnc attcanagtt ntgggtttc ccntgaggag anatagagtt tcacactctt    240
ctctccgagg ggtcntcnca tgtntctccc caatgtgngn ggnacacaca tgnggccccn   300 aggggtgng ctctctctgc ncagggcncc ccccaanang tagaganaca ntgtggtgtt    360
tcacaacaca attcncgaga nattntgttc cncantggnn gtctnagntc ncatgttgtg   420
gngacangtt agnncnccc atnttcnccc ccctttcaca ctgccccnag agagagaaan   480
tctnggcccc ctctanannt nttttttaaat cnccccnnac cacaggtntt cccagggtat  540
gngacntcnc cnnccccncn aaagatntgc nc                                572
```

<210> SEQ ID NO 8
<211> LENGTH: 906
<212> TYPE: DNA
<213> ORGANISM: Rattus norvegicus
<220> FEATURE:
<221> NAME/KEY: misc_feature
<222> LOCATION: 1- 906
<223> OTHER INFORMATION: n = g, a, c or t(u)

<400> SEQUENCE: 8

```
tgggagtctc tctcatatgg cgcnttcncc aaagggngt ctctntccng agncgcanac    60
gcgagaanac tctgtnnant ngtctccccc cncnccnaca gngtganant caaaacctct   120 agagccccc agaaanccc tntctcaaan aaagagaaag agaagancga gnagnagaga   180
gananagaga gagagagtgt gganctntnt cctcngancc ccannanan ngtgnggcnc    240 actcncnngt gnngngnacc ccngggggatt tncgcgtgtc cccttgngct ctgtntanga  300
gananatatg tntcgcccc ctccgntgtc acgtgtgcgg ggccnnngag                360
acacagacac ntctctcang gggaacacat anngactcnc acntgtgttt atattcnccc   420 ctccnctca cacanacaca cacacagnag atattnngct actctctctc tgtcacaggg   480
gtacanattt antctnggcc anaccctct cngaagngng ggcanngtaa accccgcccc    540
ctctcngaga angngaggc gntttacntt cccngtggcg tgtncgngcc cccgagactc    600
cccttngnac cccctntna accctctntt tgaacncaac ncaccntccc cnttttctcg    660
gggnnggncc ngcncccnct ctcncaaaaa aaattnnaan ttngtccct ncccntttt    720 ttcnggnana aaccgtgtcc ggggggggan nactctttttt tgnccttaaa atcaantttt   780 ttccccttt ccngggggacc cccgnnttcc tttttaaaaa aaaanaaccc tttctcccctt   840 ttaaaagnac ccntttttttc naaaaccgtt ccgnatttaa ttcctaaatt cccttccccn  900 ncccgg                                                             906
```

<210> SEQ ID NO 9
<211> LENGTH: 914
<212> TYPE: DNA
<213> ORGANISM: Rattus norvegicus
<220> FEATURE:
<221> NAME/KEY: misc_feature
<222> LOCATION: 1- 914
<223> OTHER INFORMATION: n = g, a, c or t(u)

<400> SEQUENCE: 9

```
gggatgngcc ctcagatcaa tacaccctc nggggngtc tctctctatc tcccncagna     60
gactcccatc tctntntntn ccccagnanc tgngaacgg ngtgtggnga nccntntctg   120
ttctcnantc tctaaaagng cnaaaagcgc ananacacgn gcctctctat anatctcacg   180
```

| | |
|---|---|
| tgtcccnngn nctctcngac ccctnntctg tntgagagac accctntctc aaaatatagt | 240 |
| gtacacgngc tttgnggctc tcccctttc tctccactnt tgagngngaa acgcggngtt | 300 |
| ntctctgaga tgtaganagn gtcccctnct cnatatatgt gttncccact ccnnagggng | 360 |
| tctcataaaa atcncntntc tcaacaccac cncctcnacc ccccncacga gaacacntcn | 420 |
| ccaccncnan gacacaaana naaggngtnn anaaccccan aaaaactnng ntntcngntt | 480 |
| tacacacaca cacacncacn ctcncncaca ccccacnna aatgggagaa aaaacagaga | 540 |
| ggngtgggtg ttngnntcaa caccntntta cctctctgnt gnnanttgag aaaatatttc | 600 |
| tntncttacc cctctccct ctctgtgtgt ngannatatc ngntctagat gtcctnaccc | 660 |
| tccccaaacc tttctcnggn agagacntct ctntntttt ccccncttc catttgaaan | 720 |
| anangagaag gnccaaaaag gnggngtct tctcgggaat ncnccttt ggcccccaa | 780 |
| cctgggtttt tttccccctt ccttttaatn antttcna nacaaanctt tnngngtttn | 840 |
| ggaaaangcc tttnnctgnn nnttttttcc cttccctt tnnangggnt tccccccccc | 900 |
| ccngaatttt tttt | 914 |

<210> SEQ ID NO 10
<211> LENGTH: 400
<212> TYPE: DNA
<213> ORGANISM: Rattus norvegicus
<220> FEATURE:
<221> NAME/KEY: misc_feature
<222> LOCATION: 1- 400
<223> OTHER INFORMATION: n = g, a, c or t(u)

<400> SEQUENCE: 10

| | |
|---|---|
| ttcctgggtg cggtctcctc tgagatagtg tatccctat aggggggtc tcactttagc | 60 |
| acagtttatg aatattatta catatttcac aagactttat attgttataa tatgcctcat | 120 |
| gtgagatata tgtgattctg tggtggtgtt ctcagagggg gtttgggtta ttggggataa | 180 |
| tagtttgccc ctcgcggggt ctatatttat atatgtgaca caatatatta gagagatttt | 240 |
| tggttatata tatttccctt cgcggggtg gagatttatc acaggggag agcttttccc | 300 |
| ttgttagcaa aagtccctgg tctcgtcccc catctcccaa aaaaaaaaa atgtgaaaaa | 360 |
| aaaaaaaaa agggccctc ttgagtgatg tccccttctt | 400 |

<210> SEQ ID NO 11
<211> LENGTH: 880
<212> TYPE: DNA
<213> ORGANISM: Rattus norvegicus
<220> FEATURE:
<221> NAME/KEY: misc_feature
<222> LOCATION: 1- 880
<223> OTHER INFORMATION: n = g, a, c or t(u)

<400> SEQUENCE: 11

| | |
|---|---|
| acccaatctt nanggtggca gtgnggnnga tcttaacggt ttttnagaaa aaaaantnct | 60 |
| tcgctcncac ccccaagcct cccnttctta ncagctttt tatangaaaa aagatgataa | 120 |
| cgaaatttta aaaaccgtcg ttagaggaaa tgaaggttca gccgaccatt acctganagt | 180 |
| aatgaaggtn ttccggaggg ttgccttcca atcccagatg gatttgagtt tcaggatcaa | 240 |
| ttcagttacc gntgaccatc caccnncctc cngtataatc attngatgag gatgaatggt | 300 |
| gagtgagtga tgatgatgat gatgatgatg aagggatgag aagnacacta tgataacaag | 360 |
| tgtctcagtc cacattaagg tttgcctgna aattagtgca taagccatgg gagacaaatt | 420 |
| cttttcnnac acaattaata gtntcttant ccttcccatc ttctctgccc cattctgttt | 480 |

```
tccaccacag gtctgcagcg ggctacagct tccagtctcc aagcaaatac cagaactgga     540
ggagaaaatt ccagtccagt gagtcatggg caggggagg ggtgggtaa gggcagtggc      600 gctcattcct nacatggtgt cttctcttgc ctagcctggg atctgagggc aagagaacct    660
gtaagcttga tttgatttcc actgctgact ggagtcactg ccaagggatt tgggacttct    720
ccatctctct ctctaacctg aaatccttag gattctatta tttcaccgga ccagagctgt    780
agcagagatg agctccaagt ttgaaatgag aaagggggaaa ttgagagcta tgagctaggn   840
gcgaaagncc ccacaaagnn tttggcaagt agaaaagncg                          880
```

<210> SEQ ID NO 12
<211> LENGTH: 909
<212> TYPE: DNA
<213> ORGANISM: Rattus norvegicus
<220> FEATURE:
<221> NAME/KEY: misc_feature
<222> LOCATION: 1- 909
<223> OTHER INFORMATION: n = g, a, c or t(u)

<400> SEQUENCE: 12

```
cgngagnngg cagggannna ggngggagcn ngagaggaga aggagaaggn nnggnaggng     60
nngngagnaa cgggcgggan cnnnngacga gagaangggn aggggancga agngcggngg    120
nagacggtgc nngggggga ggggcaggag nggnagagag gcangagngg agngggaca      180 agcnnaaanc gaggaggnan gangngangg nnggngngnc gaaggcgcnn aagnnggtcg    240
gngagcggna gnggnnaaac tgggaacga gacagacggc cccnncggng gcangnggga    300
gagnnncgcc agngagagna gncagnanca gancanggga ggggggggan ncacnggcgg    360
gagggncgan gacggnnngn annggnnaga ggcannnnnc gccnanagng ngaagngagg    420
cangagtgnc gcnngagnag acaggcccgc gcnccggggg cagacnnngg ncaccaccga    480
gggtgggngg ggcncggaga naagaccaga ggnnngaggg cganggcnng ggtnngcccg    540
ggccncccna aaaaannncc gaaaaaaaan agggggcgcn gcnggggcgg ggaggagcgc    600
ntnncgtang tngantgacg gaggccngna atgggccgn gccanncag gcgnagagg      660 cccaagngcg gnaggngnaa gnanagancc ngnnggtngg gagngangn gcnnggnncc    720 nacccccngn gttganggcn cccacgncgg ngcaggccgn nnaaagngag tcccnaaaa    780 nntcgnggtn tnacancgnc ccggggncgc cgcngngtcc cgncacacng gannncggag   840 annggcctnnt ntctncacan ggngccanac nngntgctat gcaaaagggg cgnacttcna  900 gaaaaagnc                                                           909
```

<210> SEQ ID NO 13
<211> LENGTH: 927
<212> TYPE: DNA
<213> ORGANISM: Rattus norvegicus
<220> FEATURE:
<221> NAME/KEY: misc_feature
<222> LOCATION: 1- 927
<223> OTHER INFORMATION: n = g, a, c or t(u)

<400> SEQUENCE: 13

```
cctttattcg gaggcaggga nnncttgtcc gggaangtta aacgtttttt aaaagggggn    60
ncccnggggg gggggnttnt ccagggaant aaaangtgtg gttgggggn aaaaatttat    120 tttnaaaaag ggcgncccat ataaangacn ttcgggggggg tttgaanagg gccggaancn  180
tcgacgggtt tccggggnggg ganaaggana agggnacgca cgggatttct tnccctttt   240
```

```
tngcaaattg cngcaggana ccaccgggtg gggnggtttt gttttccgtn aagaaagcgg      300
gngtggaaaa acanggataa acgggaagan ggggttatt nggttagnaa ttgnttccag       360
nggngccagg aaattggcct gtccaaaatt cttttcccng cttttaagac aggcaggtat      420
tatttggcag caggttatta cnataggnaa gtaaataaca atgggtaagt gcctggcaca     480
ggccagggta agtagggcat gtatggaatg ttaaacatta cccttcatcc tgagaaanaa    540
aanacaagna anaaaggctg gtctcacata tcccaaagct ttatcttcnt aggtgcccca    600
tggtgaacgt taagccaagc ntatgantca caagggacga catgggcagg ntagggtaca    660
gaatcagtgn tcagagactc caggggcacc cctgattccc tttgctgtca cacagacact    720
gctccaggga caaccctccg gatgtgagta tatgacttcc tgatggtgac gctgccgtga    780
tgggacactc ntcgtggtag cacacattcc tcagtcagct tctgagcntc agggtcccag    840
cagagcacag tggcaangac tttcattctt nttggncttt cccaggggc gtncccaaat    900 ggaagatttg gcaagntaag gaagntc                                         927

<210> SEQ ID NO 14
<211> LENGTH: 848
<212> TYPE: DNA
<213> ORGANISM: Rattus norvegicus
<220> FEATURE:
<221> NAME/KEY: misc_feature
<222> LOCATION: 1- 848
<223> OTHER INFORMATION: n = g, a, c or t(u)

<400> SEQUENCE: 14
ttttccaagt aaancanggg anttcggtan aagaagtttt aaanaagngt ccaggcancn      60
gaaattttcg nggntttggt taacgangca accagggggg ggtttcaang ggtcttctaa    120
tnatttnaan gggngtagtt tctggtnggt tcattccttn aaaaaaaaac aaaacaaaac    180
aaaccgnagc ttctgcattg gccaccngtt gnggcaccaa cccttnangc attgcccttt    240
ccttcctgcc gtgtcgggng gcgctaagcn gcccttgtca ccttccattt ntngatcatt    300
ttccatgtcc ttgcacttct gcttccactt cntgttggta gacgagctgt atgntcagaa    360
antgaagtac aaggccatca gcgaggagct ggaccacgct ctcaacgata tgacttccat    420
gtaaatgttc atgcaccctg cctgcttgca ccctcaccnt catgcttgtg tgatgacctc    480
accgtggctc ccccannann aaaananatc catgtctgca ccttttgttg gctttcttgc    540
ataacctagg ataggttatc ttttccacgt tgcactaaca aggccacgcg cattcggtcc    600
gtgaaaccac ctcggcatcc ttttatntca tagaggcaaa tntagcttgt ttctgccgag    660
agatgacctg gactccgaat gggctctgag tatntccttt taaaacctta aaccagantc    720
aagtaaagtt aggaagccat gaggcagtgg tgcaggaagt taggaagaaa naccgggttg    780
ttggtttcct gggnctgggg tgagggacca ttgatagacc tttacgaaan ganccgcang    840
atagaaaa                                                              848

<210> SEQ ID NO 15
<211> LENGTH: 896
<212> TYPE: DNA
<213> ORGANISM: Rattus norvegicus
<220> FEATURE:
<221> NAME/KEY: misc_feature
<222> LOCATION: 1- 896
<223> OTHER INFORMATION: n = g, a, c or t(u)

<400> SEQUENCE: 15
agagaaaaag gaaanannga aagaaagagg agnaaaaana aagaggnggn aanaaagaan       60
```

```
agangnanaa agaananant nngagattac gaantcgggg agagngaaag gaaacaaagn      120
nggnggnaaa gagnnantn tttcaagggt ccgnaacaaa aagttgagng angattccna      180
acaagggntn nccacccaan ctgntaaagg gangatttgg ncaaacanaa accngtattg      240
gggagttaaa aagagtcacc aaatagggaa aaaaagttng ggggagggnn aacnacnggg      300
taaaggttcc aggaccagag ngttcagnac caagtttcag tattcaggag gacagagttc      360
aggatcnntt tggaacattg gggtttgggt agcntggnaa cacgaaccct tttgttcata      420
aaaaggaagg gaaaagaaag ggnngaagag tnttcccaga tgnattntga gcagagaatg      480
cccgaccccc cgaatacgta gttccaaaat gggattgnac ctgtttcacc tcaaatttca      540
ntcntccttc tngtggacag acgcagggat ggggtcgggg aaggggngaa gctggtgcgt      600
gttctgtggt tgccggtgga tgntctgcag ctgtntaccc caccgaaaac gaatggatgg      660
gatgtcactc ccaggcagta gggggcgcac gcgcattgtg ttntagagag anttccccag      720
cctccccngg aannacaaca cgttntcttc ttcttaaggt ggtggtgggg gggggggga      780 agacctattg ctttccgaga ggatcggacc aaacagcaga ttntgctcaa ggcccttgaa      840
ccctgntatc tcactaaaca tctgagatac tgacattaca gatacggata tcgtgg         896
```

<210> SEQ ID NO 16
<211> LENGTH: 858
<212> TYPE: DNA
<213> ORGANISM: Rattus norvegicus
<220> FEATURE:
<221> NAME/KEY: misc_feature
<222> LOCATION: 1- 858
<223> OTHER INFORMATION: n = g, a, c or t(u)

<400> SEQUENCE: 16

```
gccaatcaag ttncggttaa attttggaaa ngnggcgaat gcnntgtctt gnggattttg      60
gagggnggaa ngtnggtnaa agagtttaa tgttcttggg atcgcaanta ttttcctggt      120
tcgcgncttg tacattatga gggttgataa cngctgtttt tngattttgg ttaacanggg      180
ngggngcntt tttnggntga cctntagtnc ntcngngccg ggcattttgg ntacctttt       240 atttttngaa gtncagggat gttgtgtact gggaatattc cttagaagtg accatgattt      300 tatatttat taaatatata cttagattca ntctttgcct aagcctggat gttgttggtn      360 tttgttttg ttttgttgtt nggagagttn tcatttttccc aagctggctt tgaacattca      420
cttccacaca aacatgtcca cacacgggca aaggtgtatg cacagatatg gacataacac      480
acacagagaa gaatnacaaa caaacaaaca aatatttcn gacagaaaca antaaataca      540
tccagaaggt agaatattct acaaggcatc aaatctgttc taaagaaaaa gttataataa      600
agaaaaacat tgaaggcag gtgaaggaga ttgaaggcca taggggccac aaaaaggttt       660
aaacagcaaa gcaccaacgt agatatccgg aacgtgctaa atatgcaca cacaggatat      720 ccgggaacga tgagtcagcc agcggcacat ataaccaacg atgtaatctg ttatgtaact      780
atgaatcatc cctggcagag tgccacctt gtgtgatttt tgtataaata tgcccctgag      840
accagaagcc attgccttt                                                  858
```

<210> SEQ ID NO 17
<211> LENGTH: 551
<212> TYPE: DNA
<213> ORGANISM: Rattus norvegicus
<220> FEATURE:
<221> NAME/KEY: misc_feature
<222> LOCATION: 1- 551
<223> OTHER INFORMATION: n = g, a, c or t(u)

<400> SEQUENCE: 17

| | | | | | |
|---|---|---|---|---|---|
| ttntctgtac | cccttctca | aaaaagtgg | ctggtgnctt | ttctcngaag | agaatcctca | 60 |
| ccnccncana | anaaatatct | ctctcccccc | cttgttgntt | gtcnccnnc | ccaaaantgt | 120 |
| gngatctntc | tctctgtgca | cgaganattt | tagaggggga | tatccccggg | gtgtngccng | 180 |
| tgtctntcct | ctcgcgaata | tctttangag | nctctctctc | tcganccccc | agngtaggnn | 240 |
| gagngganaa | cattttntg | tggnggcccc | ccacaananc | acnaacaana | tattttcgag | 300 |
| aancncatgn | ganaatcggg | gggggggggg | ccngtgttna | cacnatancc | ngggngatna | 360 |
| nanagacacn | nnatatntct | gggntgtgna | aanataanac | aagancanac | atgnggagan | 420 |
| natgtgagan | tgtgcacacc | ctgttgtgac | atgtgaggtg | gggggctgat | gatncctncc | 480 |
| ttctacgtnn | tntcttctcc | tccncantga | tagacnccac | ctgctggagt | gnctagctan | 540 |
| ctggggtcgg | t | | | | | 551 |

<210> SEQ ID NO 18
<211> LENGTH: 888
<212> TYPE: DNA
<213> ORGANISM: Rattus norvegicus
<220> FEATURE:
<221> NAME/KEY: misc_feature
<222> LOCATION: 1- 888
<223> OTHER INFORMATION: n = g, a, c or t(u)

<400> SEQUENCE: 18

| | | | | | |
|---|---|---|---|---|---|
| gttaaatatg | aaaagtggg | ggtgacaggg | ggtgataccc | tttgcgccgg | gctatggatt | 60 |
| tttggcaccg | ataagatttt | caggtgacat | ggaaggtggt | tggggatggg | ggaaagtttt | 120 |
| gaggggccaa | aaggataagg | aggatgattg | attggtttgg | gagcagtact | tggaaagagt | 180 |
| gtgtttgatc | ggtaaacaac | cacgtgtagt | gtgttttgt | tgcagcagag | ataagtgaga | 240 |
| aaaagatttc | aggagatctt | gattttttc | gggtcgagct | atgttggggg | atgtgagggt | 300 |
| acaattcaca | agatttgttc | acagggagtt | ctaggaggtg | gtcccattag | ccggtagggg | 360 |
| ggttttctca | ataaatgggt | tcagtcaggt | gtttgcctag | atctttcatt | agttcctccc | 420 |
| ttcaaaggga | ttttgaagga | gtgctttgtc | ctgtggagca | attgactcaa | tcaataaact | 480 |
| taagtaatct | cccggattac | tgttgatgcg | ttcccagaga | ggtccccgt | agttaccagt | 540 |
| gaatcacaat | ttcctaacca | tatgattttt | gttaatctca | ccacataaac | ccacaattct | 600 |
| cgcgtccttt | gtgatggttt | caaagtctgg | aatattttt | cctccatccc | tcctttcctt | 660 |
| cctccttta | tccctccctt | ccttttcc | tttcacagga | tctcattatg | cagcccagtc | 720 |
| aggccttaaa | cttgtgatcc | tcctgtctca | gcctcctagg | tgttaagatg | acccaaatgt | 780 |
| aaaccatgtc | cagttacttc | ctcctaatcc | catcttcaga | tatcctttaa | gaccaaatta | 840 |
| aatattaact | gaaagacccc | accagtaggt | ttggcaagct | agcaaaga | | 888 |

<210> SEQ ID NO 19
<211> LENGTH: 867
<212> TYPE: DNA
<213> ORGANISM: Rattus norvegicus
<220> FEATURE:
<221> NAME/KEY: misc_feature
<222> LOCATION: 1- 867
<223> OTHER INFORMATION: n = g, a, c or t(u)

<400> SEQUENCE: 19

```
cttttttctaa attttttaac gggggaaatc aaacggcaaa aaagaggggg gaccacctca      60
atcacccaca gtggaaaatt ggtgggtatc aatcaggtgt tattagggg ggaggaatgt       120 tggggaacaa aaaaaaaatt ttaaaaattt ccagggggt tttgaaggca ggtgatttaa       180
aaaccgcccg tcagttaagg gggttttatt tttttttaat aaaaaataaa attaggattc      240
tggaatagaa ttttaattc agggatcctt attttaatg tttccagggt aaaagggaga       300
tattcttatc aggtttctgg aaaaagtttg cttggttttcc tttggcagga gagaggttta    360
aaaaagactt catttgaact ttttgatcat tgtgtaaaac tttttttttt gaacaaaaca    420
ataaaatgta aaagatata gatcttaggt tttttaaaag acaaacatat aaatattaa        480 aacagattgt ctgtcccatg caaatgactg actgaccttg taacagctcc acagagtgtg     540 taaaacaaa aaaagcccc ctgagagcct tgagccatca ggttaagtct catttattaa       600
tattttcaag gccacaggag acactctgtt cccttcattt agggaggtgc tgaggcagcc     660
atgttttccc agcagtgggg gttgggcaga gccactccag attggcttgg aggggtgtgt    720
agctctcagt ctgcccggac ttggatggtt tattttctta aacgaaaaca cctgcctgag   780 aaagagcct tttcacgggg tggccaagtc ccagcccgcc ctgggagcca aggtcaagtc    840
ttagcttagc gttctaagga cacagat                                          867

<210> SEQ ID NO 20
<211> LENGTH: 897
<212> TYPE: DNA
<213> ORGANISM: Rattus norvegicus
<220> FEATURE:
<221> NAME/KEY: misc_feature
<222> LOCATION: 1- 897
<223> OTHER INFORMATION: n = g, a, c or t(u)

<400> SEQUENCE: 20
aaagggnanc aaaaccntaa nggggagggg ngggaaatg gccaaaantt ggggttaaaa       60
aaagttagga tntggttgga tccnacccac aaggaatttg ttnttaattt tttaaaggna    120
aatttgggca cttcnattgg gaaggttaaa acccaggcaa gtgntaccgg gntatgcaag    180
tgaaacntga ttctggnggt ggagggaagg atantganat gtgagtgagt gcagttgagt    240
gaggacttgt gagnacaggt catgcccacc aaagggagga gcaagggtgg gcagtggtag   300
gtggtgtgtg gttccttct gggggntggg cggggagaca gatgagaacg ntattggagg    360
acaggnacaa gtgtactgaa atgcaaatcc ctgtagatct ggaaaaggtc tggnttcagg   420
cttgatgctt gggccggcaa ctgtgnacct tccctgnacg ttcagccccc ccaccttac    480 ggaagttttc gtcactgaag actagtggct aatcagagtc ttcaatggac ctgccaatca   540
gaaaggaagg cgggntnttc cgggtgcnta ggtgtaggat tcgctcagta gttaagcagt   600
cttaactggt tctggctgct gtgctntctg tcctgccgtt ggattntctg aggcatgttc   660
aggcaagctc caaagttgcg acatggtgag cacaggggca gggggggcgg gcggacgggc   720 agggactga gcagtgggag ctggtgtggt gggtctttcc cggggctgag ttggaatccg    780
cggctacccg tgaggtctta gccactcact agacccagcg gcagtttctg aataactttc   840
nttgtagggg ttggnactcn gnaaagactt ccacnaaggn cttggcaagt agaaagg       897

<210> SEQ ID NO 21
<211> LENGTH: 435
<212> TYPE: DNA
<213> ORGANISM: Rattus norvegicus
<220> FEATURE:
<221> NAME/KEY: misc_feature
```

```
<222> LOCATION: 1- 435
<223> OTHER INFORMATION: n = g, a, c or t(u)

<400> SEQUENCE: 21
gattccagag agaggagtga actggcagat aaggcagtca gcataatggc ttagatacca      60
tgtgctttcg ctcactatgc acccatgaca caagatcaca gggtacaggc ctggaccatg     120
gcagagtata cactggttgg gtaaatgaag aggagagaca gagtgggaag tcggcttagt     180
ggatatggac ttcaaatttg atgaacaagc aattcaaatg agtatcgtgg gcttgantgg     240
tatgaagacc cgtttgcaaa gcagtggtca taagagagaa aagagagaga gagagagaga     300
gagagagaga gagagagnaa gagagagagn gtgtgttgtt gttgttgttg ttgttgttta     360
ttggttnata acaanatnta cctttgggcn ctttngaaag actntncaca aaggagcttg     420
ncaagctaga aaggt                                                      435

<210> SEQ ID NO 22
<211> LENGTH: 894
<212> TYPE: DNA
<213> ORGANISM: Rattus norvegicus
<220> FEATURE:
<221> NAME/KEY: misc_feature
<222> LOCATION: 1- 894
<223> OTHER INFORMATION: n = g, a, c or t(u)

<400> SEQUENCE: 22
gaaaaaaaaa aaannataat tttaattttt cccccatttn aagggaaatn ggaaattaaa      60
natnggtttt nagcccaatg gaaattaaaa ttaagaaggt tgttttccaa aaacctttcc     120
ctagaggana accggccnat aggngggggn agnatggaag gattttccag agaggaatca     180
gtttggngag agaatttgat aaggagttcc ttggaaccaa ccnggagggg gttttggttt     240
nngggattna tcangatggt tgtccttggg aagcataagg ntggtttatt attttggtta     300
aaggggatga agtaccntgt gttgcacttg gtagcccaat gtcctgtcat tgtgctttgg     360
atgtaggcag ctttgaaggg atttntcctg agaggatctt ccggatcaga gtatatcgcc     420
ttttcttggt gaggccccat agtgggantc cgcacttcac catttctttt ccgcccgccc     480
cagttcggtt ntaacccacc cgcgtggcca cgatcccagg acatagcgg gacaggcccc      540 gcagtgcggt gacacacgtg ggcacacccc acctgtgcag ccggtggctc gcgntgaagg     600
acacgaggcg cgacaatcgc gcgcggcgcc gaaggccaac cgccgcgttc atggtnttca     660
gaccaaagac ccacaagnta cgggttccgg tttccgggac ngaggccagc ccggttcccc     720
cgcggntgcg cagtgcaaan tcggccttcc ccgccggaag tactcctggg agcggtttcg     780
gcgcgtggca cttttcggtc cacctggagg caacactggc gccntttcct gtttcagtct     840
ttgntaggct ataagtgaaa gaccccacan gtaggtttgg caagctagcn aaag          894

<210> SEQ ID NO 23
<211> LENGTH: 594
<212> TYPE: DNA
<213> ORGANISM: Rattus norvegicus
<220> FEATURE:
<221> NAME/KEY: misc_feature
<222> LOCATION: 1- 594
<223> OTHER INFORMATION: n = g, a, c or t(u)

<400> SEQUENCE: 23
ccattaatgg gggngggnaa agggataggg atttgggccn gnnggttant ggggaagtgg      60
gattttaagg aattccccaa aaatattgat tcttccaaag tatttccctt catttcccaa     120
```

-continued

| | |
|---|---|
| nagagtaatt tcaaaagccc cagntttgtg gaatcanttt ttgaanatat gaaaaggccc | 180 |
| taatggtttc ggcattatta aggcccgctg aggacactgn tcaagttact cttggaaggc | 240 |
| gtttntggca gaaacagaac agccccgttg gcacggacag tgtccactgt ttatctataa | 300 |
| atcttttcaa gcagatcttg cagccaacta ggtacaagag tcggatgggg atgggggcg | 360 |
| gggagtcaga gaggtcggaa caatgaggcg gaaaccaaaa ntntgaaaca cgcccacctg | 420 |
| aacaggacga aaggtgggg cttggtccac ccagaaggaa acctcgaact ccacntttca | 480 |
| aggtatccgc tccggttag cagccccggc caaacgcccc tgctggcttc taacccaacc | 540 |
| agctacgaaa gcaggctnga ccactagctg ncctcgactt gaaagttccc acaa | 594 |

<210> SEQ ID NO 24
<211> LENGTH: 586
<212> TYPE: DNA
<213> ORGANISM: Rattus norvegicus
<220> FEATURE:
<221> NAME/KEY: misc_feature
<222> LOCATION: 1- 586
<223> OTHER INFORMATION: n = g, a, c or t(u)

<400> SEQUENCE: 24

| | |
|---|---|
| atccaatnat tgggagtagg acaggggatc gggattngag gccagttggg ntagtgggat | 60 |
| gctgggaatc ttaaggaatc cccaanacat atgattctt ccaaagtatt ttccatcaat | 120 |
| tccaaataga tgtatttcaa agccccagc tttgtggatc agttttgca ntatatgaaa | 180 |
| aaggcccttan tgnttcggga ttattaaggc ccgctgagga cactgttagg gcgcntcaag | 240 |
| ttattcttgg aagggtttct ggcagaaaca gaacagcccc gttggcacgg acagtgtcca | 300 |
| ctgtttatct ataaatcttt tcaagcagat cttgcagcca actaggtaca agagtcggat | 360 |
| ggggatgggg ggcggggagt cagagaggtc ggaacaatga ggcggaaacc aaaantntga | 420 |
| aacacgccca cctgaacagg angaaagggt ggggcttggt ccacccagaa ggaaacctcg | 480 |
| aactccacnt tcaaggtatc cgctccgggt tagcagcccg ccaaacgccc tgctggnttc | 540 |
| tacccaacca gctacgaaag caggcngacc actagctgac ctcgac | 586 |

<210> SEQ ID NO 25
<211> LENGTH: 909
<212> TYPE: DNA
<213> ORGANISM: Rattus norvegicus
<220> FEATURE:
<221> NAME/KEY: misc_feature
<222> LOCATION: 1- 909
<223> OTHER INFORMATION: n = g, a, c or t(u)

<400> SEQUENCE: 25

| | |
|---|---|
| gggggttgn aaattgagaa gcccncctttt cntctttgtt gtgaanacat ttnccntncn | 60 |
| gggggatccc tnggttccgg aagggccgcc ttagttnttc ttttcctcca cctatgaaag | 120 |
| gggnggggagc cgattaaaag aagggnggag cagngaggga agcggagctt cgcccgtttt | 180 |
| ccgnacccttt aaccctgctt gttcgggggg ggagngtgcc accnaccggg gngnggtggc | 240 |
| acggagatnt gaggggggagg gatggttttgc cntggccgct ngtgggtggg cgggcaggcg | 300 |
| ccggcattcc cggcaccttc ngaagacnga gccgggttca ggacnnaca ntccccgcca | 360 |
| agngggacca accgcttcgg gtgggttccc cggttgtntg gtgcccaggc cgnacgccgn | 420 |
| gacngaggga gacccaagga cntagantca ccggtgagcg ggccggcgcc ggagagcgga | 480 |
| aagaggagcg tagcacagcg cagntcggcc agacgttgtt cttntaccac ccaccgagcg | 540 |
| tttaaaaaaa anaaaaaaan cccgcggcag cggactttt ttgtagcgga gcccgggcgn | 600 |

```
gtcacttgcc ggaagtcccg cccntcgttt ctgccaccgc ccntcggtta cctgggcaac    660
ggcgcggggg cggagagtgg ntgcgcccaa gggcnttgtg ggggtggact caggcccggg    720
ttcccgatcc tngtagaatn tttntagaggc ttttcttta tgcgaggtac cagagggcgg    780
aagtcttgag gtggagaggt catgtcccag agccgtaagc cggggacgag tgctntcagg    840
cnntgtgcan ttgggatcct nnggnccacc ntgagggtcn tcacaaanga agcngncnag    900
taaaggagt                                                            909
```

<210> SEQ ID NO 26
<211> LENGTH: 576
<212> TYPE: DNA
<213> ORGANISM: Rattus norvegicus
<220> FEATURE:
<221> NAME/KEY: misc_feature
<222> LOCATION: 1- 576
<223> OTHER INFORMATION: n = g, a, c or t(u)

<400> SEQUENCE: 26

```
ggcaccgggg taanangggg gggagtngtc ctgggnncct tgaacgctgg gggaggantg     60 gtnggggggct ccaaggggggn ngggggaganc tnaagntcnt caanntagag aggggggaagc    120 tccccactct acatctgttg tcggagcacc ccccaccca gagggcgctg tcagtcatag    180
actagagacc tccccctcaag tgnctcnatc cttccaatag acgagccctc ttgacgcctt    240
tttcagagaa ttctctaatc ctcgggtcac ttccgccccc ctgtcaagac ttcacatatg    300
tcctccacgc gagggggtgt ctagaaccat cataagaatc tctctgtcct cgttctttcc    360
tgtgataaaa gccgcgggag nttccttttg ggcgtctaga tctccgtgct gagtgtctcg    420
ggagagcgcg cgacatcgcg tgtgaanngc gacctgtctc cgcggagaat gggagtgtct    480
gtgtgcagat gtcatagtga gaaaccaccg ataagggtga tagggtaaaa gatacttaaa    540
gggctatgaa gaaagtgggg aagggaggag gggaga                              576
```

<210> SEQ ID NO 27
<211> LENGTH: 853
<212> TYPE: DNA
<213> ORGANISM: Rattus norvegicus
<220> FEATURE:
<221> NAME/KEY: misc_feature
<222> LOCATION: 1- 853
<223> OTHER INFORMATION: n = g, a, c or t(u)

<400> SEQUENCE: 27

```
aacncccctt ncggggggng gggaaaaana aagggggtng gnggaannta aaccctagtt     60
taaaangggn tanangtntt taangggcna aaagnttggt ttnantccca ggngggtccc    120
tcctttgaan acccngaaaa attcatttnc agaggggttg gaaggggggag ccgaaaagaa    180 acccaacna cttcgcaagt aacaangggc cnaaggggagn cagccgcacc tttttttccnc    240 cccgcccaaa ggccagccgc attcaccatg aacagataga ngtaggaggc aaacaattcc    300
agttaatntg gcggttgatg gcancttcgg attcttggtg gtatttctgg cgnatttgcg    360
agggagacgc ggtgttcatg atggcggctg ggngaggcgc ggaggcgacg ctggagcggc    420
ggagcgacga agttgcaaag gntcaggttc aaagcgnccg gcggggtcgg agggggtcgag    480 caccggttcc gttcaagcac tgttgaagca ggaaaccgcg gngantctgg gcgagaangt    540
ctggcgtagg gaccagcggg ccgcactttta tagcgggatc ntgcgtcagg cgcgntccgg    600
ccaatcagcg cggtgggccg cccagccccg cttnttcctg taggcgtgtt gcccaagcca    660
```

```
gcagtgcgtg ggcggggagg agcctgtgtg attgtgaggc gantcttggg gttatgagct      720
gntgcaagag cggtgcctgg caacaagcgg gacgtttntg tggcccgggg cggacgtagt      780
tggaaccagc cgtactacag aggcattctg ggtcccagag agtatcgata aggttgattt      840
ttaagtccca ccg                                                         853
```

<210> SEQ ID NO 28
<211> LENGTH: 825
<212> TYPE: DNA
<213> ORGANISM: Rattus norvegicus
<220> FEATURE:
<221> NAME/KEY: misc_feature
<222> LOCATION: 1- 825
<223> OTHER INFORMATION: n = g, a, c or t(u)

<400> SEQUENCE: 28

```
ggnttncagg ggnacccccc cccncttnn antttgtcca cgnaanattn nngccnnnna       60 aggangggn nggggaagttt nagggcaang aaaagggaaa agtttngttt ggacaaacct     120
tgaaaggggn tttatcgcaa nacnccgggg gggggttttt ttgaaagaga aggggaaaag    180
attcggaanc ctgattttttt tggnttgagt naagnggggg angggnngna aaaattaaan    240
ggattccngn ggggngact agtantttag gggggagaaa agggttttat aaggncccat      300
aaagttcagc ggaaagccgg ntccggggaa gaccacccat gngtttaat tagagtgcaa      360 cgggttgaag agcccaggaa gcccaganac tagggtgagt caccgngaaa ntaacagacc     420
ataaaaggaa ggatgcagaa cagaccaggg tacnantcac aggccacttg gcaggaagag     480
atagccccca gccccngaat ncagagcccc aacctgccaa tgnggtagnt ataccttatt     540
acttcatcat gtgaatagcc aatcatatgt gaacatgtnt atgtgcttcg tttgaatcca    600
ccaatcccng taantatgat ntgttctgna cgcccgnttn tgttccccaa tccntataaa    660
agccccatgc tggagctgct gggcgcgcaa gtcntccgaa gagactgtgt gcccgcaggt    720
acctgtgttt tccaataaac cctcttgctg attgcatccg agtggactcg gctcggtcat    780
tgggcgcttg ggactcctcc tgagggaaag tcctctctgg ggtct                    825
```

<210> SEQ ID NO 29
<211> LENGTH: 861
<212> TYPE: DNA
<213> ORGANISM: Rattus norvegicus
<220> FEATURE:
<221> NAME/KEY: misc_feature
<222> LOCATION: 1- 861
<223> OTHER INFORMATION: n = g, a, c or t(u)

<400> SEQUENCE: 29

```
anngaaacat nccnncnnn ttnatcctt nggaaaaggg canccccaaag gnnnggaacg       60 gatngaanaa ttctttcaaa aagaganatc ggangggnnat cgnnnnggtt ttcaagtccc    120
cccngagnan naaaattgag tcagtngggg gnaaccgacg nanananggaa caggtttccc    180 gggagtcctt gggtntcngt tcgaccccg gaaaccgaac tnncgcnttt ncctttggga     240 gngggattt ntaaaggnna ncgggngat ttccattcgg ntagttgttn gttcaagggg     300
gntgccggac ggaccccctt tnagccagac ngngnccta tccgnaaaan tgttggggtc     360
caacccggta agacagattt ntcgccantg ccagcagcca ntggtaacag gattagcaga    420
gagaggtatg tagacngtgn acagattaag gaagtggtgg cgtaagnacg gacacattag    480
naggacagta tgnggtatct gcnctcggtt gaagccagtt accttnggat aanganntgg    540
tagntttnga tcccggcaga caaaccaccg ttggnagcgg tggntccttt gnntgnaagc    600
```

```
agcagantan gcgcagaaaa aaaggatctc gagaagatcc tangatatnt tgttcggggt      660
cagacgctna annggtntgg natnntganc ggntgaccat agagcacagt antgnngatt      720
gcagtccgcc ccnaggacga naggagacca ggggcccang ctgnagtaac naatcaacta      780
ccctnacnag atgnancaga gagagagagn accgtatant nantgnaaga gaggtcccgg      840
tttcnagttc ccagnacgga a                                                861

<210> SEQ ID NO 30
<211> LENGTH: 149
<212> TYPE: DNA
<213> ORGANISM: Rattus norvegicus
<220> FEATURE:
<221> NAME/KEY: misc_feature
<222> LOCATION: 1- 149
<223> OTHER INFORMATION: n = g, a, c or t(u)

<400> SEQUENCE: 30
attngaggag atccggttac taaggatata gaagaaaaaa ataaatcgtg tgcctgcctt       60
ttttttttta attgcctgct tctccccacc cccaaattaa gttgcttagc aaggggaaa      120 gaggcttttc ctcccttcag taggtcagc                                       149

<210> SEQ ID NO 31
<211> LENGTH: 857
<212> TYPE: DNA
<213> ORGANISM: Rattus norvegicus
<220> FEATURE:
<221> NAME/KEY: misc_feature
<222> LOCATION: 1- 857
<223> OTHER INFORMATION: n = g, a, c or t(u)

<400> SEQUENCE: 31
gatctggtct tgcccnggan ganntcnntn ccggggggggn taaaaaagaa ttgntggngn      60
tgacnagggg gganaccccn taccgnggnn cnancggaan tnttggncac cgnaaaaaat     120
ttccaggngn acangaacgg gtgcggnggg antaggggga aangtttgga gtgngccaaa     180
acggaaaagn agacgnttgt angggttggg aaccagnacc ntggaaagan tgnagttctn     240
atcngcaaca accaccggag gtaggggggtt ttttgtngca gcacagatan gcgcagaaaa     300
aaggatttca ggagatcctt tgattttttat tcgggtanga cgttcangtn gngggggattg     360 ggagcggana accatttnna cacaggattn tatgaactat ggtcanttgc tttgttgtcc     420
angtcgttgt gggattgctg tttttagtag ctgcaaacgg ttcgtttttnt gctatctttg     480 ttnngataaa tcagccccgg gcagangana ttcgaaagtt cccttttagga gcttatttan     540 acgggctcaa ngccaccggt ttcgttttn taggcacgtt ctgcgcattt ttttttttn     600 gnatntttgg atcgcgtttc gtgggatctt aaaaaccgtt ttctgtgatt ggcacgcaag     660
aaanactcat gagctggtcc ctgttgtgtc tctcaggacc aatcaaanac ccatttccaa     720
cggctttata atgtctggtt ctgtttgcac aggaagcgaa gtcacggctt gcaccccgtga     780 agtctgggga ggttcagagc tgggaactgc ccagaggaag gggttcgggg ctacagccat     840
caatcttcca gttgttt                                                   857

<210> SEQ ID NO 32
<211> LENGTH: 1630
<212> TYPE: DNA
<213> ORGANISM: Rattus norvegicus
<220> FEATURE:
<221> NAME/KEY: misc_feature
<222> LOCATION: 1- 1630
```

<223> OTHER INFORMATION: n = g, a, c or t(u)

<400> SEQUENCE: 32

| | | | | | |
|---|---|---|---|---|---|
| cccccccccc | cccaaaaan | aanaattacc | nttttaccat | tgnggttccc | ngtccntgat | 60 |
| aaatttttaa | ccnncntttt | tccttaaaaa | ancgnatcct | gangggattt | ccgttnaatg | 120 |
| gnnttaannc | ttttngngaa | tgtttaccccc | aatnttcccc | tnaattttga | gtnngataat | 180 |
| tgcttanagg | catttggaaa | tttaacggnc | acctgaggtt | gattggttgn | tattnaacgg | 240 |
| acttngatnn | gaggaaggcc | cccaanattt | tgttccattc | cttntaagtt | tgggacttgg | 300 |
| aaatcccgtt | gtttagatct | tgaccgtaat | caggagtcag | cgtagaggag | gccccggaag | 360 |
| gagggcccag | cgcggattcg | cccgcggcag | ggcgggacc | aacagagggc | cntcggggat | 420 |
| aggggagcgc | cgccccgccn | tcccggggaa | ggacacattg | cttgttagca | ggaagccagc | 480 |
| cagacccgga | ggaggccgct | ccagcgttgg | tgttgccggt | ccggggctag | cctgatccgg | 540 |
| gcagggtgag | ttgagacgat | cggtgagct | tgggccgggg | acgccagcgt | cttcagtcct | 600 |
| ggggattgtc | ccaggagggc | aaggagcttg | gaggagggag | gccgcacagc | tagggagtc | 660 |
| aggtctgagt | cccgagtgtg | ctctaaagcc | ggggcggtga | gagtggcggc | ccgcccgggg | 720 |
| ccgcgcagcg | ngcagtctcc | cccgcgtggg | aagtggtaac | ttaacgcaca | gccacaggat | 780 |
| tcccggcctt | tagctgctgg | agggagggtg | gcttctcccg | gaggagtctg | ttgtgaaact | 840 |
| cggttggagg | gcaccgtggg | tgcgggcaag | ggagagatgg | ggtcgccctg | aagaagtggg | 900 |
| gggctggagt | agaaagtgga | ctttgtgcaa | acctcacccc | agagtagtta | gttaccaagg | 960 |
| ctggttttttt | tttttttttt | ttttgctca | gacacaagga | aaatttgact | caatgttaaa | 1020 |
| atatgtaatt | tggcaggaaa | acttttttcc | tagcctcctt | gctaatatag | ttggaacagg | 1080 |
| gggctcccaa | gaggtataga | gtcccccatt | ttacaaaatg | tggttcagtg | ggactgtggc | 1140 |
| ccacccagtc | gtgtatccat | ggaagagtgg | cttttatgga | gaagttcatt | ttccttaacc | 1200 |
| ttaaaaactg | taaaggatct | tgtgcttgag | aatattgttg | gccagcttta | tagtcttcat | 1260 |
| ttataaaact | atttagacta | gagtgttata | gattataggt | cttcaagttt | ccagtcacca | 1320 |
| gtccttggct | ttttagtatg | gaaatcacca | gtaatggcaa | tataacatcc | ctgcttctgt | 1380 |
| ttcttagaag | gctaaattac | agtgtgttca | aactccgtgt | cattgcaaca | ggttaaacta | 1440 |
| actttatacg | taggacatca | gggtattgac | attctcatcc | taaagtcagt | ttgtctgttt | 1500 |
| ccagaggagg | aactgaagca | gtggttcttt | aagtaactga | ctcagggctt | tcctgcctgg | 1560 |
| cgcgcctgcc | aggcatagtg | tagcattgta | ctgcatcttc | tttgaccagt | ttccccaggt | 1620 |
| gaagagcctg | | | | | | 1630 |

<210> SEQ ID NO 33
<211> LENGTH: 883
<212> TYPE: DNA
<213> ORGANISM: Rattus norvegicus
<220> FEATURE:
<221> NAME/KEY: misc_feature
<222> LOCATION: 1- 883
<223> OTHER INFORMATION: n = g, a, c or t(u)

<400> SEQUENCE: 33

| | | | | | |
|---|---|---|---|---|---|
| aaaaattgta | aggagttggg | ggnatccccc | ataattnaaa | nagggaacaa | nccntaaagg | 60 |
| gagggnnggg | aanggccaan | attggnttaa | aaanagtang | tttggttgat | ccanacacaa | 120 |
| ggaatttgtt | anaattttnn | taatggaaat | ngggcacttc | aattgggang | ataaaacccc | 180 |
| aggaagtgat | accnggggtta | tcaagtnaaa | cntgattctt | ggngnngagg | gaaaggatat | 240 |

```
tgaatttgag tgagtgcagg tgaagtgaga cttgggagna caggtcatgc ccacccaagg    300
gaggagcaag ggntgggcag tgtaggtggt gnggtggtcc ttcctggggt gggcggggag    360
acagatgaga acgttattgg aggacaggca caagtgttac tgaaatgcaa atccctgtag    420
atntggaaaa gttctggntt caggcttgat gcttgggccg gcaactgtgn actttccctg    480
tacgttcagc cccccaccc ttacggaagt tntcgtcact gagantagtg gctaatcaga    540
gtcttcaatg gacctgccaa tcagaaagga aggcgggctt ttccgggtgc ntaggtgtag    600
gattcgctca gtagttaagc agtcttaact ggttntggct gctgtgctct ctgtcctgcc    660
gttggattnt ntgaggcatg ttcaggcaag ctccaaagtt gcgacatggt gagcacaggg    720
gcaggggggg cgggcggacg ggcaggggac tgagcagtgg gagctggtgt ggtgggtctt    780
tcccggggct gagttggaat ccgcggctac ccgtgaggtc ttagccactc actagaccca    840
gcggcagttt ctgaataact ttccttgtag gggctgcaac tct                      883
```

<210> SEQ ID NO 34
<211> LENGTH: 913
<212> TYPE: DNA
<213> ORGANISM: Rattus norvegicus
<220> FEATURE:
<221> NAME/KEY: misc_feature
<222> LOCATION: 1- 913
<223> OTHER INFORMATION: n = g, a, c or t(u)

<400> SEQUENCE: 34

```
ttccccccna gaaaatatt tttngggacc canaaaaaan ggtcccnggn cctgttttct    60
tccncccgna aanaacttcc ntttccntgg ggggntttaa naaaagaana tttcattggn   120 ggtttttntcc naggggggga gaccccnttn nccgcgggcc tttcgnaatt ttttggtcca   180
ccngtnaaag attttcccat ggcgcaccat gtacggttg cgaggngtat taggcggnaa   240 cggttttna gtgggcctaa tacggnanat aggaggacga tttgtnttgg tttgtngagc   300
cagtaccttn gnaaagagtt gtagttttga tccggcaacc aaccacngtt gtagcgnggt   360
tttttgttga agcagcanta acgcgcagaa aaaaggatnt caggagatcc tttgattttt   420
cttcgggttc ngacgttatg ttgtgtggat tgtgagcgga taacaatttc acacagattc   480
cgatngtagt ccaatttgtt aaagacagga tatntttccc ttcaaagaaa acagaaaaat   540
acagaaacgt taattttcaa atctcnaatc tttcnttctc tcttcnntca ttcattcntt   600 cnttcttttct tctttctttc tntctttctn nagaggaggc atgctagggt aacagtagct   660 catttttaaaa tctggcacct ggaattaatt tagggacaaa acacctttat gcaaaaaaaa   720
gtttatgttt ttccatggaa cacagtaaaa tcaaaattaa agaatataa caaaggcttt   780 ggtgatttgg taggatttt ttttcctgg aggggaaaac agatgacttg gaaagtgtta   840
ggaacatatc aagccccagg gaaagaaaaa cgtttgattg gtattaatta aaacactgct   900
aatatattct aat                                                      913
```

<210> SEQ ID NO 35
<211> LENGTH: 320
<212> TYPE: DNA
<213> ORGANISM: Rattus norvegicus
<220> FEATURE:
<221> NAME/KEY: misc_feature
<222> LOCATION: 1- 320
<223> OTHER INFORMATION: n = g, a, c or t(u)

<400> SEQUENCE: 35

| | |
|---|---|
| tatgcaccca tgacacaaga tcacagaagt acaggcctgg accatggcag agtatacact | 60 |
| ggttgggtaa atgaagagga gagacagagt gggaagtcgg cttagtggat atggacttca | 120 |
| aatttgatga acaagcaatt caaatgagta tcgtgggctt gactggtatg aagacccgtt | 180 |
| tgcaaagcag tgntcataag agagaaaaga gagagagaga gagagagaga gagagagaga | 240 |
| gagaaagaga gagagtgtgt gttgttgttg ttgttgttgt tgtttattgg tttataacaa | 300 |
| gatntacntt tggtaacttt | 320 |

<210> SEQ ID NO 36
<211> LENGTH: 389
<212> TYPE: DNA
<213> ORGANISM: Rattus norvegicus
<220> FEATURE:
<221> NAME/KEY: misc_feature
<222> LOCATION: 1- 389
<223> OTHER INFORMATION: n = g, a, c or t(u)

<400> SEQUENCE: 36

| | |
|---|---|
| ggggggggngc naaaagggtc tttcttttna naaaaatcnn ggangaggc cncnanacgg | 60 |
| ctnttanann tnttcngggt gtnccctcncc gntgtgggga atganatntc gntctcgaca | 120 |
| tcagggatt ggagattntc tgngctcncc nctcacnacc cagaagaagc gcacagagan | 180 |
| cagagtanca catctatacac acctnttcag ctacagagcg antnctctan aaggggactc | 240 |
| gggggganaac acaaccctcc tcctcttctg actgngagng ccgcntgtag gntctgtcta | 300 |
| cccancaagn cttgtgcagn ntgngaacct ctcntgggg tagagtgtgt tgnggagca | 360 |
| gggcgtantg ttccaggnct agnctttca | 389 |

<210> SEQ ID NO 37
<211> LENGTH: 882
<212> TYPE: DNA
<213> ORGANISM: Rattus norvegicus
<220> FEATURE:
<221> NAME/KEY: misc_feature
<222> LOCATION: 1- 882
<223> OTHER INFORMATION: n = g, a, c or t(u)

<400> SEQUENCE: 37

| | |
|---|---|
| agnaacgcgg ncggnggnnc tcncccngcg gagcnggncc ncccccnngn ncccagaana | 60 |
| gnagcgctcg gngannnccc acgngnagac nnnggctgcc ccncgngncc anggcnttnn | 120 |
| nccnncccc cgnatccggn ncncccccc ctccctnggg gngcgggggt cccngngccg | 180 |
| nggngatacc nggcgannen ttgtgccccc gcnnggggg naggacccc ggcaccggcc | 240 |
| cngacccana ncagnngctt ngtggggggc ccccccgcca nagaacgaat tncgccnccg | 300 |
| gccgcggcca tcggaacncn cctagcagng cgtcntgcta ggcnggnnna cgggnatccg | 360 |
| caancccncc cttngtaccg ggacagccgn gggnccgtat gggctgngcg ntnggccgta | 420 |
| gccanntncc tttngaaang acnggnagc tnttcatccg cctcacaaac cncgggncn | 480 |
| gnggggctn tntcntgngc cgcccgccgc gtgngcgcan aaaaaaaaa aanncggccn | 540 |
| tccnccccct ttttggccng ggtncccgc ncacccgtg ccgagtnccn nnccccac | 600 |
| aacctcacac cgatcccngt gggttcccnn ngggagtcgc ncgngcnnag cnggnttctc | 660 |
| cccatnncgc gnngcttnag cgngccnnnn cacngtttgt nngngnntgc ctcccctncn | 720 |
| tccttgaggc aaaagcccgn acngtntctg tggaccacnn tgctgaggng ctgggcgccn | 780 |
| cgntctctct ctctctcnct ctctctctct ctctatctct ctttctctct ctggggcccc | 840 |
| tcccttgntg nngccanaag nnngcnnacc cgtaaagtaa gt | 882 |

<210> SEQ ID NO 38
<211> LENGTH: 975
<212> TYPE: DNA
<213> ORGANISM: Rattus norvegicus
<220> FEATURE:
<221> NAME/KEY: misc_feature
<222> LOCATION: 1- 975
<223> OTHER INFORMATION: n = g, a, c or t(u)

<400> SEQUENCE: 38

| | | | | | |
|---|---|---|---|---|---|
| aatttngnca | ataanggccc | ttccccctgag | tgnggggganc | ncncntgttc | anaaggtacg | 60 |
| tttagcgngg | ttctcnagtt | natggtaacc | nagtacttaa | ttggcncnct | tgataaatgc | 120 |
| tngatcctna | naatttcaac | aaccgcagga | ccatttttga | acttggcggn | ngtttaccct | 180 |
| tnatgnnctt | tccnnaaaat | ggcttccttt | gncatcnaat | agtgntgccc | ctaaccccctn | 240 |
| ggttccggag | gatgcatnng | tggntgtgng | tttgnccttg | agcatgcngt | tccgtnacgg | 300 |
| gancaagntt | ntcaatgttc | cntcacncca | tacttnggct | tggggtacaa | nttgtatatc | 360 |
| ttcgggatta | tatnagttta | tgtctgnttt | tcataaaatc | acttgtggat | ttggctttaa | 420 |
| ngttaggaca | acttnccaca | gtttcttgga | tctccntcaa | catgttaacg | ccatttttgtt | 480 |
| cttgtatact | aaagtgacat | gtcnttntng | acactaacaa | tcacaaatta | ggagtaccaa | 540 |
| tcaactttga | gaaaatttaa | aagatgcccc | atctcttgta | tcagcaagta | ttcagccagg | 600 |
| atttaattct | ttatgtaaaa | attagcaagc | atttctatnt | cattcacgtg | caaatttttct | 660 |
| ttgattgtta | attaagattg | aagtgatatg | tatggcccaa | ataagtctca | ctttaaaaaa | 720 |
| tatttctttta | tgaattatta | tccatgaatg | tttgatctgt | atagctattt | tatataagta | 780 |
| tatgcaagga | ttgctaaaac | aattttttgag | tgaaaaaaga | tcctaggtag | aaaatgttta | 840 |
| agactaccta | taccgtcatt | aaaaactcct | caccagcatt | tactatggtt | ggactttcag | 900 |
| agatctcaat | caactctttc | ccacccagtc | tactgaaagn | ttccacctgt | agcggcccaa | 960 |
| gcaaactgag | atntt | | | | | 975 |

<210> SEQ ID NO 39
<211> LENGTH: 850
<212> TYPE: DNA
<213> ORGANISM: Rattus norvegicus
<220> FEATURE:
<221> NAME/KEY: misc_feature
<222> LOCATION: 1- 850
<223> OTHER INFORMATION: n = g, a, c or t(u)

<400> SEQUENCE: 39

| | | | | | |
|---|---|---|---|---|---|
| ggggaaaccc | acggtnaagg | gnnggananac | naggtanctn | tttctccggg | ttccaanaat | 60 |
| ngaangcctt | ccngagggcc | ngaaaancat | tncttcngga | gccgttcaag | ccagnaggtg | 120 |
| ggtttcaaac | aatgcttaag | ttgtgggggag | aacnagncag | tccgttccng | acccngttta | 180 |
| tcntaaagga | gacggnggtt | aaaggttagg | gggttngaca | gtcctgctgg | tgttcaagga | 240 |
| ggaggagaca | agttgncatc | caggngngca | ggaanacctg | ttaaattcct | gaccnaccgg | 300 |
| atgnttggag | agcnaaggcg | gattcttccg | gcagtggcca | gatttcaacc | caggtcccgc | 360 |
| ccngcttttc | ttggttaggc | aagcaggcct | tagtccgnga | ggacgcccct | tggtggccag | 420 |
| ggtatcacgg | cccccctngg | gtttccattt | gcagtttgta | ttggaccatg | gatcactgct | 480 |
| tccttntgcc | ggaagttcca | gattccaaac | tgtgngantc | ccatntgcaa | ctcccatgtt | 540 |
| tgccgntggg | acttttttnta | atatcntggt | acccgcttcc | catttcccca | ccccncntgnt | 600 |

| | |
|---|---|
| cccttcggga ggaatcaccg cccagtgtgt cacttcctgt aggnacttcc aaggntagat | 660 |
| gagtgagtgg caggcctcac nttggcccag ttantcagtg cccacagagt agctttttg | 720 |
| agacgntagt aaggtcttag gggaaggaat gtagtcgatc cttctccttg gtggccctca | 780 |
| gcactgtgag tagaccccac acatcagggc tgtgtcgtta ggatctctgg gagggttgaa | 840 |
| agtttcgagg | 850 |

<210> SEQ ID NO 40
<211> LENGTH: 889
<212> TYPE: DNA
<213> ORGANISM: Rattus norvegicus
<220> FEATURE:
<221> NAME/KEY: misc_feature
<222> LOCATION: 1- 889
<223> OTHER INFORMATION: n = g, a, c or t(u)

<400> SEQUENCE: 40

| | |
|---|---|
| ggggtttcca aaaatttggg gntttggana aaccttcggg gaataaaaca acngnnnaaa | 60 |
| attaaggggg gccggggggaa aaaggagatt nattaaancn ccacccgaat tnaaacnccc | 120 |
| nccgggaccg naaccgtttt tggccnaaan ncgagaagtg ccttccnggc aaagtagggg | 180 |
| accaaaggtn gggggagaga attggggttt gtncagngtt ccggttcnac ggaaggagcc | 240 |
| ggttgttggg attgtttcca aggagngngt ttgngaccgg agcacctcng gggngaccat | 300 |
| ggggnttgcc tgttagagac cngcgngatg ttttgggttc gnattcgggg agggatttcg | 360 |
| ggggcctcag acngggggagg agtcccntgc gttcccnatg ggaccggttg tcgggcgggt | 420 |
| gcagtttcgc tgctgtcctt tggcaatgng cntgggnatt ngtgggcaga ngagattccc | 480 |
| cngccccgc natttcccn gttccagttc ntaggnacca gaggttttcc gcagtgtgat | 540 |
| tcagggagnt agantntagc gtctgtnttn tntgcgtttt ccccttcatg attctcagtt | 600 |
| atttttagg agaaaggtg cgtggaaaca gagcgtccct gttccgtgct gtttctcnta | 660 |
| gcccaaaata cagatttaat tctgaagcca tcgaccccca tatccacttc ccgccctctc | 720 |
| ataaacgtgt aatatggctt gcttttctcct tgtaacgttt catccaacca tagtggtagc | 780 |
| ggccacctgg catcttgagg tgggttgcga atgagtgaat gaatgagtga gtgaatgaat | 840 |
| gaatgaatga atgaatgaag caagcttcag ggagattttc agagaagtg | 889 |

<210> SEQ ID NO 41
<211> LENGTH: 929
<212> TYPE: DNA
<213> ORGANISM: Rattus norvegicus
<220> FEATURE:
<221> NAME/KEY: misc_feature
<222> LOCATION: 1- 929
<223> OTHER INFORMATION: n = g, a, c or t(u)

<400> SEQUENCE: 41

| | |
|---|---|
| aatgcccntn agggnnttt ccccgnattt naaaatgggn tncnngnttc caaagtttcc | 60 |
| taaaaatttn cantttccgt ttttaccngg tttatggttt ncagcctact cctgttcgan | 120 |
| ttccaaatcg gtttaantgg ncccnccgaa ncnttntttn tttggcagaa ggtgaanttc | 180 |
| nttggggccc ttgtttaagg gttttnagcc ttaaattgnt tgntnagnnt ctccntaatt | 240 |
| agttcattcc tttgaccatc ttttgnccct ccatcttgta aacanttaag tctattgcat | 300 |
| tccactttnc tntcagttnc cgtttnaccc tcctnagcag aaccgnttc tcagctntgg | 360 |
| atggttccaa anggtttccc aacctatgct caataccaca gcagcttgc aggagggaga | 420 |
| antggtatgt atttaacagc attttgaccc aaactttag gagcagagag gactttaccc | 480 |

-continued

```
aggacaggaa ggcaaaagac ttgaatctta acaaaggat taagaacagg atgtcatctg      540
tgagcctgtc acagtgggtt tgcagagcag gagaacacag acaggattag ctataaagtt      600
gttacattag ttattntatt ggagcataca atacttaaat agttctaggg caagagaaat      660
gaacagaaat gaccttataa gagccagagc tgtagccaca gctttctttg tgcttagttt      720
gctagttcac tctttccagg gcagtctggt ggattacacc aaattgctta gaaaatgcta      780
gctctactgt ccctgtctat tgtcagcttt gcaatgtgca tagtgacagg agttgcctgg      840
gaagcttggg gcttatgttt tgcagatcca ttgtaattaa aaaagaattg taaggagatg      900
gaggcacggg gtgagggtga gggtgagtg                                        929
```

<210> SEQ ID NO 42
<211> LENGTH: 943
<212> TYPE: DNA
<213> ORGANISM: Rattus norvegicus
<220> FEATURE:
<221> NAME/KEY: misc_feature
<222> LOCATION: 1- 943
<223> OTHER INFORMATION: n = g, a, c or t(u)

<400> SEQUENCE: 42

```
ttggaaaccc caacctggaa aangngtntt nccgggaaat tcaacctgcg ggcnaatggt       60 gtaaagggc ctaccttggc ttngaaggga atntcctgaa ggnnnaatcc caannttgtg      120
natcccaatt aaggntnaac nggtttaatt tgtnntccnc ntaccnaccn ggtttnccgt      180
tatactaaag ggctaacaat taaatgctca naagggaccc ccaatcctng gcnagaactt      240
gggttaaggn ttccattagg atttgccatc ctntaccgtg atcctgaaca tntnttgaac      300
tgntttgcca aggaacngaa ggttttncct naagntagca cacagcagng accaaggatt      360
ggaacccagc nagtgcttgg aggtaaaaga tcacttcctn ntcccttagt caggancntt      420
agggagtgga ggcatcaccc acacattccc cagtttgnac gtaggtttca gccagcaanc      480
cgtccactaa agctgcctcc aattcaaact ggattgagtg acaagtggct tgggtgtctc      540
tcaaagattt ataggtggca atggccactc ctctgtgtaa ttaccctnta tgcacgtctt      600
tttnttctct cccactccat cccccacccc tctttgtttc ttcntccntt cctntccctc      660
ctgttgactt tttctctccc tgcaaacagt tccaggcacc gnttagcatn tgccactctg      720
gctntagaaa gctttgcttc ccctctgctc cctggctggc tggaactcag cctccggtgt      780
gggcagactg gctcatcctc tgtgtttctc tgagtgtgga ctgctgcctt ccacacagac      840
tctctgaagt caaggagccg caccagcact tcagttgtgg gccataatca agncangact      900
gaaagttgcc acctgtagng gccgcaagca aactgagatn ttg                        943
```

<210> SEQ ID NO 43
<211> LENGTH: 867
<212> TYPE: DNA
<213> ORGANISM: Rattus norvegicus
<220> FEATURE:
<221> NAME/KEY: misc_feature
<222> LOCATION: 1- 867
<223> OTHER INFORMATION: n = g, a, c or t(u)

<400> SEQUENCE: 43

```
aggaaaccnt tttaaaaaaa aggggggggg ggggggggn ntagnggcaa aaaagatgan       60
accctcaagn cgggggggt taaanaagga atcggattcg ggctttgnac aaataaagga      120
gttttgngng nattttcccc ntggtcgttt tntgnacgat ccacggttga ccgacgacgn      180
```

-continued

| | |
|---|---|
| acggaccgac aaccaanacg taaaggggaa ttgtggaggg gttggaagtt tagatgcccc | 240 |
| gacccaggac gtgcggccan cttccggaga cccacctttc ttgtnggccg ggnccggcgg | 300 |
| cagcgnagcc atttccaccg gatccctata gcnggccagc ctagcaggcn gaacaccagc | 360 |
| gggaagttga ntnggacctc ggagagcgcc cgcccttccg gcggaagtnc taattccaaa | 420 |
| gcggcccgcg gcngagtttc ccatacaggt tggttccgtc tcggagtgac gtggcttgaa | 480 |
| ggacggtctt cgcgcgagaa gagtaccctg cctttcaggt gcgggagtta cntcagcctg | 540 |
| ctgcacaccc ggctgtgcgc antcttctgg tgtggccggg acggttcacc cagaggagtc | 600 |
| tctgtagttc ggagcaagat gtcggttaaa tctggcagga aaatgccttc tatgctcatn | 660 |
| tatatattcc tgcttccctc agcttgcttt cgacttagta aggtaacatt tcagagcggt | 720 |
| gcacttagta cttttggca ctgtgctgta aaatataaa tgttccacac ttaacatctt | 780 |
| agatgttata tctaaagata tgcatcttta aacttcgaaa gcgcataccc taaaatttca | 840 |
| tattttgca tacattggtc agctgtg | 867 |

<210> SEQ ID NO 44
<211> LENGTH: 303
<212> TYPE: DNA
<213> ORGANISM: Rattus norvegicus
<220> FEATURE:
<221> NAME/KEY: misc_feature
<222> LOCATION: 1- 303
<223> OTHER INFORMATION: n = g, a, c or t(u)

<400> SEQUENCE: 44

| | |
|---|---|
| ggaaatgatt agtccaagaa atatttgagc agaagggagt tagggttttc aaattaggaa | 60 |
| agtggaatcc acagagttcc cttgacagag aatataaaaa ggactctggg gtgtcagaat | 120 |
| ggtgggcatt aacctgatct tccacttgag ggtaagggaa atgattagtc caagaaatat | 180 |
| ttgagcagaa gggagttagg gttttcaaat taggaaagtg gaatccacag agttcccttg | 240 |
| acagagaata taaaaaggac tctggggtgt cagaatggtg gcattaacc tgatcttcca | 300 |
| ctt | 303 |

<210> SEQ ID NO 45
<211> LENGTH: 840
<212> TYPE: DNA
<213> ORGANISM: Rattus norvegicus
<220> FEATURE:
<221> NAME/KEY: misc_feature
<222> LOCATION: 1- 840
<223> OTHER INFORMATION: n = g, a, c or t(u)

<400> SEQUENCE: 45

| | |
|---|---|
| aaaccggnng aanaaaaaan gaaanngang gcnnnaaaaa agttnngaca gaaaaaactt | 60 |
| tngaaaaaa gganggggan aaggcaggng nccnactnaa aanggnctt tcnaagngng | 120 |
| anagagntgg naatnagnaa naggacattc ttnnaacctc cnanggnggn nggaannaat | 180 |
| ngggattgag cngccaccat tagggangaa gttngaattn ngggccccgn gngagttaaa | 240 |
| angattcccn ggttttttaa aacagagaat acctncaggn acagatnaac ccgagattgg | 300 |
| ttccctngaa aattnnngan aaagataaan gtaggagcat tcaaagtagn anggtaaaan | 360 |
| taatgggaga catagacacc aaaaaaagcc agttcagtgg gccccgaagg ngcattaagg | 420 |
| gaggaccagg aaacggcagc anagccacng gcagccgcct gccccnacac cagtnattcc | 480 |
| cgcacntaga tccaggcgnt gggggcgggg cggggcgcgc ntgngcagng aagntnngcg | 540 |
| gcaacaantt tgcntagacc ggntggaacc ggttagaacc ggccgcgccg gaccggccgc | 600 |

-continued

```
ccgttccgga ttntgcgttc acaaagggag gcgggactca cgacntgngt atcnttgngg      660
tcccaacccc ggccccnac cccnaccccc nttgtccctg tggcattcgc gttctttccg      720
ccgtctccct cgcgggccgn ttntctgcgc ctggtgatcc tttcgccatg gtcctntgga      780
gaaagaaaaa atctttaatt tnctagggac gtccttttcc tgtagtcgta attgtagaaa      840
```

<210> SEQ ID NO 46
<211> LENGTH: 893
<212> TYPE: DNA
<213> ORGANISM: Rattus norvegicus
<220> FEATURE:
<221> NAME/KEY: misc_feature
<222> LOCATION: 1- 893
<223> OTHER INFORMATION: n = g, a, c or t(u)

<400> SEQUENCE: 46

```
gagaaggann aggngggggng agngaagana gaggagggaa gaaangaagg tggaganaag      60
tggannaaaa agagggagan ggagggagaa ntaaaganag ganaagagng gggaggaggg      120
gnagnatagg agaggaaaga aagganggan agaagagaaa agaanganga gagaaaggaa      180
agaggaaaga aagaggggag aagaggaaga aanagaggag gggangagag ggaggataag      240
agaggaaaga gggaganagg nttgaaaagg gaaagagaag gagaaaggna gnaggngngg      300
aagagaggna agggagaggg gganaanggt aagggggnaa agaangagaa gtatnggggg      360
aaaggaggag angaaagaag aaagaganga ggaggagagg gagagtgagg aataaagggg      420
agggaaaagg angagaaaga gagagaggga gagggaagaa nagagaagga tagnggggtg      480
gagaaggaga aaggagagaa ggagaaggng agaggagaan tgaagaagga gggagtaaga      540
aaggantgag naggaaagga ganagagagg tagagagaaa anaaagaggg aaanggaggg      600
gaggagggng nanaaggaat agagggngga aanangagag aggggaaaang gggaaggaaa      660 ggaggaaaaa aagnagagaa gaagagnaat gggaaggang nagtagnaaa agaaaagnag      720 agggagagg gggangangg gggganacggg ggggaanaga aaaagtgaag gaggcccccc      780 naccccccc ccccacacac acacacagcc ttttcgccgg cggaagtgca ggttggtcca      840
ggagcctgtg gtcaatccag tcagtagtgg gcgaggtgta acatctgtgt ccg            893
```

<210> SEQ ID NO 47
<211> LENGTH: 789
<212> TYPE: DNA
<213> ORGANISM: Rattus norvegicus
<220> FEATURE:
<221> NAME/KEY: misc_feature
<222> LOCATION: 1- 789
<223> OTHER INFORMATION: n = g, a, c or t(u)

<400> SEQUENCE: 47

```
taaaananng gnngannanc tnnaaaaaan tntcttngga attnncagga nggaggntaa      60
tngggcgggc ancatcaatg gtanaaattt ggggggggnng annaaaatca tnaanncaac      120 cgttttccana gncaaccatt ctgggngncc caaggttnga ngagntccgn tcaaggngaa      180 acctttttcaa gaccaattaa ctaggggatn agaggcgggn tggttnntga ggggcgggct      240
gctgagaaga ttcgttgggg gacccaggag tgaaggtttt tnacctgtgt ntntcgggaa      300
ggtcggatnt attatantcc tgctgttgga ggagttcggt ggttcaaggg ccggacccgg      360
agcgtttact ttttnttgnc cgcagccaat ttgttntgct tggtttcttc ngaatcccgg      420 ggcgggggagg gggaagcggg gggcccaatc accacgatcc cggcagccac cgcgaaattg      480
```

```
ttccggcagn tacgantctt caacaagagc cagagaaggc gggtgcagag nttcattagg      540
acgntcggaa acccggcgtg acttactttn tccaagccca ttggttgatg agaatgatga      600
ctgacaggga ggcgtggtca cgctgtcgcg ggcgggagcg acgggtggag ttaacgacga      660
aagctgcgcg cgcagccatg acccctcaca gccacntatc ggagggaggg gcgggacagc      720
tttagcttgg tgcgtgcgca gccggacgtg aggcagttgg tggtcttcca tcgtcgattt      780
ctggttacc                                                             789
```

<210> SEQ ID NO 48
<211> LENGTH: 872
<212> TYPE: DNA
<213> ORGANISM: Rattus norvegicus
<220> FEATURE:
<221> NAME/KEY: misc_feature
<222> LOCATION: 1- 872
<223> OTHER INFORMATION: n = g, a, c or t(u)

<400> SEQUENCE: 48

```
gggggnggct tttttnggag gcatanatng gggnnngtcc ggnaaacccc attggtcggc       60
cggggaagga aaangggggct ctnaaaatan gttantggga tggngcctta agggggggcc     120
catgngccag gaangcagat tcaaaaatgt tccaagtgga aaaccanggt tggnanaggc      180
cctccnggnc gtnaaggagg agaggagaga tggagtttca ggtgtgtttc ccacccagtg      240
ttcccaggga acacaaaacg dataggtcac cntcaatgna caaggaatta aaagcttggg      300
tgtatnggga ggcctgcttc caaagccacc agaaaatccg gagagccggn ggatcntacn      360
cacccagagg ttcataggga gggcantatt agggtgtgc ccttgtgaga ggaagtgtgg      420
cacngtgggg ctgggtttga gatntcagat gntcaagcca ggcccattnt ntctctctca      480
gtntctctcg gtctctttct cngtctctnt tcagtctntt cagtctctct cagactctct      540
ctctctctct ctctctctnt ctctctctct ctctctctct ctctcccngc tgcnttcaga      600
tatagacgta gaantctcnt ntatccagca ccatgtctgc ntgcatgctg ccattnttcc      660
caccangacg ataataggct aaacttntga actctaagcc agcctcaatt aaatttntan      720
gagtcaaacc agcctcaatt aaatgttttc atttctatga gtcacagtgg tcatggcatt      780
tctttacagc aatagaaacc ctaactaaga cttgccgaaa cctcaaccac aacttcagcc      840
ctcagaagcc caagagggaa aagaccttga at                                    872
```

<210> SEQ ID NO 49
<211> LENGTH: 785
<212> TYPE: DNA
<213> ORGANISM: Rattus norvegicus
<220> FEATURE:
<221> NAME/KEY: misc_feature
<222> LOCATION: 1- 785
<223> OTHER INFORMATION: n = g, a, c or t(u)

<400> SEQUENCE: 49

```
tcgtaanttt tnatccaccn gtanangatn ttccatgcca ccatgtacgg ttacgaggng       60
tatagcgtgn acngttttgg agtgngctaa aaggaaatgg agacntattg tnttggtttt      120
gtgacccata acttcggaaa ggttgtgttt tatccggcaa caaccacngt gtagcggtgt      180
tttttgtttg cagcagcaga taacgcgcag aaaaaggatn tcaggagatc ctttgatttt      240
ttnttcgggt tctgacgntc atgttgtgtg gaattgtgag cggataacaa tttcacacag      300
aattcaaagg agaggagcca atatagaggg ggaaaaaaaa agaagggaa agcattagtt      360 taaaaagttg agagaacaaa gtatgttttg cttggatggg caaccaaaga agcntgccag      420
```

```
gaatggtcgg taaaaggtgt aagagtcatg aaacgtcttc tgtccaaccg ttaccggaaa      480
catgcaagga atttcttaga ctggccagga ttggattgtg ggaaaggtct cttcaagcnt      540 cccttggct tttatggcaa gaaaatagtg cggactatag agagcgtcgt tctcaaagct       600
tgtccccaat agcagaaaag cattgtccta aattccttaa aaggcaccgt gaaataaata      660
ttacgaggac acgatggcac aagaaggagc tttcaactct gccaccagaa cagttatact     720
tcatagtaac catgttgccc tgttcaatga caaggcacgc tctccagcag aaagggaaaa    780
ggagc                                                                  785
```

```
<210> SEQ ID NO 50
<211> LENGTH: 889
<212> TYPE: DNA
<213> ORGANISM: Rattus norvegicus
<220> FEATURE:
<221> NAME/KEY: misc_feature
<222> LOCATION: 1- 889
<223> OTHER INFORMATION: n = g, a, c or t(u)

<400> SEQUENCE: 50
```

```
nttnnaaagc ganccggccn gggnggtttg gncggcgctt tatacnaagn cgngccaatn      60
ggctttgggn gggntttcat anggnnntgn tttacccaat tcagtttttt attggtnttt    120
natgggcgca gggatagngn gttcnggntt cccacangaa tttgatttnt ggaatcacaa    180
gtnaccagtn gccgnaatca cgagtttgcc gctttntttc ctaccttana ttcataatan   240
gaatgagtan tttttttta ttgagnaang ttttnacagg tttagtaaac atgaggacag    300
aggttttaag ttgangatta ggaaggagag ttccggggga cagaatgtgt gtattntcag    360
tcagtgcact acccggaaga gttgcagtca ggttgaggaa gggagcggat ttcctggagg   420
ttttaaccaa cagagagaaa aagcatttac tactgattaa gcacacaatc tctggattca   480
gagaagggtg tttaccttta tataaaatgt ctcctaactg cgtgactgtg tgactttgtt    540
gaagtcaact gagcactgac tgtgttgtgt gcaacatggt aagaggacca acttntttct   600
taaattttat ttattattta tgtcacgtgn acacttgttg ctttttgtttt tgttctaatt   660 ttatctgcat atatgtctgc ataccacgtg catttctgat gcntacagat gccagaaaag  720
gacaccgagt ttccctggg antggagtta tagatggtta taagtctctg agtaggtact     780
gggaagtgaa cttcagtttc ctctggaagg gcagaaagcg cttttcaaat gctgggccat   840
gtatttcagc ccctacttaa tttataattt tattttagag gatgtgctc                889
```

```
<210> SEQ ID NO 51
<211> LENGTH: 947
<212> TYPE: DNA
<213> ORGANISM: Rattus norvegicus
<220> FEATURE:
<221> NAME/KEY: misc_feature
<222> LOCATION: 1- 947
<223> OTHER INFORMATION: n = g, a, c or t(u)

<400> SEQUENCE: 51
```

```
anaaaaatng agaagangag accccagaga agaagnanga gaganaacag agaagaagag      60
agnaagggng anaaantaga gaaaggaaaa gntcttaaag aggcnanaaa ntancnatnn    120
aaggagaaga nggaaggnta acataggagn caagaatana aaganaaaaa gaggtagaga   180
anncagagaa cgagaaaaga tgaaanaaag antanaaangg aagaaagang nccagnanaa  240
anaaggcaga aanaagatgn cgtaaaaaaa gagagaagat aggnaaaata gaggagaagg   300
```

-continued

| | |
|---|---|
| ccnaacagga ngggaagagc agcgaattnn agataaaacc ggagganagn nagagaaggn | 360 |
| agagntngnn aaggcaaaga cagnanngag nacggtacnt gccccagaag gnngaagaan | 420 |
| gncnagangg tgagggnngg cacngnccnt tccccttagg aggncgcccg cccagagatc | 480 |
| aggtttcnag gncaccgagt tggatacnag attatncacc naggcaggaa angantatng | 540 |
| caaaangatt cggggnggg tcacgggtg agaaataaan tcannaaana gaggacgngg | 600 |
| aggagggngg gaaactctng acagaaatng caagcangaa gccagccnca cccaagcccc | 660 |
| nacngaagca gcngagangt tgcanggcgg naggtccaaa tcancgnagt catggagnga | 720 |
| gcttcgggng ggcccnganc cantgaggaa gggcaggaaa ccatatcnag ccgagccnng | 780 |
| nganggntgc cctganacac ccggagaggt aattttatt tnacgggaag cgtccagnca | 840 |
| agttcgtggg ccgaagagaa cggtacttta gtatacancg ctnntgctnc gagttgtnng | 900 |
| nccttntnat gnnagatctc acaaangaag ctnanaagta gatatgt | 947 |

<210> SEQ ID NO 52
<211> LENGTH: 860
<212> TYPE: DNA
<213> ORGANISM: Rattus norvegicus
<220> FEATURE:
<221> NAME/KEY: misc_feature
<222> LOCATION: 1- 860
<223> OTHER INFORMATION: n = g, a, c or t(u)

<400> SEQUENCE: 52

| | |
|---|---|
| aagggaattt ttaccccggt tnccttttgn cnggggggna aaaaaannaa aaaataattt | 60 |
| tttaaaatta aagggngggg angtttttcc ggttctattn ngccnattcg gggttacact | 120 |
| tttatccanc ntttgntttt ttanccggcc gggttaaaaa tgggggggga ttagttcggg | 180 |
| taggngttnc cnacagcaca gccctgtttn tcttcgttcc ngaaaaaaaa aaattttgct | 240 |
| ggtntcacaa ttttnttaaa caggatttnc ttcaaccatg gattaataca tttccggtgc | 300 |
| agnttgcccg gtttgttttt tggntggata gggatgccag caggattcag ggatgcccat | 360 |
| tgtgnttagt ntctggccct ttaggagagc tttgggctaa ttatgtgacc gattttaaga | 420 |
| agtggtgttg ttgtggttcc agggactcac ggatcagcct ttattttata aggacactgt | 480 |
| ggaggagaga cagaggctga gctgcattct gatgtcattt gtgctgctgt ggaagttaaa | 540 |
| gaaaagctgc agaagtcagc aaaacagatg aataccaaga agggcagtgt gagtacagga | 600 |
| atggagagaa aagtcagagt ccagctttgg ttaactccct aggatcagac anttctgcgt | 660 |
| aaggacgggt ctacagttta acagaccaca gagcaangtc aaacagcaaa gtggtttcat | 720 |
| ggcaggcagg aaatgaaaca tttaactgga aacactgaac ccacccatgg caaacttagc | 780 |
| aatgaagctg ggtgtggtgg cacatgcctt taattccaac actcagggga cagatntaat | 840 |
| gagtttgagg ctagactggt | 860 |

<210> SEQ ID NO 53
<211> LENGTH: 191
<212> TYPE: DNA
<213> ORGANISM: Rattus norvegicus
<220> FEATURE:
<221> NAME/KEY: misc_feature
<222> LOCATION: 1- 191
<223> OTHER INFORMATION: n = g, a, c or t(u)

<400> SEQUENCE: 53

| | |
|---|---|
| aggtctgacc acttggaagc ttgccctgan tcatagatga gccactgtct tcttcccctc | 60 |
| aattcctcag gatggggaac agccattggg cttttagtag aggagggaca ggcccttttg | 120 |

| | |
|---|---|
| cagcaacagt tctcccctga atgttggatc tccacctata cacatgggt acttagcctt | 180 |
| atggatgccc c | 191 |

<210> SEQ ID NO 54
<211> LENGTH: 988
<212> TYPE: DNA
<213> ORGANISM: Rattus norvegicus
<220> FEATURE:
<221> NAME/KEY: misc_feature
<222> LOCATION: 1- 988
<223> OTHER INFORMATION: n = g, a, c or t(u)

<400> SEQUENCE: 54

| | |
|---|---|
| ttnttggnna cgggtntccg nantatgaan ccnttcccgg ggttttttaaa aancccngga | 60 |
| tattcgggga tttgggtttt nnacggcctt tttttnagag gccaaatncc cntntnaang | 120 |
| ccttttatcc ttccntttnt gccccncttc naattaggaa gcntggtttg nccgantntt | 180 |
| aaggttttta gtcntccttc gttnntnttt cccttntttt ttccctnaag ttataaagcn | 240 |
| ggtatntggt ttgccaggnt tctnttgtac ccgtcatngc gggttncggn ttacccaggn | 300 |
| tttgttcctn ggccggtncc ttccaatttt ggantntccn ggtcnggngt ccnattncct | 360 |
| tgnaacngtt ccacacntna tgacaattaa ttgtttcctg tgtaatttgt ccccggactt | 420 |
| ntggattctt gngancaggg cctntgtttc atggaagcaa actcccttaa ntatttacca | 480 |
| ggttgattga ttaagaaagt antcatgntt gggaaaccca cntgttttnt tcccaggatg | 540 |
| gaancccagg attttggaac tgcagaggct tcagggtctg ggaagcggag gcaggcaaag | 600 |
| aatggagtgc actgtccttt tgcaatatgg ggtttgcctg cctgctggct cctctcntgc | 660 |
| tntctcagat ggtgactgag gctacttcag caggactagg aataatcatg tccaggtggc | 720 |
| tgcccttccg agcagaaagg gacagacgtg gggcgatgaa gttgctatcg tttttttttt | 780 |
| tttctgcaca gactgcaaag tgtgcagagg gagggaggc gtgcaaaaaa aaaaaaaaaa | 840 |
| aaaaaaaaaa aaaaaaccga ggacgcagaa gttagactgc tgacccattt ggtgcatgtg | 900 |
| tgcccatgga gggagggac cttctcaaaa gggttcacgc agcangcatt gaaagtnccc | 960 |
| cacntgtagg gncgcaagca actgagat | 988 |

<210> SEQ ID NO 55
<211> LENGTH: 665
<212> TYPE: DNA
<213> ORGANISM: Rattus norvegicus
<220> FEATURE:
<221> NAME/KEY: misc_feature
<222> LOCATION: 1- 665
<223> OTHER INFORMATION: n = g, a, c or t(u)

<400> SEQUENCE: 55

| | |
|---|---|
| gaaaaagatt caggaanctt attttntcg gttcgacttc agtngggaa tgggcggana | 60 |
| catttcacac ggatttgtaa anacngtnac ngaaacttgg nggttcgtag atccacttt | 120 |
| ttnagacctg agagtagttt ttaaaatatt tnaattaaag gtttcctgca cccacttttt | 180 |
| tttttatccc taacttttca tccagtatgg tttttcaata tcacantttta atctaggact | 240 |
| ccttgcttaa agcaattaca agttaaatta aaagtaagag atggctnata gctctcatta | 300 |
| ctgggatgca ggtgtgaaac aagtgatttg tgtagaagct ggcaggatgg gtataaacaa | 360 |
| gaacacgtgc ccagaggatg tattgaaagt tggatttaag tctctgagta gtttatgcta | 420 |
| ggcggtagca ttgaacaaga tgaantctct gntcatagag gtagaaactn cccagattct | 480 |

| | |
|---|---|
| gaggaagtgt gagggagagc attagatgtt actgttgggg atttgggaag gccaggaaac | 540 |
| gttactccat gcccaaggag ggtaggagaa aggtttgggc ttagctttga ggacggaggg | 600 |
| aactggtggg tggatatgag gatggttatg ctaaaagcag agtggttttc aactattgtt | 660 |
| cttct | 665 |

<210> SEQ ID NO 56
<211> LENGTH: 857
<212> TYPE: DNA
<213> ORGANISM: Rattus norvegicus
<220> FEATURE:
<221> NAME/KEY: misc_feature
<222> LOCATION: 1- 857
<223> OTHER INFORMATION: n = g, a, c or t(u)

<400> SEQUENCE: 56

| | |
|---|---|
| aaaaaaagaa aggaaggggg agananaaaa annangngan aaaanagana ganagaggna | 60 |
| agaggaagng agggngaaaa gagaggagan aaanaagagg aaggagaann gaggaaaang | 120 |
| aaaggaacaa aaganaagng anggaagana aagggagaaa aaanaagagg gagaaangga | 180 |
| ggagggaaan agagaagaga gggggagaga anncagagaa nagaanngag aaaaggngga | 240 |
| gacnaanana gagggaagaa aagngaggag aagagagggg agaanaaaant tgaagaagaa | 300 |
| gaagangaga agangagnag aggaagagna ggggaagaag aagaggngga ggagaagaag | 360 |
| aggagaggag gaggaaggag aaggaggagg aagagaagga ggaggaagag gagaggagaa | 420 |
| ggaggaggat actanggagg ttgtttcaat aaaagagngg gatntaagat taananaagn | 480 |
| aataatgccg gtttntatct gttcgggggg ggtccttgtt ctccaaacac aganntgggc | 540 |
| cagtttntca aaattnaant gngaagattt cttggntnga gagcagntca gattnantng | 600 |
| nattntttc tagttttnaa cacaanctttt gtgntaacaa agagnganga ttcnaggana | 660 |
| actcgnttttt ntttgggagg agactttgtt cctttcnatg aagatgcagg acgnggaaga | 720 |
| cgcagggtgt gaacaggaca cagnnacgct tnngtntntg tcngcntcag cngcgtggga | 780 |
| atgagtcaga gcagcacggg gaggtgcctg gatntaagct ttctggtagg gagaacagag | 840 |
| tgcaggcngc ggcccag | 857 |

<210> SEQ ID NO 57
<211> LENGTH: 902
<212> TYPE: DNA
<213> ORGANISM: Rattus norvegicus
<220> FEATURE:
<221> NAME/KEY: misc_feature
<222> LOCATION: 1- 902
<223> OTHER INFORMATION: n = g, a, c or t(u)

<400> SEQUENCE: 57

| | |
|---|---|
| aaaggggng ggaagaanga aaagggnaaa cnttngtttg gaagccnnca nnaaagnaan | 60 |
| gncgaattta anaagggggt agggaaaaaa aaaacanaat attccntcct tagccatnaa | 120 |
| ccgaacttcc ngcaaggaaa aaaaatttgg ngggngtaaa gggcaccncn tcccacaaaa | 180 |
| ttttgntaan tttgggcgca aattcangca ggntttngtt ggaaaggngn ananaccaaa | 240 |
| gggatttngg ggatttnaaa atcngngttt nnggcaggnn atccngaagt tngaatcgga | 300 |
| cgncnaccct ttatttnagc agttatttan gggaacatgg gagggnacca tttcaaacca | 360 |
| nggatcgggc cnggagtntg agtgttcagc ccacngcctt cnaacantac cgggataagt | 420 |
| ttttccctgn gccagagacc catccangtt ccagcaaaag gntggtcatc tngggcnagc | 480 |
| tccnngagtc atcnngggtt tctcccagcc ngggccaat ggtcgaaggc aggttntttt | 540 |

```
tgtctccagc ttgttcccna ccgngggagc ctgtcaaggc tgcacagnac cagantagtg      600
gtcatntcng gctagctccn ttagctccnt gtccagggga cttcctggca ctggattagt      660
ggnggactca ggcttgcttt tttttcagga gaggttagat tactaatcat tcagatgttc      720
ataagtcaga acactgagca aagcaatagn ttctcctcca cntactgant cacacgtgca      780
caacagccac acccgcaatg cttntaggag caggtccagn gnactttgt tttaactatt      840 tntggctctt tattaatcag cacataaata cgcttcgttt ctccttttc aatatgnatg      900 tg                                                                    902

<210> SEQ ID NO 58
<211> LENGTH: 852
<212> TYPE: DNA
<213> ORGANISM: Rattus norvegicus
<220> FEATURE:
<221> NAME/KEY: misc_feature
<222> LOCATION: 1- 852
<223> OTHER INFORMATION: n = g, a, c or t(u)

<400> SEQUENCE: 58
acagaggggg gggggggngtg gaattttngg naggangttn tnggaaggcc nctaaaaaag      60
aaatgttccc agaccaaaag ggggggggna gtnnaattca nggatcctna ngaggnggaa     120 attttttnnnn tattnaggat caggataaat angaaaangg gnanattttn nnnangnggg    180
tttttttttt tttttttttt tttttnngng gnnnnannan annnnnaaat ggcgncgggc     240
atggntaatg gggaanttgg gganaattac agagattttnt ttttcccatg ggnttccagg    300
atgaattcag ntaccaacca ggttggtacc agcattttaa cattcgagtt agacatcaat     360
ggttaggtcg ggagtgagag gttcggggcc ngacatatat tcntggtgaa cccagtgcac    420 ctttngggttt ntacaaggag cttgaggtag tcgcccacca gtagctgtca ggcaggtggc    480
ttaagttcag aaccgnttcg tggaacccga gaagcagaaa aagacataag ttntgcngct    540
tcanaatcca ctcntgaata cananatctc ggccaaagaa gcacagccag tctttccgtt     600
nacangaggc cgggagcaac aantccacag ccagcccaag ganatacaaa ggacttgggt     660
cagttctgna ccagttggag tcagagatgg ggccctcaaa gtcccagcag tgaagggcat    720
ggtctccagc nnacagtgga acctttaaga ggtggggact tgtaggagga gttagataat     780
tggggtgtgc ctttgtcccc nacntcgttc tttccctctt tatggccttg atgtggacaa    840
gattgtttct gc                                                          852

<210> SEQ ID NO 59
<211> LENGTH: 884
<212> TYPE: DNA
<213> ORGANISM: Rattus norvegicus
<220> FEATURE:
<221> NAME/KEY: misc_feature
<222> LOCATION: 1- 884
<223> OTHER INFORMATION: n = g, a, c or t(u)

<400> SEQUENCE: 59
aaaaaaaatt ntttttccna ggnaaataac ccgngcttaa ccgggcgggg gagatcaatt     60
ntttgtngtt gtttcctcng aggcggagng tcaaaanaga acacnnctgg naaaccccc     120 ttaaaanaca aaaatttgan ggggnnggng ngttacaaaa agacaggatg ttttccgagt    180
cggattcaat cccaccacaa catgggggttc acaccatngt aaggaatcgn tgccttttg    240 ggggtatcct aggggtana nttccaaata nngataanaa tttttttaaa aatttaattg    300
```

| | |
|---|---|
| tanatattta ttanataatt taataaataa tatttggana nantnatgtt ctngcgcctt | 360 |
| gnggactggt agttttttnt ccnnattnna actttcccag nactnggtag cctatgtgnt | 420 |
| tatgcaaccc nttagaagct gccttcanta ttnaactcat actgtttctc gataatcngg | 480 |
| ggagtagctc cagttngcta tgaagctgcg gaaaggtagg cggacatccc aggcttagac | 540 |
| agagttcagg ttatttggaa ctttnnaaca gaagtgtgtt cntgcacggc agcaagacna | 600 |
| tntgggtccc gtagttccgg tcgccaggag tagtgtattg cttaggacca ttctgggtgg | 660 |
| aatgcatctg gtgggtctta aannatgtca ggcagggcct ggcaccaggg tctggcggga | 720 |
| agcctcacat accgttntaa tgacttcatc tgcttagaat ttgtggggaa acgatgcaga | 780 |
| aaaatctaac cagggatgtt tctgggccag tcatgttggg gatgcctcag tcatgtaaaa | 840 |
| ttgagctccc cctggagcac accttaaaac atcttctgtt taat | 884 |

<210> SEQ ID NO 60
<211> LENGTH: 955
<212> TYPE: DNA
<213> ORGANISM: Rattus norvegicus
<220> FEATURE:
<221> NAME/KEY: misc_feature
<222> LOCATION: 1- 955
<223> OTHER INFORMATION: n = g, a, c or t(u)

<400> SEQUENCE: 60

| | |
|---|---|
| cccntggaaa accnaanana atangnnnan anaaanactc cncccattga gggaacnttt | 60 |
| tagggnttcc nnntttcccc ggancgcca aatgngacac caaaanngac cgnantcttt | 120 |
| ggnngttgct tctcttggan cgcnttttgt tcgaccgggg tgactaaggn catgtngggg | 180 |
| acgantaatt gtttccgggg gcngntcggc accttccnan gngngngngg tttggttctg | 240 |
| gaagnccgaa nnggcatgtn ttaagatttg ccnatccatt tagggttcgt tcaacgcctt | 300 |
| atcttntgag tttntggagt ttgggtgggg agggagatt tagtggagga gtaaattttt | 360 |
| agtagggaga gagggaaggg agatagaccc ggagacagag aagggaggga ggaagggagg | 420 |
| gattatcctg taggatgtga gcccagacnt gtctgtggtn tctttccatg acacaagaga | 480 |
| cttntgctt gtccctagaa tgcttcattt tntagtgtct caaacttaaa gggctagtgt | 540 |
| aaagttagac tgtgaacann tngtaaacac aggtgacagg aatgtntgtc agctgggccc | 600 |
| nttatatgcc acggcagagt ggtacgtgat gcccccacat gttatgtgga agttntcatg | 660 |
| cagggcttca gaacacagta gatggagatt gtgaaaatct gttgttnact taagagactg | 720 |
| gccccaagga tccatgtgat gntacttctg ttgcttgtgc tttaaaatct tatgtgatgt | 780 |
| tttgcagact ccnttcggga ccccagcaca cagctgagag tctgccctgc tggcactgct | 840 |
| gcctgtctgc tgaagggaa cccaggcatt tgatgttggc cggcccaagg aggggctgaa | 900 |
| gctantgagc aaggacagtg atagaccac acagnagttt gcaagtaaat gagnc | 955 |

<210> SEQ ID NO 61
<211> LENGTH: 1107
<212> TYPE: DNA
<213> ORGANISM: Rattus norvegicus
<220> FEATURE:
<221> NAME/KEY: misc_feature
<222> LOCATION: 1- 1107
<223> OTHER INFORMATION: n = g, a, c or t(u)

<400> SEQUENCE: 61

| | |
|---|---|
| caaannncaa nggtncnncn ggnccattgg gggggttaa naatggaggg gnttngggtt | 60 |
| ttaaannttc ccccnggntt caaggaaatg gggctttga ttggcaagga aggaatgggg | 120 |

```
nttcccntga anccctctga ggggccaaan attgggggggg gttnacaccc ccggggaaac        180
ccttcttgac cccnagaaan gcngtttagn ttcccnccca tgggntccct taccctgggn        240
tttttttgna cagccnagca gccctggttt tccttgtttc cttgggcncc gaaaatttga        300
atccagtgca ttccaccatt gagccngcag aggttgatng gcaggaaggg tttaacccctt       360 ngaccaggag tgacaaattt ngngggacnc cccagtgnga gctcacaaca ngtngacatt        420
gaggcnccaa aggattgttg agggatgga ttgtgtcgca gtctggttgc ctttatagtg         480
ccagcatcgt tgagcccccgc ccagggagtg ttggcacgcc caaacccccna cccagcgctt      540 gaggcaaggc aaacacactt cccagcccct taanttncna cgcctttgtt gcttggacgt        600
cccggantgg gagcaggatg aaggattttta gtgcaggaga agaccagtgc aagccggaga       660
catngagttc cctntaattc ggtgttcagt ttgccnttnt ggcacgtgac tcgtaactct        720
ggtatgtgtg ctgaaccntc taccagccag agatcagtgt ccttaaagtt cgaatcagtg        780 tgaggggggac tgggaacaat actgatgctg ttgccctcta gtggcaaggt caactccaag      840
cgagagggga agcagtcagt ctaccgcatc ctctaagata gtggttctcg acctctctaa        900
tactgcggat taatacattc ttcatgttgt ggtgacgctc caaccataaa gtgatttcg         960 ttgctgcttc ataactatat ttttgctact gttatgaatc gtgacataaa tactgtgttt      1020
tcagatggtc tcaggcaatt cctgtgaaag gggtctccca caggtttgaa agtntccac       1080 ctgtaggtgg gccaagctaa atgagat                                          1107
```

<210> SEQ ID NO 62
<211> LENGTH: 92
<212> TYPE: DNA
<213> ORGANISM: Rattus norvegicus
<220> FEATURE:
<221> NAME/KEY: misc_feature
<222> LOCATION: 1- 92
<223> OTHER INFORMATION: n = g, a, c or t(u)

<400> SEQUENCE: 62

```
atggggcatc ttgtaacagg aggcctggat tgagtactgt aactgagntc ttgaaagact         60
ttacctgtag gtttggncng cttgaaagag at                                      92
```

<210> SEQ ID NO 63
<211> LENGTH: 209
<212> TYPE: DNA
<213> ORGANISM: Rattus norvegicus
<220> FEATURE:
<221> NAME/KEY: misc_feature
<222> LOCATION: 1- 209
<223> OTHER INFORMATION: n = g, a, c or t(u)

<400> SEQUENCE: 63

```
aattccagcc catcctgaga cacacagtga ccctgtctca caaaaccagg gaaaagccag         60
gtgcggagtc tcacgccttt aatctcagtc tccggaaaca gaggcagngg gatctctgtg       120
agttcccagg cgaganttct ttgtacaggg nncctctga anncnctga aagatttcac         180 ctgtaggttg ggccnagctt aaaagagat                                         209
```

<210> SEQ ID NO 64
<211> LENGTH: 97
<212> TYPE: DNA
<213> ORGANISM: Rattus norvegicus

<400> SEQUENCE: 64

| acagagaaac agtgtttccg ttccttaaaa cgttgctcta tcttgaataa caagcttatt | 60 |
| acatgcgaat cgtattggga acctactgaa ttccgat | 97 |

<210> SEQ ID NO 65
<211> LENGTH: 1047
<212> TYPE: DNA
<213> ORGANISM: Rattus norvegicus
<220> FEATURE:
<221> NAME/KEY: misc_feature
<222> LOCATION: 1- 1047
<223> OTHER INFORMATION: n = g, a, c or t(u)

<400> SEQUENCE: 65

| caaggtgaat tccanttggn gtttnnaaat ngttttnaa aaanaaattt tntttggnna | 60 |
| ttgccttnaa ngtttgggnc ctgaattcaa aattccaant tacccaaaat ttcatgttcc | 120 |
| atccanaatt naattccgga aatttacaat aatttgaatt ntagttttcc caattntaat | 180 |
| ntcagtagtt tgnnttttgtg tgccccnatt ntaanatcag acccgtccaa tcacccaatt | 240 |
| gnttttnaa attgaatngt tttcccntgt accttccttg caangttgct ttaaattnga | 300 |
| atttcagaat ccccattgaa aagaatccgg gnnaaagcaa caccnttaag gaccccagga | 360 |
| aaccagaaat tngnagaaan ttggacgnag gganttnaca ttnttnccgc canaggatgn | 420 |
| ttgggntaaa aaccgcgttt gcgcaaggct cntgtgttgg cctcttttcc gccgggggcg | 480 |
| ctgtggataa tctctgggtc agtcgaaccg ttttaccatc catttcgtta ctccgagaga | 540 |
| ctggcgcncn gcgggttcct ccaagatggc ggcgcagagg aggagcttgc tccagagtgt | 600 |
| gaggaaaccg acccgctctc tgggctggga gggttgggag ctcgggtgtg tcntcgggtg | 660 |
| cagaagctgt tgtctttaga tggcagagtg cggaccctc gccccagagg ccntagggtg | 720 |
| cttgcagcgc gcgcaagacc cttccagtc tagagcctcg cctagttctg cgcgtgcgcg | 780 |
| ccacagagcc gggcctctga gggtcaaggg cgccggggtc ctgcggaatg ggagcgtcct | 840 |
| caagccggaa agggacatgg cgccgccgag cgggccatcc ggagggcgga cacgactaat | 900 |
| aataaatcgc ccccccgccc ccgcttgtgt aaggcgcgct gtatctctgg cattgtgtgg | 960 |
| accgcctcac attcataagc ttcgtcagca gcagtagaga atggcttgaa agacnttac | 1020 |
| ctgtaggttt ggcnagcttt aaaagat | 1047 |

<210> SEQ ID NO 66
<211> LENGTH: 1063
<212> TYPE: DNA
<213> ORGANISM: Rattus norvegicus
<220> FEATURE:
<221> NAME/KEY: misc_feature
<222> LOCATION: 1- 1063
<223> OTHER INFORMATION: n = g, a, c or t(u)

<400> SEQUENCE: 66

| catnggagtt cccaatggnt tccntnaann ggttntnttc aggttgggca ncntttagga | 60 |
| attgaaaatn ttnnttggga ttcccctaga atttgatccc attnggaaa tttttattt | 120 |
| ccngaacagt ccantnttaa aattgggcct nttgggatta acggattcca aggttgcaac | 180 |
| anattggcaa gtttnnggac aggaggtttc aantggntaa agtggataaa tngtgaattt | 240 |
| tggagangga attgacttgg ttgggggcca aaantaggta gcattttgcc cggagggttg | 300 |
| attgcattct gttttgtgta aanatgaagn tacttgacag ctttgagata agaaggagac | 360 |
| ntaatttgct aaacattttta agtgttctat tctgccggag ttttggagag ggtatatgcc | 420 |
| ggtcaggaag ggagccagaa gccagtaaca ttgcaagtat ttcaacatgg aaagctttag | 480 |

-continued

| | | |
|---|---|---|
| gttatctctt gtgcatctta tgctcggnta atgatgtaan ccaattgtaa ttctgggcac | 540 |
| agctttccca tgtgtctttg aacagtctg ggtttgtggt tntaaaacaa catttgtatn | 600 |
| tagttggagg cttatctaag gagcttctta gcatttgggt tgtaatttat tttagtattg | 660 |
| tttcagctac ccattgctac atagtaaatg tacaaaaatt tagtggatta aaataatgat | 720 |
| gtttggtttg ctcacgaatc tttcatgttg gctgaagttg ccatttctgc ttctctctgc | 780 |
| tgaacttggc atcaactgag agggttggaa tcatctgaag atggggttag ccacacctcg | 840 |
| cagttgatat tggctgtcag ttggaacctc agctggggtc agcatgcata agtaagcatg | 900 |
| tgtcactttt ccaggtttct gtcttacagc atggtggctt ggttctgaag ggccatcact | 960 |
| ctaatggtgg ctgggttccc agcgagaacc agtggancccc aaggatagct tttggtgact | 1020 |
| gaaagacttt aacctgtagg ttggggccna gctanaaaga gat | 1063 |

<210> SEQ ID NO 67
<211> LENGTH: 815
<212> TYPE: DNA
<213> ORGANISM: Rattus norvegicus
<220> FEATURE:
<221> NAME/KEY: misc_feature
<222> LOCATION: 1- 815
<223> OTHER INFORMATION: n = g, a, c or t(u)

<400> SEQUENCE: 67

| | | |
|---|---|---|
| ccccccccc aaaccttcct tccaaaccct tngggtggg gaaaacattg ggcaanggg | 60 |
| caaattnana ccccttggaa tngttngccn ggnaaagttn cngttcccca aaagccaaag | 120 |
| gggggggtt tccaaanatt ccngggggttt tttnnggggg taaagggntt naaaggtnaa | 180 |
| aaaatgttcc cggngccccc anacttccaa aggttttccc ttnnaaaatt ccnggccttc | 240 |
| cggggggnccn tntgtncccc ccnttccccn aaatnncntt nngaaaaggg ttnaanantg | 300 |
| ttnaaaancc cnaangttaa angggnnnat nnaaangtt tccctnncnn ggggngggna | 360 |
| aaaaggtttc gcgcgganac cnntgatgcc caggttcagt ttccccggag cttggggcca | 420 |
| gacccgcggc gcgccntggg tgtggcggga gcgcgcgggc ttgcgcccgg acggcttctc | 480 |
| cccgcccccg actccctcc gcggcggcgg gagtaggttc ttccggctcc ggtctgaggc | 540 |
| ggtgcctggc accttctgac caggatccgc gggtccccgt gctgtggtcc cgggaggcac | 600 |
| gcggggcctg cctgctatag cgggtttgca gggcgagcct ccctggagcg gtagggtcgg | 660 |
| tttggtgtt gcacgctcgg tttgacgttt taatccggag gagttgtggg gttcctcgaa | 720 |
| tctcaaactg ccttcttccc ttttgagact tgaaaatacc cgaagcctgc cttgtactga | 780 |
| aagacnttac ctgtaggttt ggcagcttaa aagat | 815 |

<210> SEQ ID NO 68
<211> LENGTH: 1034
<212> TYPE: DNA
<213> ORGANISM: Rattus norvegicus
<220> FEATURE:
<221> NAME/KEY: misc_feature
<222> LOCATION: 1- 1034
<223> OTHER INFORMATION: n = g, a, c or t(u)

<400> SEQUENCE: 68

| | | |
|---|---|---|
| aaaaaanagg tttccccngg angtccctng gggntcnttt tnngancntn cgttangggg | 60 |
| ncctncncct tttccccttg ggggaggggg nttttttaaag cnannnntng gtttcnnntn | 120 |
| gggttaagtn tttncccaaa agttggtttt tnnaaaaanc ccctttnncc cggacgtttn | 180 |

```
ccttnncngg anaatatntt ttgggccaaa ccngttagnc gggatttccc aattgcgncn        240
cccttgnaaa cgggttnccg gggggngtnt tnagggttg aacngggttt taaangtgcc        300
aaaacgggta aattggaggc attttngnaa tggcttttgt tnaaccnntc ccttgggaaa        360
gggttgtagt tttnaacggg naaacaaacc ccgtngtagc gggtgttttt tntttnccaa        420
gcgccggnta agccncggaa aaaaaggatn ccnggagacc ttgnattttn nnngggttt         480 nacgcnatnt tttttggaat tttgggggga taanaatttt nnaccngaat ttttngnggc        540
cncncnnngg gnnaaaaatc tnannannat tnggntattg aacatttctt ccntgcatat        600
ttatngangt atgacccttt aaacaattaa gtacttggct tcagtgggag agaaagtgct        660
tagcctcaaa aagacttgaa gtcccaggg tgtgtgtgtg tgtgtgtgtg tgtgtgtgtg        720
tatgtgtgtg tgtgtgtgtt tgtgtgtgtg taacccagag gggtgcccac ttgctcaaaa        780 gagaagggc agaggaatat gagggaagga ttgtgggagg gagtgaccag tagggaaaca        840
gtgagtgtga tgtaaagtga ataagtaaaa aaattaaatt aaattaaaag taaataaagt        900
gtctacaaag tcaattactc ctttcccttc ctccacccct tcttctaata ttaggcaaaa        960
acaaacncaa aaacanaaac aancaaactg aaagactnta acctgtaggt tggncagctt       1020
gaaagagatn tttc                                                         1034

<210> SEQ ID NO 69
<211> LENGTH: 186
<212> TYPE: DNA
<213> ORGANISM: Rattus norvegicus
<220> FEATURE:
<221> NAME/KEY: misc_feature
<222> LOCATION: 1- 186
<223> OTHER INFORMATION: n = g, a, c or t(u)

<400> SEQUENCE: 69
agaccacctg ggtggaaact cctattctta caccaagctg cctctgtatc cacagatacc         60
aagaagtagc caccgttgtt ttacttaact catggtccac ggggtgagct gaggtctcct        120
tcctgagcaa gatggaaatt ttacttggtc tgttaactag cgtgcattga atggangaca        180
tatgat                                                                   186

<210> SEQ ID NO 70
<211> LENGTH: 1028
<212> TYPE: DNA
<213> ORGANISM: Rattus norvegicus
<220> FEATURE:
<221> NAME/KEY: misc_feature
<222> LOCATION: 1- 1028
<223> OTHER INFORMATION: n = g, a, c or t(u)

<400> SEQUENCE: 70
aaagggaacn ttttaagcnt ttnnaattnn gttnccnaan aaggatttgc atttaccacc         60
cttaaattta ggnatttttg aatnatttca acccnttgca ggcagtttgt nccatgtttnt       120 gggaaagttt taacaggatg gttatttnga caaacaggt ttttcagac catttgtgna         180 ntatcttgaa atttcccagt ttttnaattn tattntaang atattntagt tnnaattnna        240
tgacttcaat ttgtatanac aggttcttaa caaacagtgt gtaactgagt accttgcccc        300
agcatttaag gttacacaca tcatacgaac actgaagaaa atgtctgntc tttaattttc        360
ccctttcctc tgtgtaattt ccttcaggac tcctttgtcc tgagtggtca ggcccttgat        420
aagatggttn atcttattc tgtttgccca tgtgttgtaa tcntgcctga cagttcttgc        480
ttaatgcaga aaccaagcaa aggttcagtt tgtactggcn tcccttttnta gttatctgac       540
```

```
agggatcagt tttcaagctg tagccgtggt cctcagagag acctctgccc atatacagca      600
gcagtctttc tcatcccagc cctgggagtt ctagcaaaga tttgactttc tgagttgttc      660
agggtcagag accatgtatc aagcctcggc tctatttctt gagtaaaatg ggcatctggc      720
acatctactt agatgcagaa atagtcagaa tgaagtgaag atgtaggagg agtcgtgtgg      780
agaaataggc tctctgaaag gaggcttctt cttcacttta taagctgtag tgtcatccct      840
tcccaagtgg ctctgaaact gtgttagaag acatggcctc cccagagctt ggggaaacct      900
taaataaggc tgctgctcag atgtcagcac attttacgct ttactggaag acttctgctt      960
cctcttccta tttctccaaa tncanntgaa agacttgtac ctgtaggttt gggccagctg     1020
aaaagatc                                                              1028

<210> SEQ ID NO 71
<211> LENGTH: 1034
<212> TYPE: DNA
<213> ORGANISM: Rattus norvegicus
<220> FEATURE:
<221> NAME/KEY: misc_feature
<222> LOCATION: 1- 1034
<223> OTHER INFORMATION: n = g, a, c or t(u)

<400> SEQUENCE: 71
aaaaaanagg tttccccngg angtccctng gggntcnttt tnngancntn cgttangggg       60
ncctncncct tttccccttg ggggaggggg ntttttaaag cnannnntng gtttcnnntn      120
gggttaagtn tttncccaaa agttggtttt tnnaaaaanc ccctttnncc cggacgtttn     180
ccttnncngg anaatatntt ttgggccaaa ccngttagnc gggatttccc aattgcgncn      240
cccttgnaaa cgggttnccg gggggngtnt tnaggggttg aacngggttt taaangtgcc      300
aaaacgggta aattggaggc attttngnaa tggcttttgt tnaaccnntc ccttgggaaa      360
gggttgtagt tttnaacggg naaacaaacc ccgtngtagc gggtgttttt tntttnccaa      420
gcgccggnta agccncggaa aaaaggatn ccnggagacc ttgnatttn nngggttt       480 nacgcnatnt ttttttggaat tttgggggga taanaatttt nnaccngaat ttttngnggc      540
cncncnnngg gnnaaaaatc tnannannat tnggntattg aacatttctt ccntgcatat      600
ttatngangt atgacccttt aaacaattaa gtacttggct tcagtgggag agaaagtgct      660
tagcctcaaa aagacttgaa gtgcccaggg tgtgtgtgtg tgtgtgtgtg tgtgtgtgtg      720
tatgtgtgtg tgtgtgtgtt tgtgtgtgtg taacccagag gggtgcccac ttgctcaaaa      780 gagaagggc agaggaatat gagggaagga ttgtgggagg gagtgaccag tagggaaaca      840
gtgagtgtga tgtaaagtga ataagtaaaa aattaaatt aaattaaaag taaataaagt      900
gtctacaaag tcaattactc ctttcccttc ctccaccctt tcttctaata ttaggcaaaa      960
acaaacncaa aaacanaaac aancaaactg aaagactnta acctgtaggt tggncagctt     1020
gaaagagatn tttc                                                      1034

<210> SEQ ID NO 72
<211> LENGTH: 824
<212> TYPE: DNA
<213> ORGANISM: Rattus norvegicus
<220> FEATURE:
<221> NAME/KEY: misc_feature
<222> LOCATION: 1- 824
<223> OTHER INFORMATION: n = g, a, c or t(u)

<400> SEQUENCE: 72
```

```
gggggnttt  cnnanntanc  aaaaantngn  tntancanng  antnnttgag  ntgttgaagn     60
aangnggaaa  angttttgaa  atcantgtaa  tgaggttcca  aaaattgagc  aggaaattgg   120
atgntgtcag  gagaaacccn  ttcagtnttg  tgcaattggt  tcgccagcag  ttaggaccgn   180
ttccccatca  cttgtgccag  cggacatcca  gntattgagc  cntgnatcat  ttatggnaca   240
aattaggaac  acacaacaga  gatccgcttt  ntgactgcca  tgttcgccaa  actcaattgg   300
gggaagtaat  cctccagacc  gttccgtttg  cacgtntagg  aagccacagt  gaaaacacaa   360
aattcgtgga  ggcgactcta  accaggaagc  ctaatcccnt  agattccgg  gacactgggg    420 caggcgtcct  aaaaacagct  ttgtggggct  tcagtcctcc  gtgcggttcc  agtccgggtc   480
ttggggatcg  ccctcgcggg  gaatgtccgg  gactccggtc  ggtatctttt  tggcctggga   540
atttccagcg  tgtggaaaaa  gtccacaaac  ttagtcctca  ctgcccgcct  cgcctcctcc   600
ggcccttctc  ggtgcccacg  cacccccga  tcgaacccga  ggatgagcat  agggtgtatt    660
ttaggcgtgc  tgggcttccc  cgccccctc  tgcccactta  gctggcaaga  agaaagccag    720
cactataaag  gaggccaggg  ccaaggactg  gcctcctctt  gctcacgagg  tcagacgcga   780
gctctgaaag  acttcacctg  taggtttggc  aagctgaaga  gatc                    824

<210> SEQ ID NO 73
<211> LENGTH: 774
<212> TYPE: DNA
<213> ORGANISM: Rattus norvegicus
<220> FEATURE:
<221> NAME/KEY: misc_feature
<222> LOCATION: 1- 774
<223> OTHER INFORMATION: n = g, a, c or t(u)

<400> SEQUENCE: 73
gagggganna  ncancaggac  caancngata  aggggtcaa   caacntgngt  tccncccntt    60 gagnggaaa   tgagcacgng  gcantccaac  cgntcaaggt  cccgnttcgg  acggtcacac   120
antaggttnt  catntggatt  gccngngttc  cngttggcat  ccgggaaaan  tgagactgtg   180
tcggtaccag  agntaggatg  gccntccttc  ccngccccgg  ccttnttggc  gccttgcgat   240
ccttcccgaa  ccggcccntg  gcgtctccgc  cttnggcact  gcacatntg   gcggcccagg    300 atggcgcttc  cgggatggcg  ccagcgcgcg  tacgtcatca  cggagcgtcc  atgtgttcct   360
tctgtccaag  cgcntaggag  cctgcgcgta  ctcccagcaa  ggaagatgta  ggaccaaaat   420
gtagaagcac  ttaacatgaa  cgtcaaaacg  atgaccaatc  acaggcgat   atatgcgcat    480 gcgcaatgtt  ccaatcatgg  ctcataagca  atccggaagt  ggccaattaa  atatactatt   540
tactaatcca  gggttacaca  gtgaaaccct  gtctcgaaaa  ataaacacag  ggctggagag   600
atggctcact  gattaagaac  actgactgct  cttccagaag  tcttgagttc  aattccgagc   660
aagcacatgg  tggctcacaa  ccatctgtaa  cagattctgg  tttatgtnga  gacaactaca   720
gtgtactcgt  attgaaagnt  ncccaccgt  aggttnggca   agctaaanga  gatc         774

<210> SEQ ID NO 74
<211> LENGTH: 248
<212> TYPE: DNA
<213> ORGANISM: Rattus norvegicus
<220> FEATURE:
<221> NAME/KEY: misc_feature
<222> LOCATION: 1- 248
<223> OTHER INFORMATION: n = g, a, c or t(u)

<400> SEQUENCE: 74
tgacacttca  tggaaactga  gaccgggagc  ttccaccaga  aggcactgcc  cagtggagaa    60
```

| | |
|---|---|
| aaccgacttc ttttttgttgt tgttctgatg ttttgttttt gagataaagg tctcactgtg | 120 |
| tagctcaggc tggttttgaa atcaggatcc tgaccctcag gaatgttaaa gtgcctaaaa | 180 |
| gtggngacaa attattttac gtgcctttga aagacttcac ctgtaggttn ggcnagctag | 240 |
| aagagatc | 248 |

<210> SEQ ID NO 75
<211> LENGTH: 833
<212> TYPE: DNA
<213> ORGANISM: Rattus norvegicus
<220> FEATURE:
<221> NAME/KEY: misc_feature
<222> LOCATION: 1- 833
<223> OTHER INFORMATION: n = g, a, c or t(u)

<400> SEQUENCE: 75

| | |
|---|---|
| aangggtta tnntggagan atnctaagnt cccaaagcaa nttaggattg ctnccnnnng | 60 |
| aattnttaag cntttgcatt aagtantaat gccaaaatga ccccaanata tngntccttg | 120 |
| antgtnntaa aaangaggat cttcnttgnc catanacgcc ntatatgaaa gcaactgaac | 180 |
| aagatttaaa attggacagg tcacaancgg gcgtgtgcct ttaatcccag cactcgntgg | 240 |
| ctgatagaag cagatgcatn tatgtgggtt tgaggacagn tngnttnacg tagagagttc | 300 |
| ntatatcagt agggctttgt agagaccnta tctcaaaaaa caaaagcaaa acaacagaga | 360 |
| aaaaatcaat tgaccatgtc ccaattacct ttatttatct gtaacctatc cttagttata | 420 |
| ctcgtaatct ttttctctct tcagtttgcg tacgggacag cagacctact cacaacccaa | 480 |
| gctntaaatg atgagcgtac tcagccaggg agcttcaccc cacttaaccc cataagatgg | 540 |
| cggcagcgcc tcttcaccca ctcagggctg aagcacgcat cacgtgatgc gctccagctc | 600 |
| tcgccgcggt ggctgacggg aggtggagat agaacgaggg tgtcggccat tttgtgtctg | 660 |
| tttcctgccg gacgtggtgg tggcggttgg ttccagaaac tgtgcgagtc tcttctctct | 720 |
| ttttttttt tgttttttcg ttttcccccc agcttctttt cgcctctntt ctgcatagtc | 780 |
| tgtagtgcgc agttgaaaga ttccacctgt aggttgggca agctaaaaga gat | 833 |

<210> SEQ ID NO 76
<211> LENGTH: 880
<212> TYPE: DNA
<213> ORGANISM: Rattus norvegicus
<220> FEATURE:
<221> NAME/KEY: misc_feature
<222> LOCATION: 1- 880
<223> OTHER INFORMATION: n = g, a, c or t(u)

<400> SEQUENCE: 76

| | |
|---|---|
| aanatggntt ggttntaaag gttaaaattg gggcaaaatt tttccgcccg ggtccttaaa | 60 |
| ccggattaac tccaaggcca aaattccgag ggggaatcaa caacaaggac ccaaccggat | 120 |
| taaggcgggt tcaaacaaac ttggatttcc ngccctttgg ggcggggggaa atgggcacgg | 180 |
| gngcattcca agcngntcaa ggttccggct tgcggacggt taacacaant aggtttctca | 240 |
| tctagattgg ccngcgttgc ggttgagcat ccggaaaaat tgagattgtg tcggtaccag | 300 |
| aggtaggatg ggccttcctt cccngccccg gcttcctggc gccttgcnat ccttcccgaa | 360 |
| ccggcccttg ggtctccggc cttgggcact tgcacatctg gcggcagga tgcgcttccg | 420 |
| ggatggcgcc agcgcgcgta cgtcatcacg gagcgtccat tgttcnttc tgtccaagcg | 480 |
| cttaggagcc tgcgcgtact cccagcaagg aagatgtagg accaaaatgt agaagcactt | 540 |

| aacatgaacg tcaaaacgat gaccaatcac agggcgatat atgcgcatgc gcaatgttcc | 600 |
| aatcatggct cataagcaat ccggaagtgg ccaattaaat atactattta ctaatccagg | 660 |
| gttacacagt gaaaccctgt ctcgaaaaat aaacacaggg ctggagagat ggctcactga | 720 |
| ttaagaacac tgactgctct tccagaagtc ttgagttcaa ttccgagcaa gcacatggtg | 780 |
| gctcacaacc atctgtaaca gattctggtt tatctggnnt cnactacagt gtannggcat | 840 |
| tgaaagatnn tacctgtagg ttggncagct aaaaaggatc | 880 |

<210> SEQ ID NO 77
<211> LENGTH: 864
<212> TYPE: DNA
<213> ORGANISM: Rattus norvegicus
<220> FEATURE:
<221> NAME/KEY: misc_feature
<222> LOCATION: 1- 864
<223> OTHER INFORMATION: n = g, a, c or t(u)

<400> SEQUENCE: 77

| aattttaant tgttggnata anggcttgnc catatccttc ctnttgtttg ccctaagtaa | 60 |
| cagccaattg ggggagaant tttntgtcag tatcatattt ttcgttaggg aacggaggcn | 120 |
| caggaantga tccntntggg ttacagtcat tttagcatag gntgacagtt ggngaccaan | 180 |
| tnatcttgcc gtgttggaag gagagggggan taaggntgaa gctcttgagt ccnttgangc | 240 |
| ccttggaatc gggaantccc ttaaaccaac ccctttttgcc gttgaattgc accaaccaga | 300 |
| ttcttccagt ctgcttgagg angacaggac ttcattgctn tggagagggg caggagggtt | 360 |
| gggagttgac ntnacagggc tcagggattc ttttagaagg gtccaggttc atggcttccc | 420 |
| cccccccag ccaggtcaga cactaaagtg tcttaagccc ctccatactt gccgctcccc | 480 |
| cacnttggat gaagccggcc attaggcagg accgtctct gggagaggcc aagccctctg | 540 |
| gctcacttgt ggatttcctt taagcaagac ttcctctctg cttccaggac tcctgtcaaa | 600 |
| caagagggtc cctggcttag agtttgggag ctgcaggcag aacagacatt ccccgatgac | 660 |
| tcacaagcct ggaactctgt gggccagcag gaatggggat ggctttctgg tcagtcaggg | 720 |
| tcaactggga cactcactct gagacaggga ggcaaggag aaacaggtca gaggtagaga | 780 |
| gagctcagtc ccagggactc acgttgaggt ccctaaggtg cgctagggag aggnttttac | 840 |
| attcggttng gcaagctaaa agag | 864 |

<210> SEQ ID NO 78
<211> LENGTH: 874
<212> TYPE: DNA
<213> ORGANISM: Rattus norvegicus
<220> FEATURE:
<221> NAME/KEY: misc_feature
<222> LOCATION: 1- 874
<223> OTHER INFORMATION: n = g, a, c or t(u)

<400> SEQUENCE: 78

| gaggttggac cacaaggagn ttggnggaaa atnnaaaagt caacctatca gggtgtcttt | 60 |
| tagtttggaa cagaggcttg ggcagaaata tgggcaagta ttaggaaagt acaaggggaa | 120 |
| atgttgtcaa cgcgnttgtt ttcccagttg ttgnactgat cccnccagga tgttttccca | 180 |
| cntatgntat ggaaccntct cttttcaggaa gccattntna ncntatggnt tgcaccccct | 240 |
| ttggggtcgc aacagcaggt attaacatta ggattcataa cgntagcaaa atnacagtta | 300 |
| tggagtagca atgaaataac tctatgnttg ggagggtcac cacaacanga gggacgggtat | 360 |
| cacaggnttt tagcattagg aaggttgagg accttatttc agagtgtcnt gacaatcnntt | 420 |

```
cntgggacca cttgacttna tctggagccc tttccctcac gctcntactc cttaccatct      480
ctgcacagct ctntgaggct tagagcggtc tttcttcata gctttccntt ttccttcagg      540
tatgcagtca catcttgctt tagaccccag ggacattccg tgtctgactc actgcacaaa      600
atagtttccc acatatgagt cctcaaccgc cccacatcac gagacggaca agaccggaga      660
cgccatacat tctgtatttg ccctccttcc tcatttaaat aggaatttgt tgctgtttaa      720
tttttcatta tttgtgtgtg tgtgtgtgtg tgtgtgtgtg tgtgtgtgtg tgtgtgtgtg      780
tgcgcgcgca cgttaatatg ccgctcagaa tagtctaaaa ctgctgggct tgaaagacnt      840
ncacctgtag gtttgggcna gctaaaagag tatc                                 874

<210> SEQ ID NO 79
<211> LENGTH: 886
<212> TYPE: DNA
<213> ORGANISM: Rattus norvegicus
<220> FEATURE:
<221> NAME/KEY: misc_feature
<222> LOCATION: 1- 886
<223> OTHER INFORMATION: n = g, a, c or t(u)

<400> SEQUENCE: 79
atttttnaat tgcagcaatc ctcctgcctt ttttcttggt tgttaantca caggatnttt       60
gcacacttga ggttgaantt gcagcaatcc tcctgctttt gtttnttggg cgcttggatt      120
atagtatgtg cataacactt gagcagtaac tgttttcttc aatctcattt atctcagaag      180
ttccccttgn tgattcagac gttattaatt aggcaaacca atgttgattg tcattaccca      240
tgagttgctt ggcttgtgag atgcatactg tgtgttcgtg aggcacntac tgtgaggcat      300
gtgcccgtga ggttcatggc tgtgaggtgt gtgcccgtga ggttcatggc tttctngacc      360
acngggagta tgaaggagag gaatcctacg tttgatgcca gccagggtta tacagcaaga      420
tcccgtctca aaacaaaatg aagaagtaga gagattagtg ttaataagca actgaggcct      480
tgaagggctg aggtcaggcg gtgccctggt gcacacacag aagcgtgcca gtgacgtcag      540
acagactcag ccctgtgtca gacaggccgg agggtgactg gccatgtggc gtgattggac      600
acattcccaa aaaggaact cgatggaaga ggctcctctn gctccagaca gggcggtggt       660
tatgtgactt gtgcgagatt agtctcatac cctattgcta gcctgtgcct ggtaccacgg      720
acatggtaca atccagggag gagccgtaag cactacaggg gagccatcct gaatcccagc      780
aagtccaact tctgtttttt cttccttccc cgcaacatta ggaatgactt ctaagagngc      840
tgttgaaaga ctttcacctg taggttgggc aagcttaaaa gaggat                    886

<210> SEQ ID NO 80
<211> LENGTH: 865
<212> TYPE: DNA
<213> ORGANISM: Rattus norvegicus
<220> FEATURE:
<221> NAME/KEY: misc_feature
<222> LOCATION: 1- 865
<223> OTHER INFORMATION: n = g, a, c or t(u)

<400> SEQUENCE: 80
tggaggtaaa agtcacaagn ttttcaaggg tttgagatga cagttcaacg tgagnattng       60
acaaggattg attcttgtnn acaggaaagn tccccatccc accaananac accgtgttca      120
ggcccantgc tcagagctcc gggcgccagc gaagggcaaa cggccactga ttggaaagnt      180
gcagtttaaa gacatgtccc aggaactggt anccttgtgt gactggactt agccttgcaa      240
```

```
ntctgtctga agcataacnt gntgctgtct ntgggcgagc atttatgtgc cccacttgag    300
acccatctca ggacacgcag gacacggtcc agtggagctt tccctccaga gagaggtgtt    360
agggnccatc agtgagcttc caaggacagg ggaccagaac ggtgaaaaca aaccagggct    420
gtgaaggaga gcagggcggg ggggggggga gggggggcgc tctntagaat agattgaacc    480
tgcagagctg cttgctacct gaagttgtca ccctttaccc cacccacntc atctgtctct    540
gcttgaccat ctcagcaagt gtcacctcgc tgccaggaca caagtttcct aaagcttatt    600
tcagtgtcag ccgctgggga gacacattca gggcatgggc gtcccccagc cctcggggag    660
aatgtgggag gtggcgatgt gggagggatt cgagagaaga gaatgcttaa gaaccatcca    720
gggaacctgt gcgtttgaag gtctgagtta cacacaggct gctcaggaag gagctagagc    780
tccaaatagg agctgtgatc aggctgtgtg tgtgtgcctg gtgaaagact ttnacctgta    840
ggtttgggcn agcttgaaaa gtatc                                         865
```

```
<210> SEQ ID NO 81
<211> LENGTH: 859
<212> TYPE: DNA
<213> ORGANISM: Rattus norvegicus
<220> FEATURE:
<221> NAME/KEY: misc_feature
<222> LOCATION: 1- 859
<223> OTHER INFORMATION: n = g, a, c or t(u)

<400> SEQUENCE: 81
cangagcant ntgaancagg catttntgga agggctccng agaaaacacg tggaattnct    60
tgtctctggg actttagtnc cagcnaggan gatncagtga gggaacacac cgggcttttg   120
ttgtgcacgg gaggccaggc tcancnncct tgggagnttg acatccagca ggctatanac   180
agtgatccag gggacatgta cacatgggga actgnccagg cagagaaaga caagagaaaa   240
tctcaaanga tgaagacaga gangagtaat atggccagaa ngatacagtg cctcntgcat   300
aacccttgag tttaatttcc agggtcaact gtattttgaa agtataaatg aaagttcctg   360
aagtaataaa tttataggat gttagtatca cactgttcag aatagctcaa aaaatcctgc   420
cntgtcctct taagtatgtg aatcatcttt tactgcaacg tgtccacaat gtatatacta   480
catacccaaa agtcctcact gttatcccaa ttagtaggct ggctgccaat agttgtccat   540
acagagtgcc tgctgctgtg gccatccnta ctgtagtaaa cagtcatcca aagctcagga   600
gtgaggctat tgtagaaatg cacttcctgg gggccctact gtcagtgagc acctgagaga   660
gaaagggaca caggcccaag gtgggaggcc ttagataaag gcccatcatg ctcaggaaag   720
gatttntaca gatctcttag ggaagttaca atcaaattca tacctcacag cagagctcag   780
gagaagaatc cataaagnnt gaagacatgc ttgtngtgnc tgaaggacnn tacntgtagn   840
tngggccngc tgaaattt                                                 859
```

```
<210> SEQ ID NO 82
<211> LENGTH: 1021
<212> TYPE: DNA
<213> ORGANISM: Rattus norvegicus
<220> FEATURE:
<221> NAME/KEY: misc_feature
<222> LOCATION: 1- 1021
<223> OTHER INFORMATION: n = g, a, c or t(u)

<400> SEQUENCE: 82
caatngncaa aggtttggaa cccgngaaat ttnaaaagtt tgcgngantg gttgacnttc    60
cnggtgtnaa nggtttcccc gttcngattg nagggatcnc ttttatccct tttttnagnt   120
```

-continued

```
ttttttttgag nggaattttg ggttcnaant gngttaccct taagtaaccc cattttgcan    180
ggcatggaaa atacctaaan tgggatngaa agttcanatn gaggtcagga anggntggaa    240
cagggtngac cggttngacc gttggacctt tgaganccat cagatntttc ccaggttncc    300
ccaaggactt gaaatgaccn tgtnccttat ttnaantacc caatcagttg gtttctcgct    360
tctgttcgcg cgttttttgtt cccggagttc aataaaggag cccacaaccc ntcantnggg    420
cgccagtcct ccgattgact gagtcgcccg ggtacccgtg tatccaataa accntcttgc    480
agttgcatcc gacttgtggt cttcgctgtt ccttgggagg gtctcctctg agtgattgac    540
tacccgtcag cggggtctt tcaaactgca gttctcaagt aagctcaacc atccgagggt    600
cattctcaaa gccaagtcaa acttgggagc cctcactcct ggtggtcttt caaaagaccg    660
tgcattggat agtcagagac tctgcaggag cggattaagt ccaggcctgt ctccctgctt    720
tctgcctggg ttctaaagtc aagaaggcca gatggctcag atagttgaga cagtggctta    780
gctgattctc tggggatgca tttggtctgc ccaggaaacc ctggagagtt ttctacccaa    840
gatactaaag ttcaaacggc agcgcctgtc ggcagactca gcctatacaa agctggcctg    900
tatctgatgg gattntaagt ccctgggcag acccggtttt gtgggcctga agcttgagtt    960
ncaggagact tagtgggcca tgggattctt ttaggatccc gatatggnca aacttaaact    1020
g                                                                   1021
```

<210> SEQ ID NO 83
<211> LENGTH: 1013
<212> TYPE: DNA
<213> ORGANISM: Rattus norvegicus
<220> FEATURE:
<221> NAME/KEY: misc_feature
<222> LOCATION: 1- 1013
<223> OTHER INFORMATION: n = g, a, c or t(u)

<400> SEQUENCE: 83

```
ttttgagttt tctcngcccg nttgtgncng aaanncagcg ggggtntntc actgtgnntc    60
tcacatgtnc tcacacanat cngggggacn ctcacancnn catctcacnt ntgnganctc   120
acactcgtgt gggntctttc aaaacantgt ncnntggata cncagacact cnncnagngn   180
ggtntatctn cacnngtgtc tcngngnttt nngcnngnnn tcnaanctca aaagcgncat   240
nnggcacata tntntgacac ngnggtatat nngnctctcn ggnganacat ttgntncgca   300
caaaaanccn tggagattn tctacncaat annctanttt tcacaggnga gcncntgtnn   360
anacncncac cntanacaan tnggnntgt ntcagaggng attttanctc nntggncana   420
cccgnttntg tgnnccaaan tnttgttttc caagacatat agtggnacat gnnactctnc   480
gatntccgat gagnananat gtgntcngac ntttacagcg natacacngt ggngcanntn   540
tcacagatat gtgntatnt cnnacanaca aatntgcnng actcctctcg tgtataaatc   600
aatanacggg nnggttaaca tnnggccncn gttgnncagt natancgnga aacacactcn   660
caagggctnc aanttttnca nctatacacn cncncccgan gggncngngc acaaatgtgc   720
nccgaaattt tatncgccnc naacactctn aaattnntcc cgggaccta gatatatttn    780 tccncattna aaatttgcac atntntttncc anttgcangg gnatcgggg gttcaccccnc   840 cncnttggga agggnntnt tnaacccggg ttcnaantta taggggggtt tanatcnccc    900
cattttttna aaaagngttt acentgggcc cntntttttn cnaaaaatt tgncccgnt   960 ttancnccgg ggttggggaa cncgaatttc ttngggngcc ccctnagnn ttt          1013
```

<210> SEQ ID NO 84
<211> LENGTH: 1002
<212> TYPE: DNA
<213> ORGANISM: Rattus norvegicus
<220> FEATURE:
<221> NAME/KEY: misc_feature
<222> LOCATION: 1- 1002
<223> OTHER INFORMATION: n = g, a, c or t(u)

<400> SEQUENCE: 84

| | | | | | |
|---|---|---|---|---|---|
| aaananttna | cacggattcc | ttttcctcaa | aaccaatggg | ggaataaatg | atgtngtagg | 60 |
| gttccccngt | aatggatact | aggttgaact | tccangggga | antattattt | caataaggtt | 120 |
| ttagaggtcc | cacttgtnat | caggttattc | tgttgctttg | ggtcaagcaa | acagccnatc | 180 |
| aggattgtga | ttattngant | aacccattta | cctacagcn | gggaggaaan | ccaagggag | 240 |
| gcttgaggaa | acggcttgtg | ggttcataaa | ctctttgaat | catacctTGG | gtgattcaaa | 300 |
| tgcttttTAC | taggctctcc | tttcatagta | cctctcttgt | ggacaaggac | ccagtccttt | 360 |
| gaaaagcatt | gaaaactcaa | accataccac | tatcagtttc | agctttaata | taaattagct | 420 |
| ttctaagttc | agctgaccac | nttttcactg | gaccttcact | gatctcacag | ggaagatata | 480 |
| ttttcaacaa | ttacaaagac | atttctgggt | tggactatgc | attcctttgg | gccagattct | 540 |
| acatcctttt | tttatgccag | aatttttag | cgttcctgta | agattgtcag | tttcccctag | 600 |
| gaaatccata | aagctttaaa | tgccttctaa | atagccaata | ttttaatgag | aaatgtagtc | 660 |
| actgatatct | ctttgtattt | aaaggttatt | ttgagggga | ttgcttggtt | ggttggttgg | 720 |
| ttggttggtt | ggttggttag | ttggttggtt | ttggctttgg | ttttctgtcc | catggtaata | 780 |
| tgatacttat | gtcatagatt | agttaactca | aatggtcttt | tcaggtggca | gtctggaaaa | 840 |
| caactaactt | gggggaaaa | aggctgctcc | atgttctata | aaagctgtac | atgtgatttt | 900 |
| ctctgcttta | cctttatac | tcatttattn | tgttatttgt | gtatgaaagc | cttccgtatg | 960 |
| aaagaccntt | acctgtaggt | ttggggngct | agaaaagatc | tc | | 1002 |

<210> SEQ ID NO 85
<211> LENGTH: 1031
<212> TYPE: DNA
<213> ORGANISM: Rattus norvegicus
<220> FEATURE:
<221> NAME/KEY: misc_feature
<222> LOCATION: 1- 1037
<223> OTHER INFORMATION: n = g, a, c or t(u)

<400> SEQUENCE: 85

| | | | | | |
|---|---|---|---|---|---|
| caacnnccat | nttttggaat | ttgnggggta | aaatttaaac | cgattcnttt | tccncaaacc | 60 |
| caantggggg | atatnnatgt | atgtngtagg | gtccccngt | aatggaatat | ttaggttgaa | 120 |
| cttacaaggg | aaatattatt | ttcacaatgg | tttagaggtt | ccactgtnac | aagtattctg | 180 |
| ttgctttggn | ccangtcaaa | cagcccatca | ggatggtgat | attagaatta | accatttatc | 240 |
| caacagccag | gagaaancca | aagggagctt | gagaacggc | tgtgggttca | taaaactctt | 300 |
| tgaatcatac | cttggtgatt | caaatgcttt | ttattaggct | ctccttcata | gtacctctct | 360 |
| tgtggacaaa | gaccccagtc | ctttgaaagc | attgaaactc | aaaccatacc | actatcagtt | 420 |
| tcagctttaa | tataaattag | cttttctaagt | tcagctgacc | accttttcac | tggaccttca | 480 |
| ctgatctcac | agggaagata | tattttcaac | aattacaaag | acatttctgg | gttggactat | 540 |
| gcattccttt | gggccagatt | ctacatcctt | ttttatgcc | agaattttt | agcgttcctg | 600 |
| taagattgtc | agtttcccct | aggaaatcca | taaagcttta | aatgccttct | aaatagccaa | 660 |

-continued

| | |
|---|---|
| tattttaatg agaaatgtag tcactgatat ctctttgtat ttaaaggtta ttttgagggg | 720 |
| agttgcttgg ttggttggtt ggttggttgg ttggttggtt agttggttgg ttttggcttt | 780 |
| ggttttctgt cccatggtaa tatgatactt atgtcataga ttagttaact caaatggtct | 840 |
| tttcaggtgg cagtctggaa acaactaac ttgggggaa aaaggctgct ccatgttcta | 900 |
| taaaagctgt acatgtgatt ttctctgctt tacctttat actcatttat tttgttattt | 960 |
| gtgtatgaaa gcccttcncc tatgaaagac nttcactgta ggtttgggcn gctagaaagn | 1020 |
| gatcnnnaaa a | 1031 |

<210> SEQ ID NO 86
<211> LENGTH: 1039
<212> TYPE: DNA
<213> ORGANISM: Rattus norvegicus
<220> FEATURE:
<221> NAME/KEY: misc_feature
<222> LOCATION: 1- 1039
<223> OTHER INFORMATION: n = g, a, c or t(u)

<400> SEQUENCE: 86

| | |
|---|---|
| aantttgng agtntttgga atnnaacngc ggttccttat gntggnnaan aaaccnctnc | 60 |
| nanacccaa taccttggat nttttaanat gcncctgggt aagcnaantt gaattatttt | 120 |
| ccntgggata anagtggaa tcattgacag ttttgtggtc cttttnncat ccccatgngg | 180 |
| tttnatgact aggcactta tttcatggac aaaccagtgt tgtccctcnt ggggactgag | 240 |
| tgggattaaa aaaaccttcc aaaaatgtgt aatntgatca aacccattga acaatcagt | 300 |
| gnggagtatt agcaaattaa actgacttgt tcacttntga aaantgatgt ctgatttcgg | 360 |
| aagaatccca gtgcctcggg acatgaaagg agatgtaac cttgagttca tggttaggag | 420 |
| ggaattcata gagacagttg gtaaaaatct gagtgaggtt gagaggttgg aggaccacat | 480 |
| tgtgtatttg ctcatcntgt gagggagaga ctttgtactc tgctctgaga aggcagaact | 540 |
| gttaggcaga cacttagaga atatatgtca tggcaaaaga catccaccca acaagtcttc | 600 |
| agtaacaaag cactaaacag aaaggggttg aagagactgg tcagtggctg agagcttta | 660 |
| ttgctcttac agaggactcg gcatgcntag cagctcacaa cagcntgtga cttcaacact | 720 |
| atgcctctgg cctcaggaga cacctgtgta ctcccaccca gacacatata cttaaaaata | 780 |
| aaagaaatct tttaaacatt gagcaaatgt aatcaggtac taacattgaa tatatctggg | 840 |
| gccaggaatt attctggttt attgcctttt tcggaagcct aatatcacac atagagaaat | 900 |
| aggcagcaca ggcctaacag cccataatgt gtgctattct atcaatagtg ccaagtattg | 960 |
| acatggacta ttcaaaaggc ccaaaagtta aatggcccag aagtncaaca taaagncggg | 1020 |
| cnagctaaaa gagatcntc | 1039 |

<210> SEQ ID NO 87
<211> LENGTH: 1058
<212> TYPE: DNA
<213> ORGANISM: Rattus norvegicus
<220> FEATURE:
<221> NAME/KEY: misc_feature
<222> LOCATION: 1- 1058
<223> OTHER INFORMATION: n = g, a, c or t(u)

<400> SEQUENCE: 87

| | |
|---|---|
| aaaagctttt tttcagnttg gccaattttt aacccattaa anattgttnt ttggaatcng | 60 |
| catttggtna ngttattgnc gaggaaggta ntaagggant ttttcccaaa ttncaaccat | 120 |

```
tnttggccag ttgggatttt gattgantgg gaaccccca ggntttaata agcctttgga      180
tttgttcaca ggggattaac aaantccttt gnttaatggg gattgaattt gggaaattgn      240
ttccntaatt ttccaggacc aatgcacant ggantattag aactgatgta acagagtgat      300
atgggaccaa gtaggaacaa gggtgcaggt ttgccgaggc aggtaattgn tggtcttgtc      360
attgtcataa ctttcttgaa agttttagga cttggacgga cagaagacat gatcattagt      420
atacttgatg acaagtggag atgaaaggac aaaaattgtg cacatcaaga ggagaattta      480
acattgggtt ttcttgcatt agctatccac tcttgccctc accctccac cccttaatc      540 ccagttacct tgacgattga ggtcattttc tctgaacaca ttctcttctt ggatgttaaa      600
gtgccatttg acactgtgtt tagggacact gcttaggccg gggtggggga attgccacag      660
aagcttgacc ttagaaggtt gagactctgg aagcctgaga gagatgagat ctgtcaaaga      720
aacgcttagc gttggtatgg gatgcgtagg aggctgtact cttgttctct agatgctatc      780
acgggtgatg taggagaaat gatctcactc agcccaagat cattcccttc caatgtgct       840 catcccatca gcaagcaaga cctgtactga agccagcagg ggcgtggtac agagtccggc      900 atttttgca tgccatgctg gtttgatgtt tgaactctaa aggtggagac tgttgggggc       960
agcagggcag acagtcttct gatgatttct ctgccttcaa actgaggtnn actcttgaaa     1020
gattncacct gtaggtnggg caagctaaaa gagaggcc                             1058

<210> SEQ ID NO 88
<211> LENGTH: 1043
<212> TYPE: DNA
<213> ORGANISM: Rattus norvegicus
<220> FEATURE:
<221> NAME/KEY: misc_feature
<222> LOCATION: 1- 1043
<223> OTHER INFORMATION: n = g, a, c or t(u)

<400> SEQUENCE: 88
attttccatt gcgcnccatt gaacggnttt gcgnggggtn ttagggggtnn aanggatttt     60 nagtgtgccn aanaaggtac attgaaggcn ttnttttggat ttggntttgt aaanccattc    120
ccttngaaaa ngagttgtag tnttaancgg caaacaacca ccggttgtag cgtggttttt    180
tgttgcaagc ngcggttagg gcggaaaaaa ggatntaagg agatcctttn ncttttcttg    240
ggggtctgac gnntcatgtt gtgtggaatt ntgagcggtt acaatttcac acngatttt     300 tatgcaaatc cacttgccaa gttggnataa ctgacttatt ttaccgggaa ntctccatgt    360
atcttctttg gacacttacc cttacagagc ccaggatgaa ttttgaccaa gccaagtatt    420
cacacagccc aatgtgacat gttaccacaa attggngatt ttccttcagt acactcaaat    480
gacacaagct ttttctcgat gtctttcttg tcattcacta ccaggatgaa attaattta     540 tcttctgagg angcaatata cgatccaccc aggaaaattc actttagatc ttcgttctca    600
tttcttggca aacagaattt gagctgaatt tctcttagaa aaatctgtcn ttcagaaact    660
taaattcttg ctgttccata acagaagtca gcaagtgact cacccctccag atacaggtat    720 attacctcca ctcccatcca cagagactta attctagtca gcttcatgat agtgagcctt    780
catccgtaag gagctgtatg gtatgggaag gggatacaga cagggccagg ggtgttttta    840
aacggtaacc cagggaccac atccattaaa aacactggac tgtttgtgag agtgtatatt    900
cctgagcatt gcctatccct taaggtacta caaaatttgg gagtgaggct cagcaaacta    960
ttttaacatg cctctccacc aacnactcaa gattcccgtg nacagttgaa agttttncacc   1020 aaaggtgggc aagctaaaga gat                                            1043
```

<210> SEQ ID NO 89
<211> LENGTH: 454
<212> TYPE: DNA
<213> ORGANISM: Rattus norvegicus
<220> FEATURE:
<221> NAME/KEY: misc_feature
<222> LOCATION: 1- 454
<223> OTHER INFORMATION: n = g, a, c or t(u)

<400> SEQUENCE: 89

```
aattcatccc tcatttgccc tgctagtgaa aactatttca gacctgaaga caacatcctt      60
gaaaacttct ctggagaatg tgcagagatc accatggcaa cctgtcccgg gccctgcctg     120
gcagggctcc aaggcacaca ataacgcca ctggaatgtg gtgcagggct ccgggtgggg     180
tgactagaaa agctgccaat tttccatgaa accaccggt gagaagcctc agcctcagga     240
aggtgtcagt agagagggct gggttctctc tagcaccaag ggacaggctg tgcgcaagca     300
tgcgcagaag cacactcacc ggcctccttt ggggcagggc tgcctgaaat gaaccggctt     360
cagttttgtg cagctcaagg gcacaaggnt agtgcccttt ncttggncnt gaggcactnn     420
taaatgtagg ttgggcgcgc taanaaagat ccnt                                 454
```

<210> SEQ ID NO 90
<211> LENGTH: 873
<212> TYPE: DNA
<213> ORGANISM: Rattus norvegicus
<220> FEATURE:
<221> NAME/KEY: misc_feature
<222> LOCATION: 1- 873
<223> OTHER INFORMATION: n = g, a, c or t(u)

<400> SEQUENCE: 90

```
gttgttattc aatcatccac atttgtaaaa acacacttcg ggtcctcctt gtgtcnggca      60
gtaccatcca ttgagtttca ggaagcagaa gttttaaaag ctnccagcan cntttaaatc     120
cacagctcaa gttgttgaac accttgggaa actaccactt attcacccag aggagagttg     180
attcaagtag ttagtaccnt tntgcatcag aanccaccag ntactgccgg tgagagtcgg     240
taatnccang aactcatcca tgcaggcaaa tttaaggaca cacggcttga cacagagatg     300
gttanatcgg ctgtgacagt tctttagtgg gagactttg ctttctgaat ccacagggct     360
tactttcttt cttttctt ttaagacaag ctctcatttt catcttgaga aaatgtctga     420
tcaagccacc aactgaaaac ctgccattat aaacgaggga tttcacaatg ctcattccaa     480
aatctgcggc tattcatttc tggaagtgac tcactgagga aggacggctg ttgggggtgg     540
gagggagaga tcatttttag gagaccgcct gctctctgag aactgagcag aaacccagaa     600
gtggctagca cgtgtgtgca gcgaccccag ctcagctctc tgagtcaccc cctcccccag     660
atgacacgcc atgaccagtc tcctcgtgaa agccacttgg tggacaaaaa gcccttttggg     720
ctgtgcaccc agcctcacat ctgcctctct ggggctatt ttcacataaa tcaggaggga     780
ggcagcagca gttgcccacc tgttttngac tccgattgct tggggantga aggactttnt     840
naatgtaggt ttgggncngc tnaaaagatc cnt                                   873
```

<210> SEQ ID NO 91
<211> LENGTH: 876
<212> TYPE: DNA
<213> ORGANISM: Rattus norvegicus
<220> FEATURE:
<221> NAME/KEY: misc_feature
<222> LOCATION: 1- 876

<223> OTHER INFORMATION: n = g, a, c or t(u)

<400> SEQUENCE: 91

| | | | | | |
|---|---|---|---|---|---|
| gttgttattc | aatcaattct | gttgctttgg | nccangtcaa | acagcccatc | cgggatgtga | 60 |
| ntatnggaac | taacccattt | atcctacagc | caggaggaaa | cccaanggga | ggctgaggaa | 120 |
| acggctgtgg | nttcataaaa | ctctttgaat | cataccttgg | gtgattcaaa | tgcttttac | 180 |
| taggctctcc | ttcatagtac | ctctctgtgg | acaaagaccc | agtccctttg | aaaagcattg | 240 |
| aaactcaaac | cataccacta | tcagtttcag | ctttaatata | aattagcttt | ctaagttcag | 300 |
| ctgaccacct | tttcactgga | ccttcactna | tctcacaggg | aagatatatt | ttcaacaatt | 360 |
| acaaagacat | ttctggggttg | gactatgcat | tcctttggcc | agattctaca | tcctttttt | 420 |
| atgccagaat | ttttagcgt | tcctgtaaga | ttgtcagttt | ccctaggaa | atccataaag | 480 |
| ctttaaatgc | cttctaaata | gccaatattt | taatgagaaa | tgtagtcact | gatatctctt | 540 |
| tgtatttaaa | ggttattttg | agggagttg | cttggttggt | tggttggttg | ttggttggt | 600 |
| tggttagttg | gttggttttg | gctttggttt | tctgtcccat | ggtaatatga | tacttatgtc | 660 |
| atagattagt | taactcaaat | ggtcttttca | ggtggcagtc | ttgaaaacaa | ctaacttggg | 720 |
| gggaaaaagg | ctgctccatg | ttctataaaa | gctgtacatg | tgatttttctc | tgctttacct | 780 |
| tttatactca | tttattttgt | tatttntgta | tgaaagcct | tccgtcctga | aagaccttta | 840 |
| cctgtaggtt | tggnccgttn | aaaagatcnc | tgggcc | | | 876 |

<210> SEQ ID NO 92
<211> LENGTH: 459
<212> TYPE: DNA
<213> ORGANISM: Rattus norvegicus
<220> FEATURE:
<221> NAME/KEY: misc_feature
<222> LOCATION: 1- 459
<223> OTHER INFORMATION: n = g, a, c or t(u)

<400> SEQUENCE: 92

| | | | | | |
|---|---|---|---|---|---|
| aattcagaag | gatctcagaa | attgaaagca | tgtgcaaaga | taaagatttg | gggtagtagn | 60 |
| agtggtcaaa | agggacaagg | taataatggt | aatatgcttt | tgtgtatgtg | ttcttttaga | 120 |
| gttatgttaa | aatctagaga | agcaaagtcg | attctcatag | atgcttttag | tctttggacc | 180 |
| ctgactagag | acagtttaca | ccctagacaa | gagagagaat | ggggttgagt | aaaacagtcc | 240 |
| tcccgaactc | tccacagatg | ctttggcaaa | agaaggaaat | gagcttaaac | tttttggagc | 300 |
| tctcctggga | acagaaggag | gtgggagacg | tcttgcctcc | ttgctggctc | ctattggaga | 360 |
| agtgcttatt | tctggttntg | ggttttttag | gtngnttgtc | tgggttcctn | gggncctgag | 420 |
| ggcacttnna | aatgtaggtn | tggcgcgcta | aaaangatc | | | 459 |

<210> SEQ ID NO 93
<211> LENGTH: 3133
<212> TYPE: DNA
<213> ORGANISM: Rattus norvegicus
<220> FEATURE:
<221> NAME/KEY: misc_feature
<222> LOCATION: 1- 3133
<223> OTHER INFORMATION: n = g, a, c or t(u)

<400> SEQUENCE: 93

| | | | | | |
|---|---|---|---|---|---|
| acccacacnc | cnancnacac | ccacacacca | anccacaccc | acacaccaaa | ccacacccac | 60 |
| acaccaaacc | acacccacac | accaaaccac | acccacacac | caaaccacac | ccacacaccc | 120 |
| gagtgtggtg | tgtcctcctc | actgagtgtc | agccagccct | ttcctctact | tcaggtaaag | 180 |

-continued

| | | | | |
|---|---|---|---|---|
| gtttctccac | tgcctcactg | tgtccctgtc | acatgggcac | aaagccatct cagcagtcct | 240 |
| tctcaaggac | gtgggtgcca | ggtttggaag | ctggaatgcc | tacatctaaa atcttggcca | 300 |
| tgacttgtga | caacttacat | atacatagac | atatatacat | atacagctta catagacgca | 360 |
| gagcctcaga | ctcctctgaa | gaacgggttg | attctgtgct | ctgcagagat gctgggagag | 420 |
| tgtataaaaa | ggtcaagaaa | gcaggcttag | aaagaagggc | aactctacct agtgtctcct | 480 |
| tacaattttg | ttttacgtcc | tcttctgccc | acagagccct | aagacactc cctactttct | 540 |
| gcatcattcc | tggtgtcttg | taggaacaag | ttagtgaatg | atcactctgt aaacacatac | 600 |
| ctacaggtcc | tccttacctt | gggctctgga | acaccggtg | aagtctgtgg gtaggagggt | 660 |
| ctggctgagg | ttgagtgtat | caagtaatca | actggcagta | ccctntgggg agtggcctgt | 720 |
| ggtttcctgc | tccctctttt | gggtgagaaa | tcctagggtg | gtgggagcca aggcttaggc | 780 |
| aaaggttcag | gcacagcagg | gtgtgggagg | gagtgagact | atagtagagg tgagtggaag | 840 |
| gtatggattc | gaagactttc | ggattaaaaa | aaagcaaaa | aaaaaaaaaa aaaaaaacc | 900 |
| aaaaaccaaa | acaaaacaaa | aaccaaaaa | acaaaacggt | ccaaccagtg agatgtggct | 960 |
| tgctctgagt | tgctaattat | gcagggctta | gatctcaaaa | acagtctgtg ctctggggcc | 1020 |
| actgctgaca | tccaagtcag | gcccagaagc | tcttggtctt | catctttcct ttccctctca | 1080 |
| ggctgcttga | agctgattga | ggtattcctt | gcttgttcag | ccggttcntg atggtctccn | 1140 |
| tgttcntccc | agttctctcc | atgtttcttt | tgctttgaag | tacaaaggaa tacagttgca | 1200 |
| ggggttacat | ggcactcccn | tattcacttt | tagggttacc | acaaaagctt gtgattcttt | 1260 |
| ccctcnttag | gactgagctt | ctaccccgc | acacaggcct | aactttggtt tccccaccca | 1320 |
| taatgggca | cccaccccca | ccnccgcccc | accccacccc | aagaaaaaga aaaagaaaa | 1380 |
| agaaagaaat | gaaacggcca | gctggctctt | acccactttg | ggcagcaggt gtttcctccc | 1440 |
| tagcttccct | tttgcatctc | atacttgttg | cttgcacacc | ctcacccctc tcttgctgcc | 1500 |
| tttttcaaat | taatagcctg | caacttccct | tgcatataga | gaatggttcc caggttctta | 1560 |
| ctgggattag | tgaacgctct | ttttgttgag | gaaatgcttt | taacaccacc aagtgctgta | 1620 |
| cccctcaaag | ttggtgaagc | tctagattca | ntgggctgta | caagggacac ttgggaaaaa | 1680 |
| tttgaacagg | acaagcctga | gggtgtgagt | ggggttggct | catctacaca ggagctgcga | 1740 |
| ntgagaggga | aagggccccc | aaacatcttt | gctaccactg | ccttcttaag tttggggact | 1800 |
| tggaaatccc | gttgtttaga | tcttgaccgt | aatcaggagt | cagcgtagag gaggccccgg | 1860 |
| aaggagggcc | cagcgcggat | tcgcccgcgg | cagggcgggg | accaacagag ggccntcggg | 1920 |
| gataggggag | cgccgccccg | ccntcccggg | gaaggacaca | ttgcttgtta gcaggaagcc | 1980 |
| agccagaccc | ggaggaggcc | gctccagcgt | tggtgttgcc | ggtccggggc tagcctgatc | 2040 |
| cgggcagggt | gagttgagac | gatcgggtga | gcttgggccg | gggacgccag cgtcttcagt | 2100 |
| cctgggatt | gtcccaggag | ggcaaggagc | ttggaggagg | gaggccgcac agctagggga | 2160 |
| gtcaggtctg | agtcccgagt | gtgctctaaa | gccggggcgg | tgagagtggc ggcccgcccg | 2220 |
| ggccgcgca | gcgngcagtc | tcccccgcgt | gggaagtggt | aacttaacgc acagccacag | 2280 |
| gattcccggc | ctttagctgc | tggagggagg | gtggcttctc | ccggaggagt ctgttgtgaa | 2340 |
| actcggttgg | agggcaccgt | gggtgcgggc | aaggagaga  | tggggtcgcc ctgaagaagt | 2400 |
| gggggctgg  | agtagaaagt | ggactttgtg | caaacctcac | cccagagtag ttagttacca | 2460 |
| aggctggttt | tttttttttt | tttttttgc  | tcagacacaa | ggaaaatttg actcaatgtt | 2520 |

-continued

```
aaaatatgta atttggcagg aaaactttt  tcctagcctc cttgctaata tagttggaac    2580
agggggctcc caagaggtat agagtccccc attttacaaa atgtggttca gtgggactgt    2640
ggcccaccca gtcgtgtatc catggaagag tggcttttat ggagaagttc attttcctta    2700
accttaaaaa ctgtaaagga tcttgtgctt gagaatattg ttggccagct ttatagtctt    2760
catttataaa actatttaga ctagagtgtt atagattata ggtcttcaag tttccagtca    2820
ccagtccttg gctttttagt atggaaatca ccagtaatgg caatataaca tccctgcttc    2880
tgtttcttag aaggctaaat tacagtgtgt tcaaactccg tgtcattgca acaggttaaa    2940
ctaactttat acgtaggaca tcagggtatt gacattctca tcctaaagtc agtttgtctg    3000
tttccagagg aggaactgaa gcagtggttc tttaagtaac tgactcaggg ctttcctgcc    3060
tggcgcgcct gccaggcata gtgtagcatt gtactgcatc ttctttgacc agtttcccca    3120
ggtgaagagc ctg                                                       3133

<210> SEQ ID NO 94
<211> LENGTH: 2161
<212> TYPE: DNA
<213> ORGANISM: Rattus norvegicus
<220> FEATURE:
<221> NAME/KEY: misc_feature
<222> LOCATION: 1- 2161
<223> OTHER INFORMATION: n = g, a, c or t(u)

<400> SEQUENCE: 94
ctggaagctc ccttctcccc tgtactctac tctgcaaatc cctgcaggtg gacactgaga      60
gaagccacac acacctgttt tgttttcca tctctgaggg atctgccatc tactgtacat     120
gcagtttctg aaaacatttg tttggcggtt ttctatttgt ttactaagtt agttcagttt    180
tcatcagtgg cacaaactag aagtcattca tatgagtaaa atttgttaaa acgtcttcat    240
aaagttttca gtttgcgagg agcatacaag gaaagggtcg cttaagtgga aagggagcag    300
gctctgtggc tttctcattc taaccttgt ttgttcctgt gaggtgtgga gccctgctct     360
gctgctgtct ggacagagca gagatccttg cagcagccac agctctttac tgcagatgtg    420 ttctggggc ctggttctga ctccttcagc tcctggtagt gccctgcgtg ataataacag      480
cctcctgctc ccagctccag acagctcgtc tttctgttgc agcagcactg tgaacaccag    540
agtgattctg agcttagatt caagatgacc tcacactat gggaatcctg tgcgtggacg     600
tgttgcttsc tgtttttact gcccavgatc ttccagctga atgccagagt gttgagtgtg    660
cccarcctgg ggtarcccag cttgctccac caccctctgt ggatactcca cccagtctgc    720
tgttaccagg cactggccca gtgaaaatct aaaggtttta ttgtttagta gaaaattaaa    780
acacttacta cagtttgaat gtgttgcaca ttatggtttg aggccaaagg aaggtaggca    840
gaaggaaaac aggaggcaag gaggggaaga aagctggaga gtctggctgg agggcgatgc    900
cctcctggtt ctgaaagagc cacacccctc tgctgccagt tacaggccga tctgctgctt    960
agcaccaccc tgatgtgctc cagcatctcc cgttccagcg tggtttctgg tcgraccttt   1020
attccacggt tacttgaggg gtgtgtgtgc gtgcgtgtgt gtgtgtgtgt gtgtgtgtgt   1080
gtgtgtgtgt gtgtacatgt ctgtgtcccc atgccacagc acttgtggag gtcagaggac   1140
aaaggacact aaattgcttc tccctttcca tcacgtgggg ccctcaagct tggatcttga   1200
aaacgttact tctagtgtaa ttgtcctaaa agttcacgtg gactttaagt ctcttgttta   1260
aagtctgtag gcagttctgt tcccgcagca cagttcctca caaagccctc tgatggctga   1320
ttctttgctc ttggangcac aaggctgtgc cgtgcttaag acaggctgca cagcttarga   1380
```

```
cttgcactga gggcgttctc gcctggttgg ctcarcatct ggagtatatt ggtcatggcg   1440
agtcagggct cagctctcgg tatttatctt tcagtgcatt gatgtatttg cccttacaga   1500
cactgtacct gaattattta acactgtaat gctagtgcct gatactgaat tcatgactat   1560
aagttcanar ctgcaracac agccttaggt gttaaacagt atatttttaa gagcttcaag   1620
tgcacagaac agtaggggtg cagttttgac cccctaggtc tggactttga ggttgcatct   1680
catgaatgca gctctgagct gggggcgcca tactctacat tgtaaagtaa tgcacctcct   1740
aactacctgc catggtagca agctccagcc acctgaaaag cagccagccc tcttggggca   1800
gcactgcatg aggaagcctg aacccagca aggagcatt gggctgctat gtctgttctg   1860
ctacagcgac aaatcccagt gtgcacttgc caacagctgg aggcatgcca tagccagggt   1920
ttcagcatgg ctgcccttgg agagaggcgt gcgctgtgtg tgtgtgtgtg tgtgtgtgtg   1980
tgtgtgtgtg tgtgtgtgtg tgttagaata agcaactact gacaaattca rgarcataaa   2040
cattatggaa attttttgt gtatgtcatc attttaattt taaaagatgc cttattttct   2100
cctcttggaa ctaaagagat tatatttcac tttataaaga aaaaaaaaaa aaaaaaaaa   2160 a                                                                  2161
```

<210> SEQ ID NO 95
<211> LENGTH: 824
<212> TYPE: DNA
<213> ORGANISM: Rattus norvegicus
<220> FEATURE:
<221> NAME/KEY: misc_feature
<222> LOCATION: 1- 824
<223> OTHER INFORMATION: n = g, a, c or t(u)

<400> SEQUENCE: 95

```
gggggntttt cnnanntanc aaaaantngn tntancanng antnnttgag ntgttgaagn    60
aangnggaaa angttttgaa atcantgtaa tgaggttcca aaaattgagc aggaaattgg   120
atgntgtcag gagaaacccn ttcagtnttg tgcaattggt tcgccagcag ttaggaccgn   180
ttccccatca cttgtgccag cggacatcca gntattgagc cntgnatcat ttatggnaca   240
aattaggaac acacaacaga gatccgcttt ntgactgcca tgttcgccaa actcaattgg   300
gggaagtaat cctccagacc gttccgtttg cacgtntagg aagccacagt gaaaacacaa   360
aattcgtgga ggcgactcta accaggaagc ctaatcccnt agattcccgg gacactgggg   420
caggcgtcct aaaaacagct ttgtgggct tcagtcctcc gtgcggttcc agtccgggtc   480
ttggggatcg ccctcgcggg gaatgtccgg gactccggtc ggtatctttt tggcctggga   540
atttccagcg tgtggaaaaa gtccacaaac ttagtcctca ctgcccgcct cgcctcctcc   600
ggcccttctc ggtgcccacg cacccccga tcgaacccga ggatgagcat agggtgtatt   660
ttaggcgtgc tgggcttccc cgccccctc tgcccactta gctggcaaga agaaagccag   720
cactataaag gaggccaggg ccaaggactg gcctcctctt gctcacgagg tcagacgcga   780
gctctgaaag acttcacctg taggtttggc aagctgaaga gatc                   824
```

<210> SEQ ID NO 96
<211> LENGTH: 774
<212> TYPE: DNA
<213> ORGANISM: Rattus norvegicus
<220> FEATURE:
<221> NAME/KEY: misc_feature
<222> LOCATION: 1- 774
<223> OTHER INFORMATION: n = g, a, c or t(u)

<400> SEQUENCE: 96

```
gaggggganna ncancaggac caancngata aggggggtcaa caacntgngt tccncccntt      60
gagngggaaa tgagcacgng gcantccaac cgntcaaggt cccgnttcgg acggtcacac      120
antaggttnt catntggatt gccngngttc cngttggcat ccgggaaaan tgagactgtg      180
tcggtaccag agntaggatg gccntccttc ccngccccgg ccttnttggc gccttgcgat      240
ccttcccgaa ccggcccntg gcgtctccgc cttnggcact tgcacatntg gcggcccagg      300
atggcgcttc cgggatggcg ccagcgcgcg tacgtcatca cggagcgtcc atgtgttcct      360
tctgtccaag cgcntaggag cctgcgcgta ctcccagcaa ggaagatgta ggaccaaaat      420
gtagaagcac ttaacatgaa cgtcaaaacg atgaccaatc acaggcgat atatgcgcat        480
gcgcaatgtt ccaatcatgg ctcataagca atccggaagt ggccaattaa atatactatt      540
tactaatcca gggttacaca gtgaaaccct gtctcgaaaa ataaacacag ggctggagag      600
atggctcact gattaagaac actgactgct cttccagaag tcttgagttc aattccgagc      660
aagcacatgg tggctcacaa ccatctgtaa cagattctgg tttatgtnga gacaactaca      720
gtgtactcgt attgaaagnt ncccacctgt aggttnggca agctaaanga gatc            774
```

<210> SEQ ID NO 97
<211> LENGTH: 248
<212> TYPE: DNA
<213> ORGANISM: Rattus norvegicus
<220> FEATURE:
<221> NAME/KEY: misc_feature
<222> LOCATION: 1- 248
<223> OTHER INFORMATION: n = g, a, c or t(u)

<400> SEQUENCE: 97

```
tgacacttca tggaaactga gaccgggagc ttccaccaga aggcactgcc cagtggagaa       60
aaccgacttc tttttgttgt tgttctgatg ttttgttttt gagataaagg tctcactgtg      120
tagctcaggc tggttttgaa atcaggatcc tgaccctcag gaatgttaaa gtgcctaaaa      180
gtggngacaa attattttac gtgcctttga aagacttcac ctgtaggttn ggcnagctag      240
aagagatc                                                              248
```

<210> SEQ ID NO 98
<211> LENGTH: 880
<212> TYPE: DNA
<213> ORGANISM: Rattus norvegicus
<220> FEATURE:
<221> NAME/KEY: misc_feature
<222> LOCATION: 1- 880
<223> OTHER INFORMATION: n = g, a, c or t(u)

<400> SEQUENCE: 98

```
aanatggntt ggttntaaag gttaaaattg gggcaaaatt tttccgcccg ggtccttaaa       60
ccggattaac tccaaggcca aaattccgag ggggaatcaa caacaaggac ccaaccggat      120
taaggcgggt tcaaacaaac ttggatttcc ngcccctttgg ggcgggggaa atgggcacgg    180
gngcattcca agcngntcaa ggttccggct tgcggacggt taacacaant aggtttctca      240
tctagattgg ccngcgttgc ggttgagcat ccgggaaaat tgagattgtg tcggtaccag      300
aggtaggatg ggccttcctt cccngccccg gcttcctggc gccttgcnat ccttcccgaa      360
ccggcccttg ggtctccggc cttgggcact tgcacatctg gcggccagga tgcgcttccg      420
ggatggcgcc agcgcgcgta cgtcatcacg gagcgtccat gtgttcnttc tgtccaagcg      480
cttaggagcc tgcgcgtact cccagcaagg aagatgtagg accaaaatgt agaagcactt      540
```

```
aacatgaacg tcaaaacgat gaccaatcac agggcgatat atgcgcatgc gcaatgttcc    600
aatcatggct cataagcaat ccggaagtgg ccaattaaat atactattta ctaatccagg    660
gttacacagt gaaaccctgt ctcgaaaaat aaacacaggg ctggagagat ggctcactga    720
ttaagaacac tgactgctct tccagaagtc ttgagttcaa ttccgagcaa gcacatggtg    780
gctcacaacc atctgtaaca gattctggtt tatctggnnt cnactacagt gtannggcat    840
tgaaagatnn tacctgtagg ttggncagct aaaaaggatc                         880
```

<210> SEQ ID NO 99
<211> LENGTH: 864
<212> TYPE: DNA
<213> ORGANISM: Rattus norvegicus
<220> FEATURE:
<221> NAME/KEY: misc_feature
<222> LOCATION: 1- 864
<223> OTHER INFORMATION: n = g, a, c or t(u)

<400> SEQUENCE: 99

```
aattttaant tgttggnata anggcttgnc catatccttc ctnttgtttg ccctaagtaa     60
cagccaattg ggggagaant tttntgtcag tatcatattt ttcgttaggg aacggaggcn    120
caggaantga tccntntggg ttacagtcat tttagcatag gntgacagtt ggngaccaan    180
tnatcttgcc gtgttggaag gagagggggan taaggntgaa gctcttgagt ccnttgangc    240
ccttggaatc gggaantccc ttaaaccaac ccctttgcc gttgaattgc accaaccaga    300
ttcttccagt ctgcttgagg angacaggac ttcattgctn tggagagggg caggagggtt    360
gggagttgac ntnacagggc tcagggattc ttttagaagg gtccaggttc atggcttccc    420 cccccccag ccaggtcaga cactaaagtg tcttaagccc ctccatactt gccgctcccc    480
cacnttggat gaagccggcc attaggcagg gaccgtctct gggagaggcc aagccctctg    540
gctcacttgt ggatttcctt taagcaagac ttcctctctg cttccaggac tcctgtcaaa    600
caagagggtc cctggcttag agtttgggag ctgcaggcag aacagacatt ccccgatgac    660
tcacaagcct ggaactctgt gggccagcag gaatggggat ggctttctgg tcagtcaggg    720
tcaactggga cactcactct gagacaggga ggcaagggag aaacaggtca gaggtagaga    780
gagctcagtc ccaggggactc acgttgaggt ccctaaggtg cgctagggag aggnttttac    840
attcggttng gcaagctaaa agag                                          864
```

<210> SEQ ID NO 100
<211> LENGTH: 874
<212> TYPE: DNA
<213> ORGANISM: Rattus norvegicus
<220> FEATURE:
<221> NAME/KEY: misc_feature
<222> LOCATION: 1- 874
<223> OTHER INFORMATION: n = g, a, c or t(u)

<400> SEQUENCE: 100

```
gaggttggac cacaaggagn ttggnggaaa atnnaaaagt caacctatca gggtgtcttt     60
tagtttggaa cagaggcttg ggcagaaata tgggcaagta ttaggaaagt acaaggggaa    120
atgttgtcaa cgcgnttgtt ttcccagttg ttgnactgat ccnccagga tgttttccca    180 cntatgntat ggaaccntct ctttcaggaa gccattntna ncntatggnt tgcaacccct    240
ttggggtcgc aacagcaggt attaacatta ggattcataa cgntagcaaa atncagtta    300 tggagtagca atgaaataac tctatgnttg ggagggtcac cacaacanga gggacggtat    360
```

-continued

| | |
|---|---|
| cacaggnttt tagcattagg aaggttgagg accttatttc agagtgtcnt gacaatcntt | 420 |
| cntgggacca cttgacttna tctggagccc tttccctcac gctcntactc cttaccatct | 480 |
| ctgcacagct ctntgaggct tagagcggtc tttcttcata gctttccntt ttccttcagg | 540 |
| tatgcagtca catcttgctt tagaccccag ggacattccg tgtctgactc actgcacaaa | 600 |
| atagtttccc acatatgagt cctcaaccgc cccacatcac gagacggaca agaccggaga | 660 |
| cgccatacat tctgtatttg ccctccttcc tcatttaaat aggaatttgt tgctgtttaa | 720 |
| tttttcatta tttgtgtgtg tgtgtgtgtg tgtgtgtgtg tgtgtgtgtg tgtgtgtgtg | 780 |
| tgcgcgcgca cgttaatatg ccgctcagaa tagtctaaaa ctgctgggct tgaaagacnt | 840 |
| ncacctgtag gtttgggcna gctaaaagag tatc | 874 |

<210> SEQ ID NO 101
<211> LENGTH: 886
<212> TYPE: DNA
<213> ORGANISM: Rattus norvegicus
<220> FEATURE:
<221> NAME/KEY: misc_feature
<222> LOCATION: 1- 886
<223> OTHER INFORMATION: n = g, a, c or t(u)

<400> SEQUENCE: 101

| | |
|---|---|
| atttttnaat tgcagcaatc ctcctgcctt ttttcttggt tgttaantca caggatnttt | 60 |
| gcacacttga ggttgaantt gcagcaatcc tcctgctttt gtttnttggg cgcttggatt | 120 |
| atagtatgtg cataacactt gagcagtaac tgttttcttc aatctcattt atctcagaag | 180 |
| ttccccttgn tgattcagac gttattaatt aggcaaacca atgttgattg tcattaccca | 240 |
| tgagttgctt ggcttgtgag atgcatactg tgtgttcgtg aggcacntac tgtgaggcat | 300 |
| gtgcccgtga ggttcatggc tgtgaggtgt gtgcccgtga ggttcatggc tttctngacc | 360 |
| acngggagta tgaaggagag gaatcctacg tttgatgcca gccagggtta tacagcaaga | 420 |
| tcccgtctca aaacaaaatg aagaagtaga gagattagtg ttaataagca actgaggcct | 480 |
| tgaagggctg aggtcaggcg gtgccctggt gcacacacag aagcgtgcca gtgacgtcag | 540 |
| acagactcag ccctgtgtca gacaggccgg agggtgactg gccatgtggc gtgattggac | 600 |
| acattcccaa aaaggaact cgatggaaga ggctcctcnt gctccagaca gggcggtggt | 660 |
| tatgtgactt gtgcgagatt agtctcatac cctattgcta gcctgtgcct ggtaccacgg | 720 |
| acatggtaca atccagggag gagccgtaag cactacaggg gagccatcct gaatcccagc | 780 |
| aagtccaact tctgttttttt cttccttccc cgcaacatta ggaatgactt ctaagagngc | 840 |
| tgttgaaaga ctttcacctg taggttgggc aagcttaaaa gaggat | 886 |

<210> SEQ ID NO 102
<211> LENGTH: 865
<212> TYPE: DNA
<213> ORGANISM: Rattus norvegicus
<220> FEATURE:
<221> NAME/KEY: misc_feature
<222> LOCATION: 1- 865
<223> OTHER INFORMATION: n = g, a, c or t(u)

<400> SEQUENCE: 102

| | |
|---|---|
| tggaggtaaa agtcacaagn ttttcaaggg tttgagatga cagttcaacg tgagnattng | 60 |
| acaaggattg attcttgtnn acaggaaagn tccccatccc accaananac accgtgttca | 120 |
| ggcccantgc tcagagctcc gggcgccagc gaagggcaaa cggccactga ttggaaagnt | 180 |
| gcagtttaaa gacatgtccc aggaactggt anccttgtgt gactggactt agccttgcaa | 240 |

| | |
|---|---|
| ntctgtctga agcataacnt gntgctgtct ntgggcgagc atttatgtgc cccacttgag | 300 |
| acccatctca ggacacgcag gacacggtcc agtggagctt tccctccaga gagaggtgtt | 360 |
| agggnccatc agtgagcttc caaggacagg ggaccagaac ggtgaaaaca aaccagggct | 420 |
| gtgaaggaga gcagggcggg ggggggggga gggggggcgc tctntagaat agattgaacc | 480 |
| tgcagagctg cttgctacct gaagttgtca ccctttacc cacccacntc atctgtctct | 540 |
| gcttgaccat ctcagcaagt gtcacctcgc tgccaggaca caagtttcct aaagcttatt | 600 |
| tcagtgtcag ccgctgggga gacacattca gggcatgggc gtcccccagc cctcggggag | 660 |
| aatgtgggag gtggcgatgt gggagggatt cgagagaaga gaatgcttaa gaaccatcca | 720 |
| gggaacctgt gcgtttgaag gtctgagtta cacacaggct gctcaggaag gagctagagc | 780 |
| tccaaatagg agctgtgatc aggctgtgtg tgtgtgcctg gtgaaagact ttnacctgta | 840 |
| ggtttgggcn agcttgaaaa gtatc | 865 |

<210> SEQ ID NO 103
<211> LENGTH: 859
<212> TYPE: DNA
<213> ORGANISM: Rattus norvegicus
<220> FEATURE:
<221> NAME/KEY: misc_feature
<222> LOCATION: 1- 859
<223> OTHER INFORMATION: n = g, a, c or t(u)

<400> SEQUENCE: 103

| | |
|---|---|
| cangagcant ntgaancagg catttntgga agggctccng agaaaacacg tggaattnct | 60 |
| tgtctctggg actttagtnc cagcnaggan gatncagtga gggaacacac cgggcttttg | 120 |
| ttgtgcacgg gaggccaggc tcancnncct tgggagnttg acatccagca ggctatanac | 180 |
| agtgatccag gggacatgta cacatgggga actgnccagg cagagaaaga caagagaaaa | 240 |
| tctcaaanga tgaagacaga gangagtaat atggccagaa ngatacagtg cctcntgcat | 300 |
| aacccttgag tttaatttcc aggtcaact gtattttgaa agtataaatg aaagttcctg | 360 |
| aagtaataaa tttataggat gttagtatca cactgttcag aatagctcaa aaaatcctgc | 420 |
| cntgtcctct taagtatgtg aatcatcttt tactgcaacg tgtccacaat gtatatacta | 480 |
| catacccaaa agtcctcact gttatcccaa ttagtaggct ggctgccaat agttgtccat | 540 |
| acagagtgcc tgctgctgtg gccatccnta ctgtagtaaa cagtcatcca aagctcagga | 600 |
| gtgaggctat tgtagaaatg cacttcctgg gggccctact gtcagtgagc acctgagaga | 660 |
| gaaagggaca caggcccaag gtgggaggcc ttagataaag gcccatcatg ctcaggaaag | 720 |
| gatttntaca gatctcttag ggaagttaca atcaaattca tacctcacag cagagctcag | 780 |
| gagaagaatc cataaagnnt gaagacatgc ttgtngtgnc tgaaggacnn tacntgtagn | 840 |
| tngggccngc tgaaatttt | 859 |

<210> SEQ ID NO 104
<211> LENGTH: 883
<212> TYPE: DNA
<213> ORGANISM: Rattus norvegicus
<220> FEATURE:
<221> NAME/KEY: misc_feature
<222> LOCATION: 1- 883
<223> OTHER INFORMATION: n = g, a, c or t(u)

<400> SEQUENCE: 104

| | |
|---|---|
| gggggggnnaa naatttccca aaaanngnng gncccntttt ttatccagtt tnnggttgaa | 60 |

```
natctcnccc cggttttnaaa acccncaatg gggaaaaagg tacancngat tntttatngg      120
tttgggcgga gggggaaatt tttttggttt ttttntttnn gggattttttg aaaaaaaaan     180 gaantttta ggtttcccnn angtaattta tttcaatgga ccattttttgg ggttctccct     240 tttgtaanan gttaaaaana aggganttcc aannttnctt ttcagtttcc agtttcacct    300
tcngtagcag acccagtttt cattttgagn tggtnccnaa aaggnttccc aactatgttc    360
aataccacag gcagcctgca ggagggagaa tgggtatgta tttaacagca tttgaccaaa   420
ttataagagc agagaggagc tttaccaggg acaggaaggc aaaagagctg aatnttaaac   480
aaaagaataa gaacaggatn tcatctgtga gctgtcacag tgggtttgca gagcaggaga   540
acacagacag gattagctat aaagttgtta cattagttat tntattggag catacaatac   600
ttaaatagtt ctagggcaag agaaatgaac agaaatgacc ttataagagc cagagctgta   660
gccacagctt tctttgtgct tagtttgnta gttcantctt tccagggcag tctggtggat   720
nacaccaaat tgctttagaa aatgctagnt ctactgtccc tgtctattgt cagctttgca   780
atgtgcatag tgacaggagt tgcctgggag cttggggctt atgttttgca gatccattgt   840
aattaaaaaa gaattgtaag gagatggagg cacggggtga ggg                      883

<210> SEQ ID NO 105
<211> LENGTH: 987
<212> TYPE: DNA
<213> ORGANISM: Rattus norvegicus
<220> FEATURE:
<221> NAME/KEY: misc_feature
<222> LOCATION: 1- 987
<223> OTHER INFORMATION: n = g, a, c or t(u)

<400> SEQUENCE: 105
canntttccc ntanccgaaa nttttnttttt ggcccaaccn gtaagacgga ttttttncaa     60
ttgcggancc aatggaaccg gtttgccggg nngtnttttg gggtgaacgg tttnttaant    120
ggngccaaan aagttnatt ggaggncnta tttgaattgg tntgtaaanc ntttncttgg    180
aaaaggnttg tagcnttaan ccggcaacaa accaccggtt gtacggtgtt tttttgttgc   240
agccgcagnt tangggcaga aaaagaattc aggagatcct taancttttt nttcgggntc   300
tgacgctcat gttgtgtgga tttntgagcg gttacanttt nacacggaat tctattcact   360
ggcatgactc acttccccgg gttcatgagt cagcagtgag ttatctaggt atgtgttttg   420
tgttgcaaat tcccatatat agaatatggt cccggggacc atagaaagtt gagcagttgg   480
gcaaaattct tccccaggag gtgtgttcaa gagaagaggt tcagcccttg aaagagcttc   540
cgtttctatc ntcacaaaca tcntgaaaaa taggctaaat gttattctgt gaagagtcat   600
tactggtttt actgatggtg gaagttctca gactgtctag aaaggtaatt ttaaaacgta   660
agaaaattag accccctgtcc ccagatctgt tggtgttgag aaatctgtag aaacttgagc   720
aggaggaagt acaagaaagt atgtagctat tgtaatccct ttcaggaagg atgtgtttaa   780
agctctattg ttagggcctt tcgcttgcac tgtgaagtaa tttttttactt tttataagct   840 taaaggatgg cttaataaga cgtcttagaa atgtccacat tatattggat caacaaacgc   900
caaagcatca gtttgcgtca ggggccacgg ggcatgggga ctaacggttc attctttttgg   960 aatctggatg cctaggtgca gtagggc                                        987

<210> SEQ ID NO 106
<211> LENGTH: 1031
<212> TYPE: DNA
<213> ORGANISM: Rattus norvegicus
```

```
<220> FEATURE:
<221> NAME/KEY: misc_feature
<222> LOCATION: 1- 1031
<223> OTHER INFORMATION: n = g, a, c or t(u)

<400> SEQUENCE: 106
agtcctgccc ccntgggaag ggtaaccttg acctaacccc cnaataantt ncccttagga      60
ttgcttggca tggnttttac gcgtaaccct antaaaactt tgangaaant tccttcccctt    120
tgattctagc aatgnaccgg cattttgcca atcnattcng ctgnantaat tatgaagttc     180
cggtttaanc aatttgaagt ttaacattca tgtatcttca cagtcatgtg tttttgtgta    240
tgatgaaacn ccatgctgtc ttgcnccatt tgntcaggan tgagtcattt gtctagcntg    300
nccatgctgt atatgctacc natccatcag ttattcatag ccagcttggt tgtngactaa    360
caacagtagt ttcacantgc tttgtgttaa agtcaccttc agtttattta atgttggcac    420
caaagcacat gntagtgatg tcagcantgc tgatatgcca gggaaaagcc attaggtatt    480
cctttatgtg taaaggttga aaattgttga ttgaatgaag ggaaaaatta ttctgctgat    540
tgatgttggg aagggcatta gaggatcata ttactagttt ttgactaagc tctgaagttt    600
gtacatgaat ttatggatcc tccctgcaat agattcctga tgctctctaa catccatctt    660
ctcatatgac atccttctgg ccagatatct agctttattt tctctactct gctgcaccac    720
tgcctctgcc tttggggatc agtccccata gaatgggagg aaaacaatgg cctccttaga    780
ccatgaatgg ccttctctca gtaccatgaa gaatcgggcc atcttgtcag agggaaattt    840
tccttacatc ctcagtcact gtttctgtca ccattataca ttatatgttt gcctaagagt    900
gagggtgatt tgtgtagtaa ggaatgtatg tgttgttgtg gtagtttgga tgagaacggc    960
tccccaaagc tcatgtattt gaatggntat gaaagacntt cacctgtagg tttggcnagc   1020
tagaaagagg a                                                        1031

<210> SEQ ID NO 107
<211> LENGTH: 1138
<212> TYPE: DNA
<213> ORGANISM: Rattus norvegicus
<220> FEATURE:
<221> NAME/KEY: misc_feature
<222> LOCATION: 1- 1138
<223> OTHER INFORMATION: n = g, a, c or t(u)

<400> SEQUENCE: 107
caancaccnc ncggananga ncccggnnga anngagaccg gncanacacg acgngancag     60
cgaagncanc ncgnnnnngg cncgncagag cgnncgancg cgacnanagn acgncgccga    120
nangannnaa nccggngnna ncanncagnn gggaaacagc ccagagagat aggacancaa    180
acnaganagn acacancgng acgaganann ccgaaagnnn nanacnnana nanaannaag    240
agaanagnnc aacnnnnnca nnnngaccng gaanagggnn nnngaacngc nancnnccna    300
gnngcgngan cnanacacga cngaagagac gngngcngaa naganacncn gaanngnaac    360
aagangnana annngacagg aancacnnag naggngngng gcaagcgcaa ngnnngaaaa    420
nnnacaacag aaaaagannc anancanaag ngncgagagn annagaanna gngaaanncg    480
nanncgcncc gaagaagaac gnnggacaaa naccgacgna ncnnnnncan ngannaaanc    540
gcangnancn gacnaggaac gacngnaagn gcnaagnnac ganngncaga nnanangaaa    600
cacgnnnnan acannnaccn ancgcagcgg nncaggaaag nggngcnacn gaggngngcc    660
aanaaganaa nngngnagan n acaaaaaaaa nggnggncan gcagnanaaa accgagnncn    720
```

| | |
|---|---|
| nnnnnannna gaganagaac gagannnang nncgaannac gcgnacaaga angggaannn | 780 |
| cgnangacgc nncggaacaa ngaccnnnnn aaanncagnn anccaacnag gnaannnaga | 840 |
| nnnagngncn ccanngcaag cncncacnaa gaagaagana cccccccccn annangnagn | 900 |
| aagcnccncc ngngaggnaa cncgagaccc cccngnaggc agcancgcca agngnagcgn | 960 |
| ncagagnacn nanntaacag accgaaggaa nagccgnaaa acaccaaana cnagacnacn | 1020 |
| agcnagnccc gcgcacnnng gagnaancna ccnncnaang acngananacg nggnccncgc | 1080 |
| tnttnngttn aacgcancnn ggggcggccc nngggaaacn cngggggaca aaaggcgg | 1138 |

<210> SEQ ID NO 108
<211> LENGTH: 1072
<212> TYPE: DNA
<213> ORGANISM: Rattus norvegicus
<220> FEATURE:
<221> NAME/KEY: misc_feature
<222> LOCATION: 1- 1072
<223> OTHER INFORMATION: n = g, a, c or t(u)

<400> SEQUENCE: 108

| | |
|---|---|
| cccttnaant gggncccccaa ngggnntccc ccccagggt tcccccccccc cctaaanttg | 60 |
| cctttntaac ccagggntgg nnnnntggaa tttttgaann tggaggntcn nnngnaacat | 120 |
| tnccgggatt tttgaggagt ttgaatgacc ggaattntac tttttgggtt ccggcnggca | 180 |
| ccccnntccc ccaaggttna gngagttttg aaggtaaaag tcacaaggtt tttaaagggt | 240 |
| ttgaggatga cagttcaacg tgaagatntt gacaangatt gattttgta nacaggaaaa | 300 |
| gntcccnatc ccaaccaana aaaccgtgtt naggcccaat gttcagagct cnggcncca | 360 |
| gggaagggca aacgcccaat tgattggaaa gctgcagttt aagacatgtc ccaggaattg | 420 |
| gtaccttgtg tgattggact tanccttgca actttgtttg angcataact tgntgtgtct | 480 |
| ttggggagc atttatgtgc cccacttgag acccatntca ggacacgcag gacacggtcc | 540 |
| cagtgagctt tccctccaga gagaggtgnt agggtccatc agtgagctnc caaggacagg | 600 |
| ggaccagaac gttgaaaaca aaccagggtt gtgaaggaga gcaggcggg gggggggga | 660 |
| gggggggcgt tctctagaat agattgaacc tgcagagctg cntgctacct gaagttgtca | 720 |
| cccttttacc cacccacctc atctgtctct gcttgaccat ctcagcaagt gtcacctcgc | 780 |
| tgccaggaca caagtttcct aaagcttatt tcagtgtcag ccgctgggga gacacattca | 840 |
| gggcatgggc gtcccccagc cctcggggag aatgtgggag gtggcgatgt gggagggatt | 900 |
| cgagagaaga gaatgcttaa gaaccatcca gggaaccgtt gcgtttgaag gtctgagtta | 960 |
| cacacaggct gctcagaagg agctagagct cccaaatagg agctgtgatc aggctgtgtg | 1020 |
| tgtgtgctgg tgaaagactn ccacctgtag gtnggccaag ctaaatgaga tc | 1072 |

<210> SEQ ID NO 109
<211> LENGTH: 1094
<212> TYPE: DNA
<213> ORGANISM: Rattus norvegicus
<220> FEATURE:
<221> NAME/KEY: misc_feature
<222> LOCATION: 1- 1094
<223> OTHER INFORMATION: n = g, a, c or t(u)

<400> SEQUENCE: 109

| | |
|---|---|
| ggtttngggt ganatcctcc caatgccnan aanttcccctt ttttaagatt tttttttttcc | 60 |
| gggaaaattn taaaantttt aactggggtg gnaaataata aggntgtttn tggggttggc | 120 |
| ccaattttg nantttagga aaagttctttt gggtnaattc cagcnttgat tggaggagca | 180 |

```
attatnttgt tanaanttat ggttgtgggg atgcttgtta aatcttttag atgtttcccc    240
ttctgtctcc cttttggaat ggtcttaata ggttgcnaaa attntacntn ttggatcagc    300
tttttnatna gatttagccc agtgtgctna ncttgtgaga cccntttnac agganttgct    360
tggnccattt gaaacacgta tttatgtcan gattcataac agtngcaaaa atatagttat    420
gaagcagcaa gaaaatcact ttatgnttgg aggtcaccac aacatgagga atgtattaan    480
cgcagtatta gagagttcga ganccactat cttngaggat gcgttagact gatgtttccc    540
ttctcgcttg gagttgacnt tgccantaga gggcaacagc atcagtattg ttcccagtcc    600
ccntcacant gattcgaact ttaaggacac tgatctctgg ctggtagagg gttcagcaca    660
cataccagag ttacgagtca cgtgccagaa gggcaaactg aacacggaat tagagggaac    720
tcgatgtctc cggcttgcac tggtcttctc ttgcactaga atcnttcatc ntgctcccag    780
tccgggacgt ccaggcaaca agggcgtgga aagtgagggg gctgggaggt gtgtttgcct    840
tgcctcaggc gctgggtggg gttggggcgt gccagcactc cctgggcggg cctcaccgat    900
gctggccact ataaggccag ccagactgcg acacagtcca tccctcgac cactcttttg     960 gcgcttcatt gtcgagtgtg gtgagctctc actgggcgt ccctctaaga tctgtccact    1020
cctggtttta ggggttaagc ctttcgtgcc cctgaaagtt ncccacctgt agtgggccaa    1080
gctaaaatga gatc                                                     1094

<210> SEQ ID NO 110
<211> LENGTH: 1107
<212> TYPE: DNA
<213> ORGANISM: Rattus norvegicus
<220> FEATURE:
<221> NAME/KEY: misc_feature
<222> LOCATION: 1- 1107
<223> OTHER INFORMATION: n = g, a, c or t(u)

<400> SEQUENCE: 110
atctcattta gcttggccca cctacaggtg gganactttc aaacctgtgg gagacccctt     60
tcacaggaat tgcctgagac catctgaaaa cacagtattt atgtcacgat tcataacagt    120
agcaaaaata tagttatgaa gcagcaacga aaatcacttt atggttggag cgtcaccaca    180
acatgaagaa tgtattaatc cgcagtatta gagaggtcga gaaccactat cttagaggat    240
gcggtagact gactgcttcc cctctcgctt ggagttgacc ttgccactag agggcaacag    300
catcagtatt gttcccagtc ccctcacac tgattcgaac tttaaggaca ctgatctctg     360
gctggtagan ggttcagcac ataccagag ttacgagtc acgtgccana anggcaaact     420
gaacaccgaa ttanagggaa ctcnatgtct ccggcttgca ctggtcttct cctgcactaa    480
aatccttcat cctgctccca ntccgggacg tccaagcaac aaaggcgtng naanttaagg    540
ggctgggaag tgtgtttgcc ttgcctcaag cgctgggtng gggtttgggc gtgccaacac    600
tccctgggcg gggctcaacg atgctggcac tataaaggca accagactgc gacacaatcc    660
atcccctcaa caatcctttg gngcctcaat gtcnacntgt tgtgagctcn cactgggggng    720 tcccncnaaa tttgtcactc ctggtcnaag ggttaaaccn ttcctgccna tcaacctctg    780
cnggctcaat ggtggaatgc actggattca aattttcggn gcccaaggaa acaaggaaaa    840
ccagggctgc tnggctgtnc aaaaaaancc caggtaagg ganccatgg gngggaanct      900 aaacngcntt tctngggggtc aagaagggtt tcccgggggg tgtnaacccc ccccaatntt    960
tggcccctca ggaggnttca ngggaaccc cattccttcc ttgccaatca aaagccccat    1020
```

-continued

| ttccttgaan ccnggggaa nntttaaaac ccnaanccc tccattntta accccccca | 1080 |
|---|---|
| atggnccngn ngnaccnttg nnntttg | 1107 |

<210> SEQ ID NO 111
<211> LENGTH: 1069
<212> TYPE: DNA
<213> ORGANISM: Rattus norvegicus
<220> FEATURE:
<221> NAME/KEY: misc_feature
<222> LOCATION: 1- 1069
<223> OTHER INFORMATION: n = g, a, c or t(u)

<400> SEQUENCE: 111

| aatttttttt nccggnaaaa ttttnaaant tttaantggg gggggtaanna nnaaggttgt | 60 |
|---|---|
| ttctgggntt ggcccatttt tgcacattag gganagttnt ttggggtaaa nttccagcng | 120 |
| ttgattggag gagcaagtga tnttgttana atttatggtt gtgggggatg ntgttaaaat | 180 |
| cttttaggat tggttcccct tntgtctccc tttttggaca tggntcttan ataggtggnt | 240 |
| caaaattcta cntnttggaa tcagcntatn tcatcaggat ttagcccagt gtgntnaacc | 300 |
| tgtggagacc cntttcacag ganttgcttg agaccatttg aaacacagta tttatgtcan | 360 |
| gattcataac agtagcaaaa atatagttat gaagcagcaa cgaaatcact ttatggttgg | 420 |
| agcgtcacca caacatgagg aatgtattaa tccgcagtat tagagaggtc gaganccact | 480 |
| atcttagagg atgcggtaga ctgattgctt cccntcttcg cttggagttg accttgccan | 540 |
| tagagggcaa cagcatcagt attgttccca gtcccctca cactgattcg aactttaagg | 600 |
| acactgatct ctggctggta gagggttcag cacacatacc agagttacga gtcacgtgcc | 660 |
| agaagggcaa actgaacacg gaattagagg gaactcgatg tctccggctt gcactggtct | 720 |
| tctcttgcac tagaatcctt catcctgctc ccagtccggg acgtccaggc aacaagggcg | 780 |
| tggaaagtga gggggctggg aggtgtgttt gccttgcctc aggcgctggg tggggttggg | 840 |
| gcgtgccagc actccctggg cgggcctcac cgatgctggc cactataagg ccagccagac | 900 |
| tgcgacacag tccatcccct cgaccactct tttggcgctt cattgtcgac gtgtggtgag | 960 |
| ctctcactgg ggcgtccctc taagatctgt ccactcctgg tntaggggtt aagcctttcg | 1020 |
| tgccctgaaa gatttncacc tgtaggtggg gcaagctaaa agagangcc | 1069 |

<210> SEQ ID NO 112
<211> LENGTH: 1058
<212> TYPE: DNA
<213> ORGANISM: Rattus norvegicus
<220> FEATURE:
<221> NAME/KEY: misc_feature
<222> LOCATION: 1- 1058
<223> OTHER INFORMATION: n = g, a, c or t(u)

<400> SEQUENCE: 112

| caggttttgg gttttccaag gncccccccc tgggggttac aaaatggcgn nnantcgngg | 60 |
|---|---|
| tgggaaccng acgggtttaa gntaccgggt ttccccntgg agtccntggg ggttcctntc | 120 |
| cgaccttcgg ttaccggtac ctgcccnctt tttcctttgg gagggtgggn tttttcatag | 180 |
| ctcagctgta gtatctcagt tcgtttagtc nttngnccaa gttggttttnt gcaggacccc | 240 |
| cngtnagccg gaccggtgcc ccttatccgg taatattgtc ttgagtccaa ccngtagaca | 300 |
| ngattattgc cattggcagc agcaatgtaa caggttngca gagcgaggta tgtaggcggt | 360 |
| gtacngggtt cttgaagtgg tgccntaant tacggntaca ntngagggac agtatttggt | 420 |
| atttgcgctn ttgttgaagc cagttacttt nggaaaggag ttgntagttc ttnatccggc | 480 |

```
aaacaaccca cngttgntag cggtggtttt tttgtttgca agcagcagat tacgcgcaga      540
aaaaaagnat ctcaggaaga tcctttnatc ttttctttcg gggtctgacg ctcatgttgt      600
gtggaattgt gagcggataa caatttcaca cagaatttct cttagaaaaa tctgtccttc      660
agaaacttaa attctgctgt tccataacag aagtcagcaa gtgactcacc ctccagatac      720
aggtatatta cctccactcc catccacaga gacttaattc tagtcagctt catgatagtg      780
agccttcatc cgtaaggagc tgtatggtat gggaagggga tacagacagg gccaggggtg      840
tttttaaacg gtaacccagg gaccacatcc attaaaaaca ctggactgtt tgtgagagtg      900
tatattcctg agcattgcct atcccttaag gtactacaaa atttgggagt gaggctcagc      960
aaactatttt aacatgcctc tcccacccaa ctactcaaga ttccccgtgc acagttgaaa     1020
gntttnccac ctgnaggtgg ggccaagcta aaagagat                             1058

<210> SEQ ID NO 113
<211> LENGTH: 1046
<212> TYPE: DNA
<213> ORGANISM: Rattus norvegicus
<220> FEATURE:
<221> NAME/KEY: misc_feature
<222> LOCATION: 1- 1046
<223> OTHER INFORMATION: n = g, a, c or t(u)

<400> SEQUENCE: 113
cannaaaann agttccaagg aantggntgc ccngaacaag gacccaaaac ntgnnnnana       60 anggggann naanggcana annnatggac gagagtnaan ancgcnangn agaagantna      120
aaantcncca nntggngccc caaatnncnc aattgancca aancnntaga ggnncccaag      180
acnaatgggc actntganna gancnggcca gaagncaagn ggggganннt catagnnaca      240 tggnanaaat aaagntntgt aaacccggan tggcaatnga aaccagcaaa gacccatgaa      300
cgtgagngan accagttgga aacaatgaan nnantgggtn antnacagga atgnggtnan      360
gacgcnnagt ganccccaaan aggcaacncc attgaaagcc ttcnccncca tggaaatact      420
gtanntaaaa caaacaaaca aatnacaaaa anaaaaaacc caaagcttaa gtggagtgcc      480
cnttccagnt agccaccnnn taagaactgt aaatcgcacc ntcccangcc agatgcaggt      540
aaggnaggat tacaggnatn tcggagggct caggagggaa tgggtcncaa nntgagctga      600
ggcncnggtg anttncgcta cntcgnaaaa aangagaagt catgtgggac gnatgtgtgt      660
aagcacagct cntgtgangt caagtcagca acantatgcc atactctgaa gacagaggnc      720
cataatagna ttgttacang atncnngact tttanaaaan caaaatccta atcctattc       780 tccgtgggcc cacacgaaac anccatccat caggatcatc tcacagttgc ctctgannnt      840
tngtnttctn ggaancntan gntntcggag ttggggaccg aactcagggc cgtgtgcttg      900
ctaggcaagc gctctaccag tgagctaaat ccncaacccc cacagntgcc tcntntgatt      960
gnaggtntcn tatcccnttc ttttgtggca agntcttctg ggccccntga aagtgaannc     1020
acntaagngg ncgccagcta agnaga                                          1046

<210> SEQ ID NO 114
<211> LENGTH: 1083
<212> TYPE: DNA
<213> ORGANISM: Rattus norvegicus
<220> FEATURE:
<221> NAME/KEY: misc_feature
<222> LOCATION: 1- 1083
<223> OTHER INFORMATION: n = g, a, c or t(u)
```

<400> SEQUENCE: 114

```
ctcccnggcc ccaaaaattn ttttanaaan tttttttttc gggnaaattt tnaaaatttt      60
aagnggggg aannacaaag nnnnttntgg gntggnccaa tggggaaaat taagnnnann     120
ttgnntgggg tgaattcccg ccntngnttg gaggaggnaa ttatnttgta gaaatttatg    180
gttgtggggg atnttgttaa atcttttgaa tgtgttcccc ttntgtttcc cttttgggac    240
atggntctta ataggtggnc aaattttacc ntnttggaat cagcctattt atcaagatta    300
gcccagtgtg ctcaaccttg tggaacccct ttaacaggat ttgcttggnc catntgaaac    360
acagtattta tgtcaggatt cataacagta gcaaaantat agttatgang cagcaagaaa    420
atcactttat ggttggagcg tcaccacaac atgaggaatg tattaatccg cagtattaga    480
gaggtcgaga accactatct tagaggatgc ggtagactga ttgcttccct tctcgcttgg    540
agttgacctt gccactagag ggcaacagca tcagtattgt tcccagtccc cctcacactg    600
attcgaactt taaggacact gatctctggc tggtagaggg ttcagcacac ataccagagt    660
tacgagtcac gtgccagaag ggcaaactga acacggaatt agagggaact cgatgtctcc    720
ggcttgcact ggtttctctt gcactagaat ccttcatcnt gctcccagtc cgggacgtcc    780
aggcaacaag ggcgtggaaa gtgaggggc tgggaggtgt gtttgccttg cctcaggcgc    840
tgggtggggt tggggcgtgc cagcactccc tgggcgggcc tcaccgatgc tggccactat    900
aaggccagcc agactgcgac acagtccatc ccctcgacca ctcttttggc gcttcattgt    960
cgacgtgtgg tgagctctca ctggggcgtc cctctaagat ctgtccactc ctggtttagg   1020
ggttaagcct ttngtgcccc tgaaagtttn ncacctgtag gtggggcaag ctanagagat   1080
ntt                                                                 1083
```

<210> SEQ ID NO 115
<211> LENGTH: 913
<212> TYPE: DNA
<213> ORGANISM: Rattus norvegicus
<220> FEATURE:
<221> NAME/KEY: misc_feature
<222> LOCATION: 1- 913
<223> OTHER INFORMATION: n = g, a, c or t(u)

<400> SEQUENCE: 115

```
ggggaaaaaa atntgggncc ctttnaaaga aattctggaa anccgccggt ggggnatttt     60
taanataggt ggggnccnaa aancttgatt ttcccttttc cctttgantg nntaaagttg    120
cnaanttccc tttggacgcc ntttacaaga ttagccngtg tgtaacctttt gggccctttta  180
acaggattnc ttggccntnt gaaacacgta tttatgtcag gnttntaccg tngcaaantt   240
ngttttgagc agcaacgaaa tcactttatg gttggaggtc accacaactt gaggatgtat    300
taatccgcag tattagagag tcgagaacca ntatcttaga ggatcggtag actgatgttt    360
ccntttngc ttggagttgn cttnccacta gaggcaacag catcagtatt gttccccagt    420
cccctcaca ttgattcgaa ctttaaggac actgatctct ggcttggtag agggttcagc     480
acacatacca gagttacgag tcacgtgcca gaaggcaaac tgaacacgga attagaggga    540
actcgatgtc tccggcttgc actggtcttn tcttgcacta gaatcnttca tcntgctccc    600
agtccgggac gtccaggcaa caaggcgtg gaaagtgagg gggctgggag gtgtgtttgc    660
cttgcctcag gcgctgggtg gggttgggc gtgccagcac tccctgggcg ggcctcaccg    720
atgctggcca ctataaggcc agccagactg cgacacagtc catcccctcg ccactctttt    780
ggcgcttcat tgtcgacgtg tggtgagctc tcactggggc gtccctctaa gatctgtcca    840
```

```
ctcctggtct agggnttaag cctttcctgc cctgaaagac cntacntgta ggttngncaa      900
gctaaatgag atc                                                         913
```

<210> SEQ ID NO 116
<211> LENGTH: 1123
<212> TYPE: DNA
<213> ORGANISM: Rattus norvegicus
<220> FEATURE:
<221> NAME/KEY: misc_feature
<222> LOCATION: 1- 1123
<223> OTHER INFORMATION: n = g, a, c or t(u)

<400> SEQUENCE: 116

```
acgcnatntt ggtggaattt gggggtaaa aattttnaac gaattaggna ncttagggna        60
cnaaatccga aatgggaat ngggntaaat ttcgaaccnt ttnggaggnn ntaaatntaa       120
aaatgaggnt aattggnttn gaaangcnta tcaggcattc caaattntta aatttccctt       180
ggccagagat tgggaaaat tttncccgga ntccagtttt aggttnnttg gaaaaacggn       240
gccccaggga ttgttgcacc nttcccaatn aaggnggttt tccntccaan gcctttnggg       300
gnaaacccag gggggnttn aggggcccaa ttcaggaaaa ggggaccgga ntcgggtccc       360
ggaaggnttc ccggnggga atcaacccgg ttcccntccg gaggccgggg gggacccttta       420 ggtttcccct tgcagggta anatcccctt tttcaacccg ggggtttgc ggggnacgcc         480 cctttgccct ttcccttccc ttgccnggcc cgttttgccc aattnggccg gtcctaactt       540
gttggcgcaa gggactttttg gcagcccgg ccggtttggc ggttggactc caaggggggta       600 acagggccaa accntttggt tgaaanaagt taacttgcgc ccccagtcan gcgtcagtgg       660
gnangtgacc ccgcntttag gagtttgccc cngccnttag gccttgcccc cagaggtcgc       720
cccacntact agagtgtcgc ttggcgcgat gacgtangan gacgcaggcg cagtgagtag       780
gcgacgttgg gacggccctt ggttgtgtcg ggggcggaac tntgntggct ttgagcgcct       840
tcnaaacagt aggttgcttg gggctctgcg gcgtcggaaa taaggcgggg aggagcaaga       900
aaacagggat cctccagtcg tgtggaccga cccgagtccc gcacccttttt taaggcctgt       960 gttgcggatc cgcgcggcca tcacgcattg catcacggtt ttactgtgtg ggaaacgtag     1020
ccgtccatac ctgggtgtag tcaggaccct ttatggtggc tgtcacgcag gcgatttgnc     1080
aattgaaaga ctttnncctg taggnanggg nagctaaaaa gat                     1123
```

<210> SEQ ID NO 117
<211> LENGTH: 1116
<212> TYPE: DNA
<213> ORGANISM: Rattus norvegicus
<220> FEATURE:
<221> NAME/KEY: misc_feature
<222> LOCATION: 1- 1116
<223> OTHER INFORMATION: n = g, a, c or t(u)

<400> SEQUENCE: 117

```
aattttttaa ccnccccccnt tttnaagntt gaanttgcan tgcctaggag ccctatttt       60 cccccttgna antttttcccc gtaaataagg naatgntgna nttgtattta ncttgcccaa    120
aaaaaacnnt gttcttnaat gcaaggtant tgggggttat tattntgaaa ggcaactaat     180
tnttaatggt ggattnaaca attttgaagn ggattaaana aaanaaatna ttgntttcca     240
ttggnggtgt gggnttaaaa cccttggtnn ccagggttcc antgggttca ggcccttga      300 gngggntccc cnttccccgg gaatnggntt gaaccggaaa ttgaacattt tgcacccttt    360
```

```
tccggnggcc cttaaggatt gcagcnccag ttgcggggaa gggtaattc cttgcccncc      420 gtggaagggg tttcagnttc cttcccaacc ccccccggc cggagtccg gngggcggt      480 ttntttcacc ttaagggcgg gcgtggantt aaattaagcg ccggggnggg ntcccaagcc   540
ntccggcccg gctttggttc cttntgggcg ccggggggcna acggcccng gggctttggg   600 cggttntccn nccggccaac cgggncccgt ggttgntggg ttaggccagt gcaccnggag   660
ttnccggggg caaccaaatg tccaggactt angctntgca aggagtttgg gataggactc   720
ntacaatggt ccctccctcc gtttgccccc gaggccettt gggagctggt tnatcccaga   780
actcagtgag tcactctcat gaagcacggt tggctgcttt ggaatgctgg gcaacccccag  840 aacacagtgc tgtactagta cacacacaca cacacacaca cacacacacg ttacacatgc   900
tgacacaaac atgaaaatgc agtcaacggc aggcagagat ggatggatgc acattgctgt   960
ggaatggtac actttgcacc tcacactctt ccagagggac agtccataca acactcagct  1020
tcgcttccca ctataggctt cacatgacca gctcttcagc gtcggaaagg acngtactga  1080
aagacttnac ctgtaggnng gncagctaaa aagatc                              1116
```

<210> SEQ ID NO 118
<211> LENGTH: 900
<212> TYPE: DNA
<213> ORGANISM: Rattus norvegicus
<220> FEATURE:
<221> NAME/KEY: misc_feature
<222> LOCATION: 1- 900
<223> OTHER INFORMATION: n = g, a, c or t(u)

<400> SEQUENCE: 118

```
gggngttngc tctcagatgc nagntacnnn tcaggggggng tctcacgaga aaanctnatg      60
tgtgggggnt antntgtatc ccctnnnctc nctcgaganc ccnnntctcg anattttggn   120 gaccngggg cggggcccag anactcncca ccccatatgg ngaccctnta taagtgtcnn    180
ccagggnntg ttttgggnaa aatatancnn anagnggtgt ntntnanatc tcggggggtg   240 acagaccccnn attttttttt ataaagaccc ggggcatntt ctcngccccn tctcctcngc   300
tacangnnac ccacacacag tgtgtctcct ctcagcccc tggcacactt tntntngant   360 cngngggggat atgagattcn cnagactggg nccgcnntan tanncncccc cntgtctcct  420
ctcatagtgt ngtgtccccc cctcacccnn tnttgnggtn ccctacaccc acacaatnta   480 gactctncc nccntcngct ntgngacnca canctgnaaa tcccgnnncn caaaaagggc    540
tgtnctcctc tctnttacng ggnggtcncc cncnnnngac tctnaaangt ccctcncaaa   600
agggacnctt ttctatacac ncttantttn cctcctttgt ntngcaaaaa annaccctgt   660 gttnccccc nctttatnat ntttnttttn ttcccccaaac taancttta ggnntnanct    720 tccgggccc caaccccaaa atcccantnt tcttttntnt tggttggggt gtcaaaattc    780 ctnccctaa anttttgaac ccccttaat tccccccccc ggntnaaggc ccnacttccc    840
tnggntnttt tcnctaaaaa attttttgtn gccctccctg ggaaatcccc ggtattcctc    900
```

<210> SEQ ID NO 119
<211> LENGTH: 498
<212> TYPE: DNA
<213> ORGANISM: Rattus norvegicus
<220> FEATURE:
<221> NAME/KEY: misc_feature
<222> LOCATION: 1- 498
<223> OTHER INFORMATION: n = g, a, c or t(u)

<400> SEQUENCE: 119

-continued

| | |
|---|---|
| atgttgtgtg gaattgtgag cggataacaa tttcacacag aattcagaag gatctcagaa | 60 |
| attgaaagca tgtgcaaaga taaagatttg gggtagtagt agtggtcaaa agggacaagg | 120 |
| taataatggt aatatgcttt tgtgtatgtg ttcttttaga gttatgttaa aatctagaga | 180 |
| agcaaagtcg attctcatag atgcttttag tctttggacc ctgactagag acagtttaca | 240 |
| ccctagacaa gagagagaat gggttgagt aaaacagtcc tcccgaactc tccacagatg | 300 |
| ctttggcaaa agaaggaaat gagcttaaac tttttggagc tctcctggga acagaaggag | 360 |
| gtgggagacg tcttgcctcc ttgctgctcc tattggagaa gtgcttattt ctggttctgg | 420 |
| gttttttagg taggntgtct gggtcccttt ggtntgaaag accttacctg taggtttggn | 480 |
| cgntngaaaa gatcntgg | 498 |

<210> SEQ ID NO 120
<211> LENGTH: 380
<212> TYPE: DNA
<213> ORGANISM: Rattus norvegicus
<220> FEATURE:
<221> NAME/KEY: misc_feature
<222> LOCATION: 1- 380
<223> OTHER INFORMATION: n = g, a, c or t(u)

<400> SEQUENCE: 120

| | |
|---|---|
| aatgggnggt ttccgaaaan aacgcnaaaa aaaagttag ggaatttggg gaattaagaa | 60 |
| nccgggaacn tgnaaacatt gaccaanctt gttttaatta ccggtttggg gnaaaagggg | 120 |
| caacccaaa ggggaaggga anggaangga aaatnaattn cctttnnaaa aaggagnaaa | 180 |
| tncgggtang gaaaattccg gtgnggggtt ttcaaaggtc cccccccgnn ggnntaaaaa | 240 |
| attgaagttn antcnnggggg gggaacccaa nagaatataa anaaaccggg gtttccccn | 300 |
| gggagttcct tgggggtttn ccggttcgac ccgncgntta ccggaaacct ntcnccttt | 360 |
| tcccttgggg naggggggg | 380 |

<210> SEQ ID NO 121
<211> LENGTH: 998
<212> TYPE: DNA
<213> ORGANISM: Rattus norvegicus
<220> FEATURE:
<221> NAME/KEY: misc_feature
<222> LOCATION: 1- 998
<223> OTHER INFORMATION: n = g, a, c or t(u)

<400> SEQUENCE: 121

| | |
|---|---|
| acatgtacac aactgggtcc cagccaagtc aggttccagc tgccagcaga ggcctggagc | 60 |
| tagcttcgcg tgcactacca ccctgcccaa cctggcactg tgcccattga cttcgggggg | 120 |
| ccggggggcag gaggtaccca cctccccacc ctcctcttcc ctcctctcag gagcttatct | 180 |
| atcggtgagc agcaagtagg aaaaggtaag ctgagaaaga gcacttggct ggctacagga | 240 |
| cctcagcctg aggtgtgaaa caggagactg ggcactgggg aaacagcagc actggctggg | 300 |
| ccaaaggga gggaggaagg caatgaatgg gcaagcctgt gccttacaga aacagactcc | 360 |
| cttgggctgg gtgctggaat cctaacccct cagtgatggg ggaactctgc tccagtgagc | 420 |
| tgaagtatac atgtgggaa ttgggggggtg gggtagggg aaggcaatcc aaaggtcact | 480 |
| cccctgacct agttggacca cagttaatta aggctcccaa gccctgctga ctcttnacgt | 540 |
| ctggtttctg gaaagaaggg agttaatcag caaacaattt aagaaaggta taactgtcta | 600 |
| ccctgcaga ggatcatggg ttnctctct anncttctga gccgtggatc tcagccaaaa | 660 |

-continued

| | |
|---|---|
| acaaaaacca aaacaaagaa acaaacgcct atttaaaagg gggttggagt tgggcagggg | 720 |
| tgaggtngtt agatcatctg agagctccag gacacgcana tagttaaaga ggaaaccaag | 780 |
| atccaaatgt cttctgacat cacacgggat gcagcagcac accaacatat actttancct | 840 |
| cnccagagag gaaaacaacc gcctagttaa taagcagagt tgggctgttg gcaaaccgtc | 900 |
| attccagatc tgaggnaagt tggatggttc gggtgtctat gttnacntaa gacctgtttt | 960 |
| acaagctnnt atgggcaagg gctttggttc nagnaagg | 998 |

<210> SEQ ID NO 122
<211> LENGTH: 970
<212> TYPE: DNA
<213> ORGANISM: Rattus norvegicus
<220> FEATURE:
<221> NAME/KEY: misc_feature
<222> LOCATION: 1- 970
<223> OTHER INFORMATION: n = g, a, c or t(u)

<400> SEQUENCE: 122

| | |
|---|---|
| ccggtcnccg aaggannttg aaccttcccg gttttttaann aanacccgna tnttcgggat | 60 |
| tgggtttttta acggcttttt ttanaaggcc nagataccct tttnatggcc tttattccct | 120 |
| tccgttttnt tccccccctt caatttggaa gtttggtttg ccgaanttta agttnttgtc | 180 |
| ntcctncgtt ntttttttcc nttnttttt cccaaaagta acaanccggt attggtttcc | 240 |
| aaggntnttn ttgaacccgt aatngcggnt ttccggttaa ccnagggttt gttcctnngc | 300 |
| cgnttcctcc aatttttgga ntttcccagn tngggggtccn ttntcttgtt nacngttcca | 360 |
| aacntaattg acanttaatt tttcctgtgt aanttgtccc cgganattnt gggntcttgg | 420 |
| ngcagggcct ttttcattg gaagcaaccc cntaaatttt taccaggctt gattgtttag | 480 |
| gaagtaatcc ttgcttngaa nccccacttn ttntttccaa ggntggaaac caggattttg | 540 |
| gaactgcaga ggcttcaggg tctgggaagc ggagcangca aagantggag tgcactgtcc | 600 |
| ttttgcaata tggggtttgc ttgcttgctg gctcntntcn tgctntntca gatggtgact | 660 |
| gaggctactt cagcaggact aggaataatc atgtccaggt ggntgcccct ccgagcagaa | 720 |
| agggacagac gtgggcgat gaagttgcta tcgttttttt ttttttctgc acagactgca | 780 |
| aagtgtgcag agggagggag gctgtgcaaa aaaaaaaaaa aaaaaaaaaa aaaaaaaaac | 840 |
| cgaggacgca gaagttagac tgctgaccca tttggtgcat gtgtgcccat ggagggaggg | 900 |
| gaccttctca aaagggttca cgcagcaagc attgaaagnt tccacntgta gngtcgcaag | 960 |
| caactgagat | 970 |

<210> SEQ ID NO 123
<211> LENGTH: 884
<212> TYPE: DNA
<213> ORGANISM: Rattus norvegicus
<220> FEATURE:
<221> NAME/KEY: misc_feature
<222> LOCATION: 1- 884
<223> OTHER INFORMATION: n = g, a, c or t(u)

<400> SEQUENCE: 123

| | |
|---|---|
| ngggccccccc tcgaggtcga cggtatcgat aagcttgagg gacccacgtg atggaaaggg | 60 |
| agaagcaatt tagtgtcctn tgtcctctga cctccacaag tgctgtggca tgggacaca | 120 |
| ggactgtaca cacacacaca cacacacaca cacacacaca cacacacgca cgcacacaca | 180 |
| cccctcaagt aaccgtggaa taaggtccg accagaaacc acgctggaac gggagatgct | 240 |
| ggagcacatc agggtggtgc taagcagcag atcggcctgt aactggcagc agagggtgt | 300 |

-continued

| | |
|---|---|
| ggctctttca gaaccaggag ggcatcgccc ctccagccag actctccagc tttcttcccc | 360 |
| tccttgcctc ctgttttcct tctgcctacc ttcctttggc ctcaaaccat aatgtgcaac | 420 |
| acattcaaac tgtagtaagt gttttaattt tctactaaac aataaaacct ttagattttc | 480 |
| actgggccag tgctggtaac agcagactgg gtggagtatc acagagggtg tggagcaagc | 540 |
| tggctaccca gggctgggca cactcaacac tctggcattc ngtggaagtt ctgggcagta | 600 |
| aaaacagaag canacgtcac gcacaggttc catagtgtna ggcatcttaa tctancnaga | 660 |
| anacctggtg ttnagtntgt nnacaaaann gantgntgna cttggacagn ggtgttttnn | 720 |
| tcccagggct tccaggantt aggggtatac caggcccann acattgggna aacgtgtgtg | 780 |
| tnaannnttt cntntnaaac cnccnnggtt gacnactngn nntccntttn aanggnccca | 840 |
| gttccccttg gggggttngn tntggaaaaa ggctttccgg tttc | 884 |

<210> SEQ ID NO 124
<211> LENGTH: 855
<212> TYPE: DNA
<213> ORGANISM: Rattus norvegicus
<220> FEATURE:
<221> NAME/KEY: misc_feature
<222> LOCATION: 1- 855
<223> OTHER INFORMATION: n = g, a, c or t(u)

<400> SEQUENCE: 124

| | |
|---|---|
| cccctccgg ggggtttana anggaatnaa tgggtntntn ccaggggggg aaacccttna | 60 |
| ccgcgngcct ttcggaattt tngtccaccg naaaaaattt nccatgngca ccatgnaagn | 120 |
| tnacgagggn attngggtt anagttttgg agtgggccaa nangaacatg gaggaatatt | 180 |
| tgttttggtt tgngaaccat accttggaaa gattgtattt ttatccgcca acaaccacng | 240 |
| tggtagggtg ttttttttgtt tgcagcagca gataagggca gaaaaaagat ntcagagatc | 300 |
| cttgatntt tnttcggggt ngacgttcat gttgngngga ttgggagcgg anaacaattt | 360 |
| cacacagcaa ggagaggagc caatatagag gggaaaaaaa agaaggggga aagcagttag | 420 |
| tttaaaaagt tgagagaaca aagtatgttt tgnttggatg ggcaaccaaa gaagcntgcc | 480 |
| aggaatggtc ggtaaaaggt gtaagagtca tgaaagtntt ctgtccaacc gttaccggaa | 540 |
| acatgcaagg aatttcttag actggccagg attggattgt gggaaaggtn tnttcaagcn | 600 |
| tccccttggc ttttatggca agaaaatagt gcggactata gagagcgtcg ttctcaaagc | 660 |
| tttccccaat agcagaaaag cattgtccta aattccctaa aaggcaccgt gaaataaata | 720 |
| ttacgggaca cgatggcaca agaaggagct ttcaactctg ccaccagaac agttatactt | 780 |
| catagtaacc atgttgccct gttcaatgac aaggcacgct ctccagcaga aagggaaaag | 840 |
| gagctgagtt cgcac | 855 |

<210> SEQ ID NO 125
<211> LENGTH: 1059
<212> TYPE: DNA
<213> ORGANISM: Rattus norvegicus
<220> FEATURE:
<221> NAME/KEY: misc_feature
<222> LOCATION: 1- 1059
<223> OTHER INFORMATION: n = g, a, c or t(u)

<400> SEQUENCE: 125

| | |
|---|---|
| caatttttaa aaaaagaat ttgggtttaa tccaaaantt gnnncaaaaa ttggttgacc | 60 |
| nttttaaccc caaaaccatg nnttgncctt tcccctnacc ngtnatagtg nttgnantgt | 120 |

```
aacccaacaa tcaacggnta tttgttcagg ganttnttgg taccaggcnn ttggttttga    180
naaancggta ggtccgggaa gcnttgacgg taagcccngg gganaagggc caacggngat    240
cccaaattag gagcttgacg cattgttttc ntttgcntgg aatgncattc ttctcttctc    300
cntttatcta gaaaacgntt actcatgctt caaanccacn gttgacttcc ccagcattgn    360
ttcncntagc tccttctttg aaacaactga ttgggaaatc aggaggatan gaaaagcttt    420
aacaagagct ttcaggggct ttcggagaga actcattctt gtaggacgca ggccatgcaa    480
gcatcaggct ctgccttctg gaccccagta tacagacata tgcacaactg cagtggttca    540
tacttgtaat cccagtgtta ggaagactta gacttggagc ttgctggtca gactggtaag    600
cccagttcag tgagaccctg acttaaaaat gaagttggaa agaaatttgg aaagataatc    660
tggtattcat ctctgggctc tatttgcaca ggcacacaca caaatatacc aatataacat    720
acacagaaag agaaggggag ggaggaagag agggagggcg gtagagaact tgtgaatgtc    780
ttttgatagg ttttttttta agttattgga ttaaaccatc agcagtgtca cattggttaa    840
gttaaaaata ataaaatgaa gcaacttatc tttgctgaaa ttcattactc attatgagag    900
tttgataaaa aaaagagga gtctcccaca gttttcctgt ctcatctttt actccagggg    960
acggtcacac tattcagtaa gatacctagg ctatctggct cactggactn ggcgtgaaag   1020
actnnacctg taggtttgng cgctgaaaag atcttnaac                          1059
```

<210> SEQ ID NO 126
<211> LENGTH: 1042
<212> TYPE: DNA
<213> ORGANISM: Rattus norvegicus
<220> FEATURE:
<221> NAME/KEY: misc_feature
<222> LOCATION: 1- 1042
<223> OTHER INFORMATION: n = g, a, c or t(u)

<400> SEQUENCE: 126

```
aaacncnttc tgaanccca atcctnaga atnttttnaa atcccccng gggngnagcc      60 aaatttaacn nttttttcca agagcatgaa cagngngatt cttgggganag ctttngggtt   120 cccttttttnt naatcnncat ngagggttct aantgaacct naaggnnatt taactttttna  180 tggaacaaac ccgttggtgt gtcccctcct tggagantttg agttggaact taaaaaaaac   240 cttttccnaaa aattgtgtaa tctgantcca aacccaaatg aggacaaatc cagtgtagga   300
ggnatttagg caaattaaac tgacttggtc aactttctga aaatgatgtc ttgatttcag    360
gaaggatccc cagtgcntcg gggacntgaa agggagatgt aaccccttgag ctcatggnta   420 ggaagggaaa tcttagagac agcttggtaa aatctgagtg aggttgagag gttggaggac    480
cacattgtgt atntgctcat ccctgtgagg gagagacttg tactctgctc ttgagaaggc   540
agaactgtta ggcagacact tagagaatat atgtcatggc aaangacatc cacccaacaa   600
gtcttcagta acaaagcact aaacagaaag gggttgaaga gacttggtca gtggcatgag   660
agnttttatt gctcttacag aggactcggc atgcntagca gctcacaaca gcctgtgact    720
tcaacactat gcctcttggc ctcaggagac acctgtgtac tcccacccng acacatatac    780
ttaaaaataa aagaaatctt ttaaacattg agcaaatgta atcaggtact aacattgaat    840
atatctgggg ccaggaatta ttctggttta ttgccttttt cggaagccta atatcacaca    900
tagagaaata ggcagcacag gcctaacagc ccatantgtg tgctattcta tcaatagtgc    960
caagtattga catggactat tnttaaggcc aaangagagg tcnccagaaa gttatacatg   1020
taggttggcg cgctgaaagg at                                            1042
```

<210> SEQ ID NO 127
<211> LENGTH: 960
<212> TYPE: DNA
<213> ORGANISM: Rattus norvegicus
<220> FEATURE:
<221> NAME/KEY: misc_feature
<222> LOCATION: 1- 960
<223> OTHER INFORMATION: n = g, a, c or t(u)

<400> SEQUENCE: 127

| | | | | | | |
|---|---|---|---|---|---|---|
| ggcccnnaat | naaanggnng | gttgaacccc | ntnttngaca | ngntgcccaa | aantacnggn | 60 |
| aaccattncc | naaatttnna | agtgtgggat | naaggcntgn | cccatnatcc | tccctnttga | 120 |
| ntgcncccaa | agtaaagncc | aanttgaggg | nggannttn | ttgaaacgta | attaanattt | 180 |
| ttccgataag | gaaacggagg | cccgggaant | gatccntttg | gagttaccag | gtcagtttag | 240 |
| cattaggntg | acagttgnga | ccaattnatc | cttgcccgtt | ggttggaagg | agaggggant | 300 |
| aagggttaag | ctcntgagtc | ccttgaaggc | cttggaatcg | ggaattccct | taaagccaac | 360 |
| cccctttgccg | ttgaactgca | ccaaccagat | gtctnccagt | ttgcttgaag | agacgggatt | 420 |
| cantgntgtg | gagaggggca | ggagggntgg | gaggtgacnt | nacagggttc | agggattctt | 480 |
| ttagaagggt | ccaggctcat | ggcttccccc | ccccccagcc | aggtcagaca | ctaaagtgtc | 540 |
| ttaagcccct | ccatacctgc | cgctccccca | ccttggatga | agccggccat | taggcaggga | 600 |
| ccgtctctgg | gagaggccaa | gccctctggc | tcacttgtgg | atttccttta | agcaagactt | 660 |
| cctctctgct | tccaggactc | ctgtcaaaca | agagggtccc | tggcttagag | tttgggagct | 720 |
| gcaggcagaa | cagacattcc | ccgatgactc | acaagcctgg | aactctgtgg | gccagcagga | 780 |
| atggggatgg | ctttctggtc | agtcagggtc | aactgggaca | ctcactctga | gacagggagg | 840 |
| caagggagaa | acaggtcaga | ggtagagaga | gctcagtcca | gggactcacg | gtgaggtccc | 900 |
| taaggtgcgt | agggagagga | tntaacattc | ggtttggnna | gctagaaaag | atctntaaaa | 960 |

MAMMALIAN GENES INVOLVED IN VIRAL INFECTION AND TUMOR SUPPRESSION

This application is a U.S. national stage application of PCT International Application No. PCT/US98/21276 and claims priority to provisional application No. 60/062,021, filed Oct. 10, 1997, now abandoned.

ACKNOWLEDGMENTS

This invention was made with government support under the National Institutes of Health (CA68283). The U.S. Government may have certain rights in this invention.

BACKGROUND

1. Field of the Invention

The present invention provides methods of identifying cellular genes used for viral growth or for tumor progression. Thus, the present invention relates to nucleic acids related to and methods of reducing or preventing viral infection and for suppressing tumor progression. The invention also relates to methods for screening for additional such genes.

2. Background Art

Various projects have been directed toward isolating and sequencing the genome of various animals, notably the human. However, most methodologies provide nucleotide sequences for which no function is linked or even suggested, thus limiting the immediate usefulness of such data.

The present invention, in contrast, provides methods of screening only for nucleic acids that are involved in a specific process, i.e., viral infection or tumor progression. For viral infection, the nucleic acids isolated are useful in treatments for these processes because by this method only nucleic acids which are also nonessential to the cell are isolated. Such methods are highly useful, since they ascribe a function to each isolated gene, and thus the isolated nucleic acids can immediately be utilized in various specific methods and procedures.

For, example, the present invention provides methods of isolating nucleic acids encoding gene products used for viral infection, but nonessential to the cell. Viral infections are significant causes of human morbidity and mortality. Understanding the molecular mechanisms of such infections will lead to new approaches in their treatment and control.

Viruses can establish a variety of types of infection. These infections can be generally classified as lytic or persistent, though some lytic infections are considered persistent. Generally, persistent infections fall into two categories: (1) chronic (productive) infection, i.e., infection wherein infectious virus is present and can be recovered by traditional biological methods and (2) latent infection, i.e., infection wherein viral genome is present in the cell but infectious virus is generally not produced except during intermittent episodes of reactivation. Persistence generally involves stages of both productive and latent infection.

Lytic infections can also persist under conditions where only a small fraction of the total cells are infected (smoldering (cycling) infection). The few infected cells release virus and are killed, but the progeny virus again only infect a small number of the total cells. Examples of such smoldering infections include the persistence of lactic dehydrogenase virus in mice (Mahy, B. W. J., *Br. Med. Bull.* 41: 50–55 (1985)) and adenovirus infection in humans (Porter, D. D. pp. 784–790 in Baron, S., ed. *Medical Microbiology* 2d ed. (Addison-Wesley, Menlo Park, Calif. 1985)).

Furthermore, a virus may be lytic for some cell types but not for others. For example, evidence suggests that human immunodeficiency virus (HIV) is more lytic for T cells than for monocytes/macrophages, and therefore can result in a productive infection of T cells that can result in cell death, whereas HIV-infected mononuclear phagocytes may produce virus for considerable periods of time without cell lysis. (Klatzmann, et al. *Science* 225:59–62 (1984); Koyanagi, et al. *Science* 241:1673–1675 (1988); Sattentau, et al. *Cell* 52:631–633 (1988)).

Traditional treatments for viral infection include pharmaceuticals aimed at specific virus derived proteins, such as HIV protease or reverse transcriptase, or recombinant (cloned) immune modulators (host derived), such as the interferons. However, the current methods have several limitations and drawbacks which include high rates of viral mutations which render anti-viral pharmaceuticals ineffective. For immune modulators, limited effectiveness, limiting side effects, a lack of specificity all limit the general applicability of these agents. Also the rate of success with current antivirals and immune-modulators has been disappointing.

One aspect of the current invention focuses on isolating genes that are not essential for cellular survival when disrupted in one or both alleles, but which are required for virus replication. This may occur with a dose effect, in which one allele knock-out may confer the phenotype of virus resistance for the cell. As targets for therapeutic intervention, inhibition of these cellular gene products, including: proteins, parts of proteins (modification enzymes that include, but are not restricted to glycosylation, lipid modifiers [myriolate, etc.]), lipids, transcription elements and RNA regulatory molecules, may be less likely to have profound toxic side effects and virus mutation is less likely to overcome the 'block' to replicate successfully.

The present invention provides a significant improvement over previous methods of attempted therapeutic intervention against viral infection by addressing the cellular genes required by the virus for growth. Therefore, the present invention also provides an innovative therapeutic approach to intervention in viral infection by providing methods to treat viruses by inhibiting the cellular genes necessary for viral infection. Because these genes, by virtue of the means by which they are originally detected, are nonessential to the cell's survival at a level of expression necessary to inhibit virus replication, these treatment methods can be used in a subject without serious detrimental effects to the subject, as has been found with previous methods. The present invention also provides the surprising discovery that virally infected cells are dependent upon a factor in serum to survive. Therefore, the present invention also provides a method for treating viral infection by inhibiting this serum survival factor. Finally, these discoveries also provide a novel method for removing virally infected cells from a cell culture by removing, inhibiting or disrupting this serum survival factor in the culture so that non-infected cells selectively survive.

The selection of tumor suppressor gene(s) has become an important area in the discovery of new target for therapeutic intervention of cancer. Since the discovery that cells are restricted from promiscuous entry into the cell cycle by specific genes that are capable of suppressing a 'transformed' phenotype, considerable time has been invested in the discovery of such genes. Some of these genes include the gene associated by rhabdomyosarcoma (Rb) and the p53 (apoptosis related) encoding gene. The present invention provides a method, using gene-trapping, to select cell lines that have a transformed phenotype from cells that are not transformed and to isolate from these cells a gene that can suppress a malignant, or transformed, phenotype. Thus, by the nature of the isolation process, a function is associated with the isolated genes. The capacity to select quickly tumor suppressor genes can provide unique targets in the process of treating or preventing, and even for diagnostic testing of, cancer.

DETAILED DESCRIPTION OF THE INVENTION

The present invention utilizes a "gene trap" method along with a selection process to identify and isolate nucleic acids from genes associated with a particular function. Specifically, it provides a means of isolating cellular genes necessary for viral infection but not essential for the cell's survival, and it provides a means of isolating cellular genes that suppress tumor progression.

The present invention also provides a core discovery that virally infected cells become dependent upon at least one factor present in serum for survival, whereas non-infected cells do not exhibit this dependence. This core discovery has been utilized in the present invention in several ways. First, inhibition of the "serum survival factor" can be utilized to eradicate persistently virally infected cells from populations of non-infected cells. Inhibition of this factor can also be used to treat virus infection in a subject, as further described herein. Additionally, inhibition of or withdrawal of the serum survival factor in tissue culture allows for the detection of cellular genes required for viral replication yet nonessential for an uninfected cell to survive. The present invention further provides several such cellular genes, as well as methods of treating viral infections by inhibiting the functioning of such genes.

The invention also provides cellular genes whose overexpression is associated with inhibition of viral growth and/or reproduction.

The present method provides several cellular genes that are necessary for viral growth in the cell but are not essential for the cell to survive. These genes are important for lytic and persistent infection by viruses. These genes were isolated by generating gene trap libraries by infecting cells with a retrovirus gene trap vector, selecting for cells in which a gene trap event occurred (i.e., in which the vector had inserted such that the promoterless marker gene was inserted such that a cellular promoter promotes transcription of the marker gene, i.e., inserted into a functioning gene), starving the cells of serum, infecting the selected cells with the virus of choice while continuing serum starvation, and adding back serum to allow visible colonies to develop, which colonies were cloned by limiting dilution. Genes into which the retrovirus gene trap vector inserted were then isolated from the colonies using probes specific for the retrovirus gene trap vector. Thus nucleic acids isolated by this method are isolated portions of genes. Additionally, utilizing this method, several cellular genes were isolated whose overexpression prevents viral infection or tumor growth, and they provide methods of treating viral infection or tumor growth/ suppression by overexpression of these genes.

Thus the present invention provides a method of identifying a cellular gene necessary for viral growth in a cell and nonessential for cellular survival, comprising (a) transferring into a cell culture, e.g. growing in serum-containing medium, a vector encoding a selective marker gene lacking a functional promoter, (b) selecting cells expressing the marker gene, (c) removing serum from the culture medium, (d) infecting the cell culture with the virus, and (e) isolating from the surviving cells a cellular gene within which the marker gene is inserted, thereby identifying a gene necessary for viral growth in a cell and nonessential for cellular survival. The present invention also provides a method of identifying a cellular gene used for viral growth in a cell and nonessential for cellular survival, comprising (a) transferring into a cell culture growing in serum-containing medium a vector encoding a selective marker gene lacking a functional promoter, (b) selecting cells expressing the marker gene, (c) removing serum from the culture medium, (d) infecting the cell culture with the virus, and (e) isolating from the surviving cells a cellular gene within which the marker gene is inserted, thereby identifying a gene necessary for viral growth in a cell and nonessential for cellular survival or a gene whose overexpression prevents viral reproduction but is not fatal to the survival to the cell. In any selected cell type, such as Chinese hamster ovary cells, one can readily determine if serum starvation is required for selection. If it is not, serum starvation may be eliminated from the steps.

Alternatively, instead of removing serum from the culture medium, a serum factor required by the virus for growth can be inhibited, such as by the administration of an antibody that specifically binds that factor. Furthermore, if it is believed that there are no persistently infected cells in the culture, the serum starvation step can be eliminated and the cells grown in usual medium for the cell type. If serum starvation is used, it can be continued for a time after the culture is infected with the virus. Serum can then be added back to the culture. If some other method is used to inactivate the factor, it can be discontinued, inactivated or removed (such as removing the anti-factor antibody, e.g., with a bound antibody directed against that antibody) prior to adding fresh serum back to the culture. Cells that survive are mutants having an inactivating insertion in a gene necessary for growth of the virus. The genes having the insertions can then be isolated by isolating sequences having the marker gene sequences. This mutational process disturbs a wild type function. A mutant gene may produce at a lower level a normal product, it may produce a normal product not normally found in these cells, it may cause the overproduction of a normal product, it may produce an altered product that has some functions but not others, or it may completely disrupt a gene function. Additionally, the mutation may disrupt an RNA that has a function but is never translated into a protein. For example, the alpha-tropomyosin gene has a 3' RNA that is very important in cell regulation but never is translated into protein. (*Cell* 75 pg 1107–1117, Dec. 17, 1993).

As used herein, a cellular gene "nonessential for cellular survival" means a gene for which disruption of one or both alleles results in a cell viable for at least a period of time which allows viral replication to be inhibited for preventative or therapeutic uses or use in research. A gene "necessary for viral growth" means the gene product, either protein or RNA, secreted or not, is necessary or beneficial, either directly or indirectly in some way for the virus to grow, and therefore, in the absence of that gene product (i.e., a functionally available gene product), the virus does not spread. For example, such genes can encode cell cycle regulatory proteins, proteins affecting the vacuolar hydrogen pump, or proteins involved in protein folding and protein modification, including but not limited to: phosphorylation, methylation, glycosylation, myristylation or other lipid moiety, or protein processing via enzymatic processing. Some examples of such genes include vacuolar H+ATPase, alpha tropomyosin, gas5 gene, ras complex, N-acetylglucosaminy-1-transferase I mRNA, annexin II, c-golgi CM130 and calcyclin.

Any virus capable of infecting the cell can be used for this method. Virus can be selected based upon the particular infection desired to study. However, it is contemplated by the present invention that many viruses will be dependent upon the same cellular genes for survival; thus a cellular gene isolated using one virus can be used as a target for therapy for other viruses as well. Any cellular gene can be tested for relevancy to any desired virus using the methods set forth herein, i.e., in general, by inhibiting the gene or its gene product in a cell and determining if the desired virus can grow in that cell. Some examples of viruses include HIV (including HIV-1 and HIV-2); parvovirus; papillomaviruses; hantaviruses; influenza viruses (e.g., influenza A, B and C viruses); hepatitis viruses A to G; caliciviruses; astroviruses; rotaviruses; coronaviruses, such as human respiratory coronavirus; picornaviruses, such as human rhinovirus and enterovirus; ebola virus; human herpesvirus (e.g., HSV-1–9); human adenovirus; for animal, the animal counterpart to any above listed human virus, animal retroviruses, such as simian immunodeficiency virus, avian immunodeficiency virus, bovine immunodeficiency virus, feline immunodeficiency virus, equine infectious anemia virus, caprine arthritis encephalitis virus, arenaviruses, arvoviruses, tickborne viruses or visna virus.

The nucleic acids comprising cellular genes of this invention were isolated by the above method and as set forth in the examples. The invention includes a nucleic acid comprising the nucleotide sequence set forth in SEQ ID NO:1, SEQ ID NO:2, SEQ ID NO:3, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:15, SEQ ID NO:16, SEQ ID NO:17, SEQ ID NO:18, SEQ ID NO:21, SEQ ID NO:23, SEQ ID NO:25, SEQ ID NO:26, SEQ ID NO:27, SEQ ID NO:29, SEQ ID NO:30, SEQ ID NO:31, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:48, SEQ ID NO:49, SEQ ID NO:50, SEQ ID NO:51, SEQ ID NO:52, SEQ ID NO:56, SEQ ID NO:57, SEQ ID NO:58, SEQ ID NO:59, SEQ ID NO:61, SEQ ID NO:62, SEQ ID NO:63, SEQ ID NO:66, SEQ ID NO:67, SEQ ID NO:68, SEQ ID NO:70, SEQ ID NO:71, SEQ ID NO:73, SEQ ID NO:74, SEQ ID NO:76, SEQ ID NO:77, SEQ ID NO:78, SEQ ID NO:79, SEQ ID NO:80, SEQ ID NO:81, SEQ ID NO:83, SEQ ID NO:84, SEQ ID NO:85, SEQ ID NO:86, SEQ ID NO:87, SEQ ID NO:88, SEQ ID NO:89, SEQ ID NO:91, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:112, SEQ ID NO:120, SEQ ID NO:121, SEQ ID NO:122, SEQ ID NO:123, SEQ ID NO:124, SEQ ID NO:125, SEQ ID NO:126, and SEQ ID NO:127 (this list is sometimes referred to herein as "SEQ LIST 1" for brevity). Thus these nucleic acids can contain, in addition to the nucleotides set forth in each SEQ ID NO in the sequence listing, additional nucleotides at either end of the molecule. Such additional nucleotides can be added by any standard method, as known in the art, such as recombinant methods and synthesis methods. Examples of such nucleic acids comprising the nucleotide sequence set forth in any entry of the sequence listing contemplated by this invention include, but are not limited to, for example, the nucleic acid placed into a vector; a nucleic acid having one or more regulatory region (e.g., promoter, enhancer, polyadenylation site) linked to it, particularly in functional manner, i.e. such that an mRNA or a protein can be produced; a nucleic acid including additional nucleic acids of the gene, such as a larger or even full length genomic fragment of the gene, a partial or full length cDNA, a partial or full length RNA. Making and/or isolating such larger nucleic acids is further described below and is well known and standard in the art.

Also provided in this invention are the double-stranded nucleic acids corresponding to the nucleic acid sequences set forth in SEQ ID 1 through SEQ ID 136, inclusive. It is recognized that "nucleic acid" as used herein, can refer to either or both strands of such double-stranded nucleic acids, such strands often referred to as the "positive" and "negative" strands. Either strand of such double-stranded nucleic acids may encode the polypeptides of this invention, and the coding sequences for such polypeptides may be translated in either direction along the strand. Examples of polypeptides encoded by either strand are disclosed herein.

The invention also provides a nucleic acid encoding the protein encoded by the gene comprising the nucleotide sequence set forth in any of the sequences listed in SEQ LIST 1, as well as allelic variants and homologs of each such gene. The gene is readily obtained using standard methods, as described below and as is known and standard in the art. The present invention also contemplates any unique fragment of these genes or of the nucleic acids set forth in any of the sequences listed in SEQ LIST 1. Examples of inventive fragments of the inventive genes can include the nucleic acids whose sequence is set forth in any of the sequences listed in SEQ LIST 1. To be unique, the fragment must be of sufficient size to distinguish it from other known sequences, most readily determined by comparing any nucleic acid fragment to the nucleotide sequences of nucleic acids in computer databases, such as GenBank. Such comparative searches are standard in the art. Typically, a unique fragment useful as a primer or probe will be at least about 20 to about 25 nucleotides in length, depending upon the specific nucleotide content of the sequence. Additionally, fragments can be, for example, at least about 30, 40, 50, 75, 100, 200 or 500 nucleotides in length. The nucleic acids can be single or double stranded, depending upon the purpose for which it is intended.

The present invention further provides a nucleic acid comprising the regulatory region of a gene comprising any one of the nucleotide sequences set forth in SEQ LIST 1, as well as homologs of each such gene. Additionally provided is a construct comprising such a regulatory region functionally linked to a reporter gene. Such reporter gene constructs can be used to screen for compounds and compositions that affect expression of the gene comprising the nucleic acids whose sequence is set forth in SEQ LIST 1, or any homologs thereof.

The nucleic acids set forth in the sequence listing are gene fragments; the entire coding sequence and the entire gene that comprises each fragment are both contemplated herein and are readily obtained by standard methods, given the nucleotide sequences presented in the sequence listing (see. e.g., Sambrook et al., *Molecular Cloning: A Laboratory Manual,* 2nd Ed., Cold Spring Harbor Laboratory, Cold Spring Harbor, N.Y., 1989; *DNA cloning: A Practical Approach,* Volumes I and II, Glover, D. M. ed., IRL Press Limited, Oxford, 1985). To obtain the entire genomic gene, briefly, a nucleic acid whose sequence is set forth in any of SEQ ID NO:1 through SEQ ID NO:127, or preferably in any of the sequences listed in SEQ LIST 1, or a smaller fragment thereof, is utilized as a probe to screen a genomic library under high stringency conditions, and isolated clones are sequenced. Once the sequence of the new clone is determined, a probe can be devised from a portion of the new clone not present in the previous fragment and hybridized to the library to isolate more clones containing fragments of the gene. In this manner, by repeating this process in organized fashion, one can "walk" along the chromosome and eventually obtain nucleotide sequence for the entire gene. Similarly, one can use portions of the present fragments, or additional fragments obtained from the genomic library, that contain open reading frames to screen a cDNA library to obtain a cDNA having the entire coding sequence of the gene. Repeated screens can be utilized as described above to obtain the complete sequence from several clones if necessary. The isolates can then be sequenced to determine the nucleotide sequence by standard means such as dideoxynucleotide sequencing methods (see, e.g., Sambrook et al., *Molecular Cloning: A Laboratory Manual*, 2nd Ed., Cold Spring Harbor Laboratory, Cold Spring Harbor, N.Y., 1989).

The present genes were isolated from rat; however, homologs in any desired species, preferably mammalian, such as human, can readily be obtained by screening a human library, genomic or cDNA, with a probe comprising sequences of the nucleic acids set forth in the sequence listing herein, or fragments thereof, and isolating genes specifically hybridizing with the probe under preferably relatively high stringency hybridization conditions. For example, high salt conditions (e.g., in 6×SSC or 6×SSPE) and/or high temperatures of hybridization can be used. For example, the stringency of hybridization is typically about 5° C. to 20° C. below the $T_m$ (the melting temperature at which half of the molecules dissociate from its partner) for the given chain length. As is known in the art, the nucleotide composition of the hybridizing region factors in determining the melting temperature of the hybrid. For 20 mer probes, for example, the recommended hybridization temperature is typically about 55–58° C. Additionally, the rat sequence can be utilized to devise a probe for a homolog in any specific animal by determining the amino acid sequence for a portion of the rat protein, and selecting a probe with optimized codon usage to encode the amino acid sequence of the homolog in that particular animal. Any isolated gene can be confirmed as the targeted gene by sequencing the gene to determine it contains the nucleotide sequence listed herein as comprising the gene. Any homolog can be confirmed as a homolog by its functionality.

Additionally contemplated by the present invention are nucleic acids, from any desired species, preferably mammalian and more preferably human, having 98%, 95%, 90%, 85%, 80%, 70%, 60%, or 50% homology, or greater, in the region of homology, to a region in an exon of a nucleic acid encoding the protein encoded by the gene comprising the nucleotide sequence set forth in any of the sequences listed in SEQ LIST 1 or to homologs thereof. Also contemplated by the present invention are nucleic acids, from any desired species, preferably mammalian and more preferably human, having 98%, 95%, 90%, 85%, 80%, 70%, 60%, or 50% homology, or greater, in the region of homology, to a region in an exon of a nucleic acid comprising the nucleotide sequence set forth in any of the sequences listed in SEQ LIST 1 or to homologs thereof. These genes can be synthesized or obtained by the same methods used to isolate homologs, with stringency of hybridization and washing, if desired, reduced accordingly as homology desired is decreased, and further, depending upon the G-C or A-T richness of any area wherein variability is searched for. Allelic variants of any of the present genes or of their homologs can readily be isolated and sequenced by screening additional libraries following the protocol above. Methods of making synthetic genes are described in U.S. Pat. No. 5,503,995 and the references cited therein.

The nucleic acid encoding any selected protein of the present invention can be any nucleic acid that functionally encodes that protein. For example, to functionally encode, i.e., allow the nucleic acid to be expressed, the nucleic acid can include, for example, exogenous or endogenous expression control sequences, such as an origin of replication, a promoter, an enhancer, and necessary information processing sites, such as ribosome binding sites, RNA splice sites, polyadenylation sites, and transcriptional terminator sequences. Preferred expression control sequences can be promoters derived from metallothionine genes, actin genes, immunoglobulin genes, CMV, SV40, adenovirus, bovine papilloma virus, etc. Expression control sequences can be selected for functionality in the cells in which the nucleic acid will be placed. A nucleic acid encoding a selected protein can readily be determined based upon the amino acid sequence of the selected protein, and, clearly, many nucleic acids will encode any selected protein.

The present invention additionally provides a nucleic acid that selectively hybridizes under stringent conditions with a nucleic acid set forth in SEQ LIST 1 or with a nucleic acid encoding the protein encoded by the gene comprising the nucleotide sequence set forth in any sequence listed in SEQ LIST 1. This hybridization can be specific. The degree of complementarity between the hybridizing nucleic acid and the sequence to which it hybridizes should be at least enough to exclude hybridization with a nucleic acid encoding an unrelated protein. Thus, a nucleic acid that selectively hybridizes with a nucleic acid of the present protein coding sequence will not selectively hybridize under stringent conditions with a nucleic acid for a different, unrelated protein, and vice versa. Typically, the stringency of hybridization to achieve selective hybridization involves hybridization in high ionic strength solution (6×SSC or 6×SSPE) at a temperature that is about 12–25° C. below the $T_m$ (the melting temperature at which half of the molecules dissociate from its partner) followed by washing at a combination of temperature and salt concentration chosen so that the washing temperature is about 5° C. to 20° C. below the $T_m$ of the hybrid molecule. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The washing temperatures can be used as described above to achieve selective stringency, as is known in the art. (Sambrook et al., *Molecular Cloning: A Laboratory Manual*, 2nd Ed., Cold Spring Harbor Laboratory, Cold Spring Harbor, N.Y., 1989; Kunkel et al. *Methods Enzymol.* 1987:154:367, 1987). Nucleic acid fragments that selectively hybridize to any given nucleic acid can be used, e.g., as primers and or probes for further hybridization or for amplification methods (e.g., polymerase chain reaction (PCR), ligase chain reaction (LCR)). A preferable stringent hybridization condition for a DNA:DNA hybridization can be at about 68° C. (in aqueous solution) in 6×SSC or 6×SSPE followed by washing at 68° C.

The present invention additionally provides a polypeptide comprising the amino acid sequence encoded by the gene comprising the nucleotide sequence set forth in SEQ ID NO:1, SEQ ID NO:2, SEQ ID NO:3, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:15, SEQ ID NO:16, SEQ ID NO:17, SEQ ID NO:18, SEQ ID NO:21, SEQ ID NO:23, SEQ ID NO:25, SEQ ID NO:26, SEQ ID NO:27, SEQ ID NO:29, SEQ ID NO:30, SEQ ID NO:31, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:48, SEQ ID NO:49, SEQ ID NO:50, SEQ ID NO:51, SEQ ID NO:52, SEQ ID NO:56, SEQ ID NO:57, SEQ ID NO:58, SEQ ID NO:59, SEQ ID NO:61, SEQ ID NO:62, SEQ ID NO:63, SEQ ID NO:66, SEQ ID NO:67, SEQ ID NO:68, SEQ ID NO:70, SEQ ID NO:71, SEQ ID NO:73, SEQ ID NO:74, SEQ ID NO:76, SEQ ID NO:77, SEQ ID NO:78, SEQ ID NO:79, SEQ ID NO:80, SEQ ID NO:81, SEQ ID NO:83, SEQ ID NO:84, SEQ ID NO:85, SEQ ID NO:86, SEQ ID NO:87, SEQ ID NO:88, SEQ ID NO:89, SEQ ID NO:91, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:112, SEQ ID NO:120, SEQ ID NO:121, SEQ ID NO:122, SEQ ID NO:123, SEQ ID NO:124, SEQ ID NO:125, SEQ ID NO:126, and SEQ ID NO:127 (i.e.., SEQ LIST 1). Additionally, polypeptides comprising the amino acid sequence encoded by a nucleic acid that selectively hybridizes under stringent conditions with a nucleic acid in SEQ LIST 1 are provided. Further, polypeptides comprising the amino acid sequence encoded by a nucleic acid having a region within an exon wherein the region has at least 50, 60, 70, 80, 90, or 95% homology with a nucleic acid in SEQ LIST 1. These polypeptides can be readily obtained by any of several means. For example, the nucleotide sequence of coding regions of the gene can be translated and then the corresponding polypeptide can be synthesized mechanically by standard methods. Additionally, the coding regions of the genes can be expressed or synthesized, an antibody specific for the resulting polypeptide can be raised by standard methods (see, e.g., Harlow and Lane, *Antibodies: A Laboratory Manual*, Cold Spring Harbor Laboratory, Cold Spring Harbor, N.Y., 1988), and the protein can be isolated from other cellular proteins by selective hybridization with the antibody. This protein can be purified to the extent desired by standard methods of protein purification (see, e.g., Sambrook et al., *Molecular Cloning: A Laboratory Manual,* 2nd Ed., Cold Spring Harbor Laboratory, Cold Spring Harbor, N.Y., 1989). The amino acid sequence of any protein, polypeptide or peptide of this invention can be deduced from the nucleic acid sequence, or it can be determined by sequencing an isolated or recombinantly produced protein.

The terms "peptide," "polypeptide" and "protein" can be used interchangeably herein and refer to a polymer of amino acids and includes full-length proteins and fragments thereof. As used in the specification and in the claims, "a" can mean one or more, depending upon the context in which it is used. An amino acid residue is an amino acid formed upon chemical digestion (hydrolysis) of a polypeptide at its peptide linkages. The amino acid residues described herein are preferably in the L isomeric form. However, residues in the D isomeric form can be substituted for any L-amino acid residue, as long as the desired functional property is retained by the polypeptide. Standard polypeptide nomenclature (described in *J. Biol. Chem.*, 243:3552–59 (1969) and adopted at 37 CFR §1.822(b)) is used herein.

As will be appreciated by those skilled in the art, the invention also includes those polypeptides having slight variations in amino acid sequences or other properties. Amino acid substitutions can be selected by known parameters to be neutral (see, e.g., Robinson W E Jr, and Mitchell W M., AIDS 4:S151–S162(1990)). Such variations may arise naturally as allelic variations (e.g., due to genetic polymorphism) or may be produced by human intervention (e.g., by mutagenesis of cloned DNA sequences), such as induced point, deletion, insertion and substitution mutants. Minor changes in amino acid sequence are generally preferred, such as conservative amino acid replacements, small internal deletions or insertions, and additions or deletions at the ends of the molecules. Substitutions may be designed based on, for example, the model of Dayhoff, et al. (in *Atlas of Protein Sequence and Structure* 1978, Nat'l Biomed. Res. Found., Washington, D.C.). These modifications can result in changes in the amino acid sequence, provide silent mutations, modify a restriction site, or provide other specific mutations. Likewise, such amino acid changes result in a different nucleic acid encoding the polypeptides and proteins. Thus, alternative nucleic acids are also contemplated by such modifications.

The present invention also provides cells containing a nucleic acid of the invention. A cell containing a nucleic acid encoding a protein typically can replicate the DNA and, further, typically can express the encoded protein. The cell can be a prokaryotic cell, particularly for the purpose of producing quantities of the nucleic acid, or a eukaryotic cell, particularly a mammalian cell. The cell is preferably a mammalian cell for the purpose of expressing the encoded protein so that the resultant produced protein has mammalian protein processing modifications.

Nucleic acids of the present invention can be delivered into cells by any selected means, in particular depending upon the purpose of the delivery of the compound and the target cells. Many delivery means are well-known in the art. For example, electroporation, calcium phosphate precipitation, microinjection, cationic or anionic liposomes, and liposomes in combination with a nuclear localization signal peptide for delivery to the nucleus can be utilized, as is known in the art.

The present invention also contemplates that the mutated cellular genes necessary for viral growth, produced by the present method, as well as cells containing these mutants can also be useful. These mutated genes and cells containing them can be isolated and/or produced according to the methods herein described and using standard methods.

It should be recognized that the sequences set forth herein may contain minor sequencing errors. Such errors can be corrected, for example, by using the hybridization procedure described above with various probes derived from the described sequences such that the coding sequence can be reisolated and resequenced.

As described in the examples, the present invention provides the discovery of a "serum survival factor" present in serum that is necessary for the survival of persistently virally infected cells. Isolation and characterization of this factor have shown it to be a protein, to have a molecular weight of between about 50 kD and 100 kD, to resist inactivation in low pH (e.g., pH2) and chloroform extraction, to be inactivated by boiling for about 5 minutes and in low ionic strength solution (e.g., about 10 mM to about 50 mM). The present invention thus provides a purified mammalian serum protein having a molecular weight of between about 50 kD and 100 kD which resists inactivation in low pH and resists inactivation by chloroform extraction, which inactivates when boiled and inactivates in low ionic strength solution, and which when removed from a cell culture comprising cells persistently infected with reovirus selectively substantially prevents survival of cells persistently infected with reovirus. The factor, fitting the physical characteristics described above, can readily be verified by adding it to non-serum-containing medium (which previously could not support survival of persistently virally infected cells) and determining whether this medium with the added putative factor can now support persistently virally infected cells, particularly cells persistently infected with reovirus. As used herein, a "purified" protein means the protein is at least of sufficient purity such that an approximate molecular weight can be determined.

The amino acid sequence of the protein can be elucidated by standard methods. For example, an antibody to the protein can be raised and used to screen an expression library to obtain nucleic acid sequence coding the protein. This nucleic acid sequence is then simply translated into the corresponding amino acid sequence. Alternatively, a portion of the protein can be directly sequenced by standard amino acid sequencing methods (amino-terminus sequencing). This amino acid sequence can then be used to generate an array of nucleic acid probes that encompasses all possible coding sequences for a portion of the amino acid sequence. The array of probes is used to screen a cDNA library to obtain the remainder of the coding sequence and thus ultimately the corresponding amino acid sequence.

The present invention also provides methods of detecting and isolating additional serum survival factors. For example, to determine if any known serum components are necessary for viral growth, the known components can be inhibited in, or eliminated from, the culture medium, and it can be observed whether viral growth is inhibited by determining if persistently infected cells do not survive. One can add the factor back (or remove the inhibition) and determine whether the factor allows for viral growth.

Additionally, other, unknown serum components can also be found to be essential for growth. Serum can be fractionated by various standard means, and fractions added to serum free medium to determine if a factor is present in a reaction that allows growth previously inhibited by the lack of serum. Fractions having this activity can then be further fractionated until the factor is relatively free of other components. The factor can then be characterized by standard methods, such as size fractionation, denaturation and/or inactivation by various means, etc. Preferably, once the factor has been purified to a desired level of purity, it is added to cells in serum free medium to confirm that it bestows the function of allowing virus to grow when serum-free medium alone did not. This method can be repeated to confirm the requirement for the specific factor for any desired virus, since each serum factor found to be required by any one virus can also be required by many other viruses. In general, the closer the viruses are related and the more similar the infection modes of the viruses, the more likely that a factor required by one virus will be required by the other.

The present invention also provides methods of treating virus infections utilizing applicants' discoveries. The subject of any of the herein described methods can be any animal, preferably a mammal, such as a human, a veterinary animal, such as a cat, dog, horse, pig, goat, sheep, or cow, or a laboratory animal, such as a mouse, rat, rabbit, or guinea pig, depending upon the virus.

The present invention provides a method of reducing or inhibiting, and thereby treating, a viral infection in a subject, comprising administering to the subject an inhibiting amount of a composition that inhibits functioning of the serum protein described herein, i.e. the serum protein having a molecular weight of between about 50 kD and 100 kD which resists inactivation in low pH and resists inactivation by chloroform extraction, which inactivates when boiled and inactivates in low ionic strength solution, and which when removed from a cell culture comprising cells persistently infected with the virus prevents survival of at least some cells persistently infected with the virus, thereby treating the viral infection. The composition can comprise, for example, an antibody that specifically binds the serum protein, or an antisense RNA that binds an RNA encoded by a gene functionally encoding the serum protein.

Any virus capable of infecting the selected subject to be treated can be treated by the present methods. As described above, any serum protein or survival factor found by the present methods to be necessary for growth of cells infected with any one virus can be found to be necessary for growth of the cells infected with many other viruses. For any given cell-virus combination, the serum protein or factor can be confirmed to be required for growth by the methods described herein. The cellular genes identified by the examples using reovirus, a mammalian pathogen, and a rat cell system have general applicability to other virus infections that include all of the known as well as yet to be discovered human pathogens, including, but not limited to: human immunodeficiency viruses (e.g., HIV-1, HIV-2); parvovirus; papillomaviruses; hantaviruses; influenza viruses (e.g., influenza A, B and C viruses); hepatitis viruses A to G; caliciviruses; astroviruses; rotaviruses; coronaviruses, such as human respiratory coronavirus; picornaviruses, such as human rhinovirus and enterovirus; ebola virus; human herpesvirus (e.g., HSV-1-9); human adenovirus; hantaviruses; for animal, the animal counterpart to any above listed human virus, animal retroviruses, such as simian immunodeficiency virus, avian immunodeficiency virus, bovine immunodeficiency virus, feline immunodeficiency virus, equine infectious anemia virus, caprine arthritis encephalitis virus, arenaviruses, arvoviruses, tickborne virus or visna virus.

A protein inhibiting amount of the composition can be readily determined, such as by administering varying amounts to cells or to a subject and then adjusting the effective amount for inhibiting the protein according to the volume of blood or weight of the subject. Compositions that bind to the protein can be readily determined by running the putatively bound protein on a protein gel and observing an alteration in the protein's migration through the gel. Inhibition of the protein can be determined by any desired means such as adding the inhibitor to complete media used to maintain persistently infected cells and observing the cells' viability. The composition can comprise, for example, an antibody that specifically binds the serum protein. Specific binding by an antibody means that the antibody can be used to selectively remove the factor from serum or inhibit the factor's biological activity and can readily be determined by radio immune assay (RIA), bioassay, or enzyme-linked immunosorbant (ELISA) technology. The composition can comprise, for example, an antisense RNA that specifically binds an RNA encoded by the gene encoding the serum protein. Antisense RNAs can be synthesized and used by standard methods (e.g., *Antisense RNA and DNA*, D. A. Melton, Ed., Cold Spring Harbor Laboratory, Cold Spring Harbor, N.Y. (1988)).

The present methods provide a method of screening a compound for effectiveness in treating or preventing a viral infection, comprising administering the compound to a cell containing a cellular gene functionally encoding a gene product necessary for reproduction of the virus in the cell but not necessary for survival of the cell and detecting the level and/or activity (i.e. function) of the gene product produced, a decrease or elimination of the gene product and/or the gene product activity indicating a compound for treating or preventing the viral infection. The cellular gene can be, for example, a nucleic acid set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:30, SEQ ID NO:31, SEQ ID NO:32, SEQ ID NO:33, SEQ ID NO:34, SEQ ID NO:35, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82; SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, or SEQ ID NO:127 (herein sometimes referred to as SEQ LIST 2, for brevity), any homolog thereof, or any other gene obtained using the methods provided herein for obtaining such genes. It is understood that the cellular gene can be present naturally in the cell being screened, or it can be introduced into the cell in a suitable expression vector, as are well known in the art. The level of the gene product can be measured by any standard means, such as by detection with an antibody specific for the protein. The level of gene product can be compared to the level of the gene product in a control cell not contacted with the compound. The level of gene product can be compared to the level of the gene product in the same cell prior to addition of the compound. Activity, or function, can be measured by any standard means, such as by enzymatic assays that measure the conversion of a substrate to a product or binding assays that measure the binding of a protein to a nucleic acid, for example. Examples of gene products disclosed herein whose activity/function can be measured include tristetraprolin (human ZFP-36), 6-pyruvoyl-tetrahydropterin synthase, a eukaryotic DnaJ-like protein, ID3 (inhibitor of DNA binding 3), N-acetylglucos-aminyltransferase I (mGAT-1), cleavage stimulation factor (CSTF2), TAK1 binding protein, human zinc transcription factor ZPF207, D1x2, Smad7 (Mad-related protein), and P-glycoprotein (mdr1b). The activity can be compared to the activity in a control cell not contacted with the compound or in the same cell prior to addition of the compound. Relatedly, the regulatory region of the gene can he functionally linked to a reporter gene and compounds can be screened for inhibition of the reporter gene. Such reporter constructs are described herein.

The present invention also provides a method of screening a compound for effectiveness in treating or preventing a viral infection comprising contacting the compound with the gene product of a cellular gene comprising a nucleic acid of SEQ LIST 2, or any homolog thereof, and detecting the function of the gene product, a decrease or elimination of the function indicating a compound effective for treating or preventing viral infection. Examples of gene products disclosed herein that can be utilized in this method include tristetraprolin (human ZFP-36), 6-pyruvoyl-tetrahydropterin synthase, a eukaryotic DnaJ-like protein, ID3 (inhibitor of DNA binding 3), N-acetylglucos-aminyltransferase I (mGAT-1), cleavage stimulation factor (CSTF2), TAK1 binding protein, human zinc transcription factor ZPF207, D1x2, Smad7 (Mad-related protein), and P-glycoprotein (mdr1b).

The present invention provides a method of selectively eliminating cells persistently infected with a virus from an animal cell culture capable of surviving for a first period of time in the absence of serum, comprising propagating the cell culture in the absence of serum for a second time period during which a persistently infected cell cannot survive without serum, thereby selectively eliminating from the cell culture cells persistently infected with the virus. The second time period should be shorter than the first time period. Thus one can simply eliminate serum from a standard culture medium composition for a period of time (e.g. by removing serum containing medium from the culture container, rinsing the cells, and adding serum-free medium back to the container), then, after a time of serum starvation, return serum to the culture medium. Alternatively, one can inhibit a serum survival factor from the culture in place of the step of serum starvation. Furthermore, one can instead interfere with the virus-factor interaction. Such a viral elimination method can periodically be performed for cultured cells to ensure that they remain virus-free. The time period of serum removal can greatly vary, with a typical range being about 1 to about 30 days; a preferable period can be about 3 to about 10 days, and a more preferable period can be about 5 days to about 7 days. This time period can be selected based upon ability of a specific cell to survive without serum as well as the life cycle of the target virus, e.g., for reovirus, which has a life cycle of about 24 hours, 3 days' starvation of cells provides dramatic results.

Furthermore, the time period can be shortened by also passaging the cells during the starvation; in general, increasing the number of passages can decrease the time of serum starvation (or serum factor inhibition) needed to get full clearance of the virus from the culture. While passaging, the cells typically are exposed briefly to serum (typically for about 3 to about 24 hours). This exposure both stops the action of the trypsin used to dislodge the cells and stimulates the cells into another cycle of growth, thus aiding in this selection process. Thus a starvation/serum cycle can be repeated to optimize the selective effect. Other standard culture parameters, such as confluency of the cultures, pH, temperature, etc. can be varied to alter the needed time period of serum starvation (or serum survival factor inhibition). This time period can readily be determined for any given viral infection by simply removing the serum for various periods of time, then testing the cultures for the presence of the infected cells (e.g., by ability to survive in the absence of serum and confirmed by quantitating virus in cells by standard virus titration and immunohistochemical techniques) at each tested time period, and then detecting at which time periods of serum deprivation the virally infected cells were eliminated. It is preferable that shorter time periods of serum deprivation that still provide elimination of the persistently infected cells be used. Furthermore, the cycle of starvation, then adding back serum and determining amount of virus remaining in the culture can be repeated until no virtually infected cells remain in the culture.

Thus, the present method can further comprise passaging the cells, i.e., transferring the cell culture from a first container to a second container. Such transfer can facilitate the selective lack of survival of virally infected cells. Transfer can be repeated several times. Transfer is achieved by standard methods of tissue culture (see, e.g., Freshney, *Culture of Animal Cells, A Manual of Basic Technique,* 2nd Ed. Alan R. Liss, Inc., New York, 1987).

The present method further provides a method of selectively eliminating from a cell culture cells persistently infected with a virus, comprising propagating the cell culture in the absence of a functional form of the serum protein having a molecular weight of between about 50 kD and 100 kD which resists inactivation in low pH and resists inactivation by chloroform extraction, which inactivates when boiled and inactivates in low ionic strength solution, and which when removed from a cell culture comprising cells persistently infected with reovirus substantially prevents survival of cells persistently infected with reovirus. The absence of the functional form can be achieved by any of several standard means, such as by binding the protein to an antibody selective for it (binding the antibody in serum either before or after the serum is added to the cells; if before, the serum protein can be removed from the serum by, e.g., binding the antibody to a column and passing the serum over the column and then administering the survival protein-free serum to the cells), by administering a compound that inactivates the protein, or by administering a compound that interferes with the interaction between the virus and the protein.

Thus, the present invention provides a method of selectively eliminating from a cell culture propagated in serum-containing medium cells persistently infected with a virus, comprising inhibiting in the serum the protein having a molecular weight of between about 50 kD and 100 kD which resists inactivation in low pH and resists inactivation by chloroform extraction, which inactivates when boiled and inactivates in low ionic strength solution, and which when removed from a cell culture comprising cells persistently infected with reovirus substantially prevents survival of cells persistently infected with reovirus. Alternatively, the interaction between the virus and the serum protein can be disrupted to selectively eliminate cells persistently infected with the virus.

Any virus capable of some form of persistent infection may be eliminated from a cell culture utilizing the present elimination methods, including removing, inhibiting or otherwise interfering with a serum protein, such as the one exemplified herein, and also including removing, inhibiting or otherwise interfering with a gene product from any cellular gene found by the present method to be necessary for viral growth yet nonessential to the cell. For example, DNA viruses or RNA viruses can be targeted. One can readily determine whether cells infected with a selected virus can be selectively removed from a culture through removal of serum by starving cells permissive to the virus of serum (or inhibiting the serum survival factor), adding the selected virus to the cells, adding serum to the culture, and observing whether infected cells die (i.e., by titering levels of virus in the surviving cells with an antibody specific for the virus).

A culture of any animal cell (i.e., any cell that is typically grown and maintained in culture in serum) that can be maintained for a period of time in the absence of serum, can be purified from viral infection utilizing the present method. For example, primary cultures as well as established cultures and cell lines can be used. Furthermore, cultures of cells from any animal and any tissue or cell type within that animal that can be cultured and that can be maintained for a period of time in the absence of serum can be used. For example, cultures of cells from tissues typically infected, and particularly persistently infected, by an infectious virus could be used.

As used in the claims "in the absence of serum" means at a level at which persistently virally infected cells do not survive. Typically, the threshold level is about 1% serum in the media. Therefore, about 1% serum or less can be used, such as about 1%, 0.75%, 0.50%, 0.25% 0.1% or no serum can be used.

As used herein, "selectively eliminating" cells persistently infected with a virus means that substantially all of the cells persistently infected with the virus are killed such that the presence of virally infected cells cannot be detected in the culture immediately after the elimination procedure has been performed. Furthermore, "selectively eliminating" includes that cells not infected with the virus are generally not killed by the method. Some surviving cells may still produce virus but at a lower level, and some may be defective in pathways that lead to death by the virus. Typically, for cells persistently infected with virus to be substantially all killed, more than about 90% of the cells, and more preferably more than about 95%, 98%, 99%, or 99.99% of virus-containing cells in the culture are killed.

The present method also provides a nucleic acid comprising the regulatory region of any of the genes. Such regulatory regions can be isolated from the genomic sequences isolated and sequenced as described above and identified by any characteristics observed that are characteristic for regulatory regions of the species and by their relation to the start codon for the coding region of the gene. The present invention also provides a construct comprising the regulatory region functionally linked to a reporter gene. Such constructs are made by routine subcloning methods, and many vectors are available into which regulatory regions can be subcloned upstream of a marker gene. Marker genes can be chosen for ease of detection of marker gene product.

The present method therefore also provides a method of screening a compound for treating a viral infection, comprising administering the compound to a cell containing any of the above-described constructs, comprising a regulatory region of one of the genes comprising any of the nucleotide sequences set forth in SEQ LIST 2, or any homologs thereof, whose inhibition or reduction in expression causes inhibition of viral replication wherein the region is functionally linked to a reporter gene, and detecting the level of the reporter gene product produced, a decrease or elimination of the reporter gene product indicating a compound for treating the viral infection. Compounds detected by this method would inhibit transcription of the gene from which the regulatory region was isolated, and thus, in treating a subject, would inhibit the production of the gene product produced by the gene, and thus treat the viral infection.

Some genes when disrupted by the present method of retrovirus insertion, resulted in over expression of the gene product, and this overexpression inhibited viral replication. Thus the present invention provides a method of screening a compound for effectiveness in treating a viral infection, comprising administering the compound to a cell containing a cellular gene functionally encoding a gene product whose overexpression inhibits reproduction of the virus but does not prevent survival of the cell and detecting the level of the gene product produced, an increase in the gene product indicating a compound effective for treating the viral infection. Typically, an increase will be a 10%, 20%, 30%, 40%, 50%, 60%, 70%, 80%, 90%, 100%, 125%, 150%, 175%, 200%, 300%, 400%, 500% or higher increase over gene product produced when the compound is not present.

The present invention additionally provides a method of reducing or inhibiting a viral infection in a subject, comprising administering to the subject an amount of a composition that inhibits expression or functioning of a gene product encoded by a gene comprising the nucleic acid set forth in any of SEQ LIST 2, or a homolog thereof, thereby treating the viral infection. Reducing or inhibiting viral infection naturally can include both the initial infection of the subject and the infection of uninfected cells within an already infected subject, e.g. inhibiting viral replication in cells of the subject. The composition can comprise, for example, an antibody that binds a protein encoded by the gene. The composition can also comprise an antibody that binds a receptor for a protein encoded by the gene. Such an antibody can be raised against the selected protein by standard methods as set forth above, and can be either polyclonal or monoclonal, though monoclonal is preferred. Alternatively, the composition can comprise an antisense RNA that binds an RNA encoded by the gene, as described above. Examples of antisense RNA useful therapeutically include the fragments of the nucleic acids described above. Furthermore, the composition can comprise a nucleic acid functionally encoding an antisense RNA that binds an RNA encoded by the gene. Other useful compositions will be readily apparent to the skilled artisan.

The present invention also provides a method of treating a viral infection in a subject comprising administering to the subject a treatment effective amount of a composition that increases expression of a gene whose over expression reduces or inhibits viral replication. Typically, an increase will be a 10%, 20%, 30%, 40%, 50%, 60%, 70%, 80%, 90%, 100%, 125%, 150%, 175%, 200%, 300%, 400%, 500% or higher increase over gene product produced when the composition is not present.

The present invention further provides a method of reducing or inhibiting a viral infection in a subject comprising mutating ex vivo in a selected cell, for example from the subject or from an allogenic source, an endogenous gene comprising a nucleic acid set forth in SEQ LIST 2 whose inhibition or reduction in expression causes inhibition of viral replication, or a homolog thereof, to a gene form incapable of producing a functional gene product of the gene or a gene form producing a reduced amount of a functional gene product of the gene, and placing (or replacing, in the case of the subject's own cells) the cell in the subject, thereby reducing viral infection of cells in the subject. The cell can be selected according to the typical target cell of the specific virus whose infection is to be reduced, prevented or inhibited. A preferred cell for several viruses is a hematopoietic cell. When the selected cell is a hematopoietic cell, viruses which can be reduced or inhibited from infection can include, for example, HIV, including HIV-1 and HIV-2. However, many other virus-cell combinations will be apparent to the skilled artisan.

The invention also includes a method of reducing or inhibiting viral infection in a subject comprising mutating ex vivo in a selected cell, for example from a subject or an allogenic source, an endogenous gene comprising a nucleic acid set forth in SEQ LIST 2 whose overexpression causes inhibition of viral replication, or a homolog thereof, to a gene form that expresses the gene at a higher level than the endogenous gene, and placing or replacing the cell in the subject. Typically, a higher level can be 10%, 20%, 30%, 40%, 50%, 60%, 70%, 80%, 90%, 100%, 125%, 150%, 175%, 200%, 300%, 400%, 500% or higher than the non-mutated, endogenous gene. The cell can be selected according to the typical target cell of the specific virus whose infection is to be reduced, prevented or inhibited. A preferred cell for several viruses is a hematopoietic cell. When the selected cell is a hematopoietic cell, viruses which can be reduced or inhibited from infection can include, for example, HIV, including HIV-1 and HIV-2. However, many other virus-cell combinations will be apparent to the skilled artisan.

The present invention additionally provides a method of increasing viral infection resistance in a subject comprising mutating ex vivo in a selected cell, for example from the subject or from an allogenic source, an endogenous gene comprising a nucleic acid set forth in SEQ LIST 2, whose inhibition or reduction in expression increases viral infection resistance, said endogenous gene being mutated to a mutated gene form incapable of producing a functional gene product of the gene or a gene form producing a reduced amount of a functional gene product of the gene, and placing the cell in the subject, thereby increasing viral infection resistance of cells in the subject. The virus can be HIV, particularly when the cell is a hematopoietic cell. However, many other virus-cell combinations will be apparent to the skilled artisan.

Furthermore, the present invention provides a method for isolation of cellular genes utilized in tumor progression. The present invention provides a method of identifying a cellular gene that can suppress a malignant phenotype in a cell, comprising (a) transferring into a cell culture incapable of growing well in soft agar or Matrigel a vector encoding a selective marker gene lacking a functional promoter, (b) selecting cells expressing the marker gene, and (c) isolating from selected cells which are capable of growing in soft agar or Matrigel a cellular gene within which the marker gene is inserted, thereby identifying a gene that can suppress a malignant phenotype in a cell. This method can be performed using any selected non-transformed cell line, of which many are known in the art.

The present invention additionally provides a method of identifying a cellular gene that can suppress a malignant phenotype in a cell, comprising (a) transferring into a cell culture of non-transformed cells a vector encoding a selective marker gene lacking a functional promoter, (b) selecting cells expressing the marker gene, and (c) isolating from selected and transformed cells a cellular gene within which the marker gene is inserted, thereby identifying a gene that can suppress a malignant phenotype in a cell. A non-transformed phenotype can be determined by any of several standard methods in the art, such as the exemplified inability to grow in soft agar, or inability to grow in Matrigel.

The present invention further provides a method of screening for a compound for suppressing a malignant phenotype in a cell comprising administering the compound to a cell containing a cellular gene functionally encoding a gene product involved in establishment of a malignant phenotype in the cell and detecting the level of the gene product produced, a decrease, inhibition or elimination of the gene product indicating a compound effective for suppressing the malignant phenotype. Detection of the level, or amount, of gene product produced can be measured, directly or indirectly, by any of several methods standard in the art (e.g., protein gel, antibody-based assay, detecting labeled RNA) for assaying protein levels or amounts, and selected based upon the specific gene product.

The present invention also provides a method of screening for a compound for suppressing a malignant phenotype in a cell comprising administering the compound to a cell containing a cellular gene functionally encoding a gene product whose overexpression is involved in suppressing a malignant phenotype in the cell and detecting the level of the gene product produced, an increase in the gene product indicating a compound effective for suppressing the malignant phenotype.

The present invention further provides a method of suppressing a malignant phenotype in a cell in a subject, comprising administering to the subject an amount of a composition that inhibits expression or functioning of a gene product encoded by a gene comprising the nucleic acid set forth in SEQ ID NO:9, SEQ ID NO:10, SEQ ID NO:26, SEQ ID NO:27, SEQ ID NO:28, SEQ ID NO:29, SEQ ID NO:36 or SEQ ID NO:94, or a homolog thereof, or any gene whose overexpression is found by the present method to be involved in suppressing a malignant phenotype in the cell (e.g., any clone designated herein with an "x") thereby suppressing a malignant phenotype. The composition can, for example, comprise an antibody that binds a protein encoded by the gene. The composition can, as another example, comprise an antibody that binds a receptor for a protein encoded by the gene. The composition can comprise an antisense RNA that binds an RNA encoded by the gene. Further, the composition can comprise a nucleic acid functionally encoding an antisense RNA that binds an RNA encoded by the gene.

The present invention further provides a method of suppressing a malignant phenotype in a cell in a subject, comprising administering to the subject an amount of a composition that increases expression of a gene product whose overexpression is involved in suppressing a malignant phenotype in the cell. The gene product can be the product of a gene wherein disruption of an upstream gene by the present vector resulted in overexpression of the downstream gene, and the overexpression of the downstream gene demonstrated a transformed phenotype. The composition can be, for example, an inhibitor, such as a small molecule inhibitor, of the COX 2 enzyme.

Diagnostic or therapeutic agents of the present invention can be administered to a subject or an animal model by any of many standard means for administering therapeutics or diagnostics to that selected site or standard for administering that type of functional entity. For example, an agent can be administered orally, parenterally (e.g., intravenously), by intramuscular injection, by intraperitoneal injection, topically, transdermally, or the like. Agents can be administered, e.g., as a complex with cationic liposomes, or encapsulated in anionic liposomes. Compositions can include various amounts of the selected agent in combination with a pharmaceutically acceptable carrier and, in addition, if desired, may include other medicinal agents, pharmaceutical agents, carriers, adjuvants, diluents, etc. Parental administration, if used, is generally characterized by injection. Injectables can be prepared in conventional forms, either as liquid solutions or suspensions, solid forms suitable for solution or suspension in liquid prior to injection, or as emulsions. Depending upon the mode of administration, the agent can be optimized to avoid degradation in the subject, such as by encapsulation, etc.

Dosages will depend upon the mode of administration, the disease or condition to be treated, and the individual subject's condition, but will be that dosage typical for and used in administration of antiviral or anticancer agents. Dosages will also depend upon the composition being administered, e.g., a protein or a nucleic acid. Such dosages are known in the art. Furthermore, the dosage can be adjusted according to the typical dosage for the specific disease or condition to be treated. Furthermore, viral titers in culture cells of the target cell type can be used to optimize the dosage for the target cells in vivo, and transformation from varying dosages achieved in culture cells of the same type as the target cell type can be monitored. Often a single dose can be sufficient; however, the dose can be repeated if desirable. The dosage should not be so large as to cause adverse side effects. Generally, the dosage will vary with the age, condition, sex and extent of the disease in the patient and can be determined by one of skill in the art. The dosage can also be adjusted by the individual physician in the event of any complication.

For administration to a cell in a subject, the composition, once in the subject, will of course adjust to the subject's body temperature. For ex vivo administration, the composition can be administered by any standard methods that would maintain viability of the cells, such as by adding it to culture medium (appropriate for the target cells) and adding this medium directly to the cells. As is known in the art, any medium used in this method can be aqueous and non-toxic so as not to render the cells non-viable. In addition, it can contain standard nutrients for maintaining viability of cells, if desired. For in vivo administration, the complex can be added to, for example, a blood sample or a tissue sample from the patient, or to a pharmaceutically acceptable carrier, e.g., saline and buffered saline, and administered by any of several means known in the art. Examples of administration include parenteral administration, e.g., by intravenous injection including regional perfusion through a blood vessel supplying the tissues(s) or organ(s) having the target cell(s), or by inhalation of an aerosol, subcutaneous or intramuscular injection, topical administration such as to skin wounds and lesions, direct transfection into, e.g., bone marrow cells prepared for transplantation and subsequent transplantation into the subject, and direct transfection into an organ that is subsequently transplanted into the subject. Further administration methods include oral administration, particularly when the composition is encapsulated, or rectal administration, particularly when the composition is in suppository form. A pharmaceutically acceptable carrier includes any material that is not biologically or otherwise undesirable, i.e., the material may be administered to an individual along with the selected complex without causing any undesirable biological effects or interacting in a deleterious manner with any of the other components of the pharmaceutical composition in which it is contained.

Specifically, if a particular cell type in vivo is to be targeted, for example, by regional perfusion of an organ or tumor, cells from the target tissue can be biopsied and optimal dosages for import of the complex into that tissue can be determined in vitro, as described herein and as known in the art, to optimize the in vivo dosage, including concentration and time length. Alternatively, cultured cells of the same cell type can also be used to optimize the dosage for the target cells in in vivo.

For either ex vivo or in vivo use, the complex can be administered at any effective concentration. An effective concentration is that amount that results in reduction, inhibition or prevention of the viral infection or in reduction or inhibition of the transformed phenotype of the cells.

A nucleic acid can be administered in any of several means, which can be selected according to the vector utilized, the organ or tissue, if any, to be targeted, and the characteristics of the subject. The nucleic acids, if desired in a pharmaceutically acceptable carrier such as physiological saline, can be administered systemically, such as intravenously, intraarterially, orally, parenterally, subcutaneously. The nucleic acids can also be administered by direct injection into an organ or by injection into the blood vessel supplying a target tissue. For an infection of cells of the lungs or trachea, it can be administered intratracheally. The nucleic acids can additionally be administered topically, transdermally, etc.

The nucleic acid or protein can be administered in a composition. For example, the composition can comprise other medicinal agents, pharmaceutical agents, carriers, adjuvants, diluents, etc. Furthermore, the composition can comprise, in addition to the vector, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a vector and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95–100 (1989); Felgner et al. *Proc. Natl. Acad. Sci USA* 84:7413–7417 (1987); U.S. Pat. No. 4,897,355.

For a viral vector comprising a nucleic acid, the composition can comprise a pharmaceutically acceptable carrier such as phosphate buffered saline or saline. The viral vector can be selected according to the target cell, as known in the art. For example, adenoviral vectors, in particular replication-deficient adenoviral vectors, can be utilized to target any of a number of cells, because of its broad host range. Many other viral vectors are available, and their target cells are known.

Throughout this application, various publications are referenced. The disclosures of these publications in their entireties are hereby incorporated by reference into this application in order to more fully describe the state of the art to which this invention pertains.

EXAMPLES

Selective Elimination of Virally Infected Cells from a Cell Culture

Rat intestinal cell line-1 cells (RIE-1 cells) were standardly grown in Dulbecco's modified Eagle's medium, high glucose, supplemented with 10% fetal bovine serum. To begin the experiment, cells persistently infected with reovirus were grown to near confluence, then serum was removed from the growth medium by removing the medium, washing the cells in PBS, and returning to the flask medium not supplemented with serum. Typically, the serum content was reduced to 1% or less. The cells are starved for serum for several days, or as long as about a month, to bring them to quiescence or growth arrest. Media containing 10% serum is then added to the quiescent cells to stimulate growth of the cells. Surviving cells are found to not be persistently infected cells by immunohistochemical techniques used to establish whether cells contain any infectious virus (sensitivity to 1 infectious virus per ml of homogenized cells).

Cellular Genomic DNA Isolation

Gene Trap Libraries: The libraries are generated by infecting the RIE-1 cells with a retrovirus vector (U3 gene-trap) at a ratio of less than one retrovirus for every ten cells. When a U3 gene trap retrovirus integrates within an actively transcribed gene, the neomycin resistance gene that the U3 gene trap retrovirus encodes is also transcribed, thus conferring resistance to the cell to the antibiotic neomycin. Cells with gene trap events are able to survive exposure to neomycin while cells without a gene trap event die. The various cells that survive neomycin selection are then propagated as a library of gene trap events. Such libraries can be generated with any retrovirus vector that has the properties of expressing a reporter gene from a transcriptionally active cellular promoter that tags the gene for later identification.

Reovirus selection: Reovirus infection is typically lethal to RIE-1 cells but can result in the development of persistently infected cells. These cells continue to grow while producing infective reovirus particles. For the identification of gene trap events that confer reovirus resistance to cells, the persistently infected cells must be eliminated or they will be scored as false positives. We have found that RIE-1 cells persistently infected with reovirus are very poorly tolerant to serum starvation, passaging and plating at low density. Thus, we have developed protocols for the screening of the RIE-1 gene trap libraries that select against both reovirus sensitive cells and cells that are persistently infected with reovirus.

1. RIE-1 library cells are grown to near confluence and then the serum is removed from the media. The cells are starved for serum for several days to bring them to quiescent or growth arrest.
2. The library cells are infected with reovirus at a titer of greater than ten reovirus per cell and the serum starvation is continued for several more days.
3. The infected cells are passaged, (a process in which they are exposed to serum for three to six hours) and then starved for serum for several more days.
4. The surviving cells are then allowed to grow in the presence of serum until visible colonies develop at which point they are cloned by limiting dilution.

MEDIA: DULBECCO'S MODIFIED EAGLE'S MEDIUM, HIGH GLUCOSE (DME/HIGH) Hyclone Laboratories cat. no. SH30003.02.

NEOMYCIN: The antibiotic used to select against the cells that did not have a U3 gene trap retrovirus, e.g. GENETICIN, from Sigma. [cat. no. G9516].

RAT INTESTINAL CELL LINE-1 CELLS (RIE-1 CELLS): These cells are from the laboratory of Dr. Ray Dubois (VAMC). They are typically cultured in Dulbecco's Modified Eagle's Medium supplemented with 10% fetal calf serum.

REOVIRUS: Laboratory strains of either serotype 1 or serotype 3 are used. They were originally obtained from the laboratories of Bernard N. Fields (deceased). These viruses have been described in detail.

RETROVIRUS: The U3 gene trap retrovirus used here were developed by Dr. Earl Ruley (VAMC) and the libraries were produced using a general protocol suggested by him.

SERUM: FETAL BOVINE SERUM Hyclone Laboratories cat. no. A-1115-L.

Identification Tags for Isolated Nucleic Acids

Genomic sequences, tagged with a vector, such as the U3 gene trap vector, are given a number corresponding to the genomic library of mutant cells from which the sequence was isolated, and a letter indicating a unique member of the library. More than one sequence with the same number and letter indicates multiple, unique sequences obtained from the genome surrounding the vector insert that "tagged" the gene. Such genomic sequences are obtained using vector-based primers, from which sequencing occurs 3' to 5' or 5' to 3'. In the former case, to recover the orientation of the gene into which the vector inserted, the sequence derived from the vector primer must be reversed and complemented. Such reverse complement sequences are designated "rE". In the case of genome sequencing from a primer that occurs 5' to 3' (i.e. the primer is at the 3' end of the vector), no changes are needed, since the derived sequence is the sequence as it appears in the gene disrupted. Such sequences are designated "B4". Homologies indicated below each genomic sequence are in the positive direction, unless explicitly noted to be on the negative strand. As an example, SEQ ID NO. 27 comprises a nucleic acid sequence encoding a novel polypeptide on the positive strand, while the negative strand encodes ferritin.

| SEQ ID NO: | Lab Designation |
|---|---|
| 1 | 32-3-2#1E/-rE |
| 2 | L191B2E#1-RE |
| 3 | L191B2E#3+-rE |
| 4 | 21-5-9E-RE |
| homology to: emb/AL021154/HS15005 human DNA sequence | |
| 5 | 14A14E-rE |
| 6 | 4cx-b4 |
| 7 | 5a-b4 |
| 8 | 6BSA12-B4 |
| 9 | X7B/B4 |
| 10 | x27b4f__1 |
| 11 | 12C#A-rE |
| 12 | 10-3b(5/2/96)/-rE |
| 13 | 10__4B__4-rE |
| 14 | 6BE60-rE |
| homology to: alpha-trophomyosin | |
| 15 | 19D3E-rE |
| 16 | L19D16E-rE |
| 17 | 2b__rE |
| 18 | 14__24__#6-rE |
| 19 | 7A7'-rE |
| homology to: annexin II/dynein I | |
| 20 | L12cx#6-rE |
| homology to: gb:X51760 human zinc finger protein ZFP-36 | |
| 21 | L12cx#11-rE |
| 22 | 19D5E-rE |
| homology to: 6-pyruvoyl-tetrahydropterin synthase (gb/M77850/RAT6PTHS) | |
| 23 | 12__3b#7-rE |
| 24 | 12__3B#8-RE |
| homology to: gb/AA871174/vq32a08.r1 Barskad bowel MPLRBg Mus musculus cDNA clone 10959265' | |
| 25 | 9B27-2-E |
| homology to: RAT LOCUS RNU53922 04-MAY-1996; *Rattus norvegicus* DnaJ-like protein (RDJ1) mRNA, complete Cds, ACCESSION U53922 (on negative strand) | |
| 26 | x15-rE |
| 27 | X11-rE |
| homology to: ferritin H (on the negative strand) | |
| 28 | X20-rE |
| homology to: LOCUS RATGL5A Rat NICER element (GL5-14)5' long terminal repeat, Acc.No. M59028 M33535N1D | |
| 29 | X4-rE |
| 30 | 14A7E-rE |
| homology to: MMSMAD7 3681 bp mRNA ROD 31-JUL-1998 DEFINITION Mus musculus mRNA for Mad-related protein Smad7 ,149 bases | |
| 31 | 14A13E-rE |
| 32 | 14__7#2E-rE |
| homology to: N-acetylglucosaminyltransferase 1 | |
| 33 | 12CX#6-rE |
| homology to: gb\|AA522204\|AA522204 vf98g09__r1 Soares mouse mammary gland NbMMG Mus musculus cDNA clone 851872; also 5' similar to gb X51760 zinc finger protein ZFP-36 (HUMAN), gb L20450 Mus musculus DNA-binding protein mRNA, complete cds (MOUSE); Length = 442, 925 bases (shares homology with SEQ ID NO:20) | |
| 34 | 12C__2B#9E-rE |
| 35 | 12CX#11E-rE |
| 36 | x5-rE |
| 37 | 8C5__11-rE |
| 38 | 191E2E-rE |
| 39 | 19__7AE-rE |
| 40 | 19__9BE-rE |
| homology to: LOCUS HS347M6 56583 bp DNA PRI 14-JAN-1998 Human DNA sequence from PAC 347M6 on chromosome Xq22, CSTF2 (Cleavage Stimulation Factor, CF-1, Polyadenylation Factor) 64 kD subunit gene | |
| 41 | 191E9E-rE |
| 42 | 191E8E-rE |
| 43 | 14C__2E/-rE |
| homology to: gb/H31084/EST104778 Rattus sp. cDNA - 5' end similar to signal recognition particle subunit(19 kDa) (on negative strand) | |
| 44 | 14H1E-rE |
| 45 | 14G3E-rE |
| 46 | 14G__2E-rE |
| 47 | 6__3__6__2E/-rE |
| homology to: *Rattus norvegicus* cis-golgi gp130 (on negative strand); and a HUMAN EST (on positive strand) A1127398; qb70g11.x1 Soares fetal heart NbHH19W Homo sapiens cDNA clone (1705508 3' mRNA sequence) | |
| 48 | 14H4E/-rE |
| 49 | 18A__8__4E-rE |
| 50 | 18A__8__1E-rE |
| 51 | SCB2__19E-rE |
| 52 | L197B3E-rE |
| 53 | L195C5E-rE |
| homology to: *H. pylori* and *C.jeuni* | |
| 54 | 21__5__7E-rE |
| homology to: id3 gene; emb\|AL021154\|HS150O5 Human DNA sequence from clone 15005; HTGS phase 1 [Homo sapiens]; containing the E2F2 gene for transcription factor E2F-2 and the ID3 gene for Inhibitor of DNA binding 3 (dominant negative helix-loop-helix protein), 1R2, Length = 133667, 971 bases | |
| 55 | L195B1E-rE |
| homology to: vK72b07.s1 Knowles Solter mouse 2 cell Mus musculus cDNA clone 960181 5' | |
| 56 | L194c4E-rE |
| 57 | L193A1E#A-rE |
| 58 | L192A3E-rE |
| 59 | L1739E-rE |
| 60 | L192B3E#13-rE |
| contains sequence identical to: insulin growth factorII/mannose-6-phosphate receptor | |
| 61 | 3 2 4 rE |
| located in the same region of the genome as calcyclin, but the gene is "read" in the opposite direction | |
| 62 | 36 7 1 a-rE |
| 63 | 36 5 1 4 a-rE |
| 64 | 34 25 5a-rE |
| rat satellite DNA (RATRSSID 93 bp, ROD 12-MAR-1984) | |
| 65 | 34 24-126/rE |
| homology to: HSU49928 (3096 bp mRNA) PRI 06-APR-1998, Homo sapiens TAK1 binding protein (TAB1) mRNA, complete cds, ACCESSION U49928 | |

-continued

| SEQ ID NO: | Lab Designation |
|---|---|
| NID g1401125, and HS333H23 (142274 bp DNA) HTG 17-JUL-1998 Human DNA sequence | |
| 66 | 34 23-1/rE |
| 67 | 36 5 2-6/rE |
| 68 | 36 5 2-196/rE |
| 69 | 34 23-3/rE |
| homology to: gb|L16546|RATAP1X Rat P-glycoprotein (mdr1b) gene | |
| 70 | 34 25 23-rE |
| 71 | 36 5 2-196/rE |
| 72 | 31 3 9/rE |
| homology to: AA798638 568 bp mRNA EST 10-FEB-1998, vw34b06.r1 Soares mouse mammary gland NbMMG Mus musculus cDNA clone1245683 5, mRNA sequence, 824 bases. | |
| 73 | 31 3 6-2-rE |
| 74 | 31 3 17-rE |
| 75 | 31 3 5-rE |
| homology to: AF046001 2347 bp mRNA PRI 19-FEB-1998, Homo sapiens zinc finger transcription factor (ZNF207) mRNA, complete Cds, 833 bases. | |
| 76 | 31 3 15#1/rE |
| 77 | 24 3 5#1/rE |
| 78 | 31 4 4#1/rE |
| 79 | 31 3 19#2/rE |
| 80 | 31 4 5#1/rE |
| 81 | 24 9 3#2/rE |
| 82 | L24_26_1-BL |
| homology to: AI045472 396 bp mRNA EST 06-JUL-1998, UI-R-C1-jz-h-09-0-UI.s2 UI-R-C1 Rattus norvegicus cDNA cloneUI-R-C1-jz-h-09-0-UI 3', mRNA sequence. | |
| 83 | L24_26_1-B4 |
| 84 | L22_5A1/rE |
| 85 | L24_3_2B/rE |
| 86 | L24 4-2/rE |
| 87 | L24 5-2/rE |
| 88 | L24 5-3/rE |
| 89 | (15-)L28AP/rE |
| 90 | L24 26-10/rE |
| homology to: LOCUS R06687 403 bp mRNA EST 03-APR-1995; yf10a10.r1 Soares fetal liver spleen 1NFLS Homo sapiens cDNA clone 126426 5' | |
| 91 | L24 26-2A/rE |
| 92 | L24 26-2B/rE |
| homology to: gb|AA590026|AA590026 vm22g03.r1 Knowles Solter mouse blastocyst B1 Mus musculus cDNA clone 990964 , 459 bases, 139A; and Rattus norvegicus Eker rat-associated intracisternal-A particle element | |
| 93 | 14 7#2E-rE |
| homology to: N-acetylglucosaminyltransferase 1; this sequence shares homology with SEQ ID NO:32. | |
| 94 | x18 |
| 95 | 31_3_9-rE |
| 96 | 31_3_6_2-rE |
| 97 | 31_3_17-rE |
| 98 | 31_3_15#1-rE |
| 99 | 24_3_5#1-rE |
| 100 | 31_4_4#1-rE |
| 101 | 31_3_19#2-rE |
| 102 | 31_4_5#1-rE |
| 103 | 24_9_3#2-rE |
| 104 | 14XD#12E-rE |
| 105 | 70A-rE |
| 106 | 31-3-4-rE |
| 107 | 3_6_9-NeoG-rE |
| 108 | 31_4_2-rE |
| 109 | 3_2_13-rE |
| homology to: calcyclin | |
| 110 | 3_2_4-E |
| homology to: pistlre-alpha 1 (with homology to calcyclin on negative strand) | |
| 111 | L25-10/-rE |
| homology to: calcyclin | |
| 112 | L24-4-3/-rE |
| 113 | L24-9-1-rE |
| rat id sequence | |
| 114 | 17-L25-27#7-rE |
| homology to: calcyclin | |
| 115 | L21C1E-rE |
| homology to: calcyclin | |
| 116 | L24-5-3BE-rE |
| homology to: LOCUS H32572 310 bp mRNA EST 08-SEP-1995 EST107805 Rat PC-12 cells, untreated Rattus sp cDNA 5' end, ACCESSION H32572, and LOCUS AA858747 470 bp mRNA EST 10-MAR-1998 UI-R-A0-bb-e-01-0-UI.s1 UI-R-A0 Rattus norvegicus cDNA clone UI-R-A0-bb-e-01-0-UI, 3' similar to gb|AA473081|AA473081 vd44b07-r1 Barstead MPLRB1 Mus musculus cDNA clone 803413 5' mRNA sequence | |
| 117 | L24-4-2BE-rE |
| homology to: LOCUS MMU51002 6495 bp DNA ROD 16-JAN-1997 Mus musculus Dlx-2 gene, complete cds, ACCESSION U51002 NID g1477589 | |
| 118 | 17-3-3B-B4 |
| 119 | L24-26-3/-rE |
| homology to: RNU23776, DNA ROD 10-AUG-1995, Rattus norvegicus Eker rat-associated intracisternal-A particle element | |
| 120 | 12_2B#2-rE |
| 121 | 05-17-3-3He-1-T7 |
| 122 | 21_5_8E-rE |
| homology to: emb|AL021154|HS150O5 Human DNA sequence from clone 150O5; 1p36_13-36_22, contains the E2F2 gene for transcription factor E2F-2 and the ID3 gene for Inhibitor of DNA binding 3(dominant negative helix-loop-helix protein, 1R2, Length = 133667,971 bases | |
| 123 | X18H-t7 |
| 124 | 18A_8_4E-rE |
| 125 | L24-5-2BE-rE |
| 126 | L24-4-2AE-rE |
| 127 | L24-10-1BE-rE |

Genes Necessary for Viral Infection

Some of the isolated sequences dislcosed here comprise sequence encoding the following proteins: tristetraprolin (human ZFP-36), 6-pyruvoyltetrahydropterin synthase, a eukaryotic DnaJ-like protein, ID3 (inhibitor of DNA binding 3), N-acetylglucos-aminyltransferase 1 (mGAT-1), cleavage stimulation factor (CSTF2), TAK1 binding protein, human zinc transcription factor ZPF207, D1x2, Smad7 (Mad-related protein), and P-glycoprotein (mdr1b).

Isolation of Cellular Genes that Suppress a Malignant Phenotype

We have utilized a gene-trap method of selecting cell lines that have a transformed phenotype (are potentially tumor cells) from a population of cells (RIE-1 parentals) that are not transformed. The parental cell line, RIE-1 cells, does not have the capacity to grow in soft agar or to produce tumors in mice. Following gene-trapping, cells were screened for their capacity to grow in soft agar. These cells were cloned and genomic sequences were obtained 5' or 3' of the retrovirus vector, i.e. SEQ ID NO:9, SEQ ID NO:10, SEQ ID NO:26, SEQ ID NO:27, SEQ ID NO:28, SEQ ID NO:29, SEQ ID NO:36 or SEQ ID NO:94; sequences designated with an "x" in the clone name). All of the cell lines behave as if they are tumor cell lines, as they also induce tumors in mice.

Of the cell lines, two are associated with the enhanced expression of the prostaglandin synthetase gene II or COX 2. It has been shown that disruption of gene function by retroviral targeting of an upstream gene has lead to increased expression of a downstream gene product, COX 2. When a small molecule inhibitor of COX 2 enzyme was added, reversion of the transformed phenotype occurred. The COX 2 gene has been found to be increased in pre-malignant adenomas in humans and overexpressed in human colon cancer. Inhibitors of COX 2 expression also arrests the growth of the tumor. One of the cell lines, x18 (SEQ ID NO:94), has disrupted a gene that is now represented in the EST (dbest) database, but the gene is not known (not present in GenBank).

Each of the genes from which the provided nucleotide sequences is isolated (and all clones designated with an "x") represents a tumor suppressor gene. The mechanism by which the disrupted genes may suppress a transformed phenotype is at present unknown. However, each one represents a tumor suppressor gene that is potentially unique, as none of the genomic sequences correspond to a known gene. The capacity to select quickly tumor suppressor genes may provide unique targets in the process of treating or preventing (potential for diagnostic testing) cancer.

Isolation of Entire Genomic Genes

An isolated nucleic acid of this invention (whose sequence is set forth in any of SEQ ID NO:1 through SEQ ID NO:127), or a smaller fragment thereof, is labeled by a detectable label and utilized as a probe to screen a rat genomic library (lambda phage or yeast artificial chromosome vector library) under high stringency conditions, i.e., high salt and high temperatures to create hybridization and wash temperature 5–20° C. Clones are isolated and sequenced by standard Sanger dideoxynucleotide sequencing methods. Once the entire sequence of the new clone is determined, it is aligned with the probe sequence and its orientation relative to the probe sequence determined. A second and third probe is designed using sequences from either end of the combined genomic sequence, respectively. These probes are used to screen the library, isolate new clones, which are sequenced. These sequences are aligned with the previously obtained sequences and new probes designed corresponding to sequences at either end and the entire process repeated until the entire gene is isolated and mapped. When one end of the sequence cannot isolate any new clone, a new library can be screened. The complete sequence includes regulatory regions at the 5' end and a polyadenylation signal at the 3' end.

Isolation of cDNAs

An isolated nucleic acid (whose sequence is set forth in any of SEQ ID NO:1 through SEQ ID NO:127), or a smaller fragment thereof, or additional fragments obtained from the genomic library, that contain open reading frames, is labeled by a detectable label and utilized as a probe to screen a portions of the present fragments, to screen a cDNA library. A rat cDNA library obtains rat cDNA; a human cDNA library obtains a human cDNA. Repeated screens can be utilized as described above to obtain the complete coding sequence of the gene from several clones if necessary. The isolates can then be sequenced to determine the nucleotide sequence by standard means such as dideoxynucleotide sequencing methods.

Serum Survival Factor Isolation and Characterization

The lack of tolerance to serum starvation is due to the acquired dependence of the persistently infected cells for a serum factor (survival factor) that is present in serum. The serum survival factor for persistently infected cells has a molecular weight between 50 and 100 kD and resists inactivation in low pH (pH2) and chloroform extraction. It is inactivated by boiling for 5 minutes [once fractionated from whole serum (50 to 100 kD fraction)], and in low ionic strength solution [10 to 50 mM].

The factor was isolated from serum by size fraction using centriprep molecular cut-off filters with excluding sizes of 30 and 100 kd (Millipore and Amnicon), and dialysis tubing with a molecular exclusion of 50 kd. Polyacrylamide gel electrophoresis and silver staining was used to determine that all of the resulting material was between 50 and 100 kd, confirming the validity of the initial isolation. Further purification was performed on using ion exchange chromatography, and heparin sulfate adsorption columns, followed by HPLC. Activity was determined following adjusting the pH of the serum fraction (30 to 100 kd fraction) to different pH conditions using HCl and readjusting the pH to pH 7.4 prior to assessment of biologic activity. Low ionic strength sensitivity was determined by dialyzing the fraction containing activity into low ionic strength solution for various lengths of time and readjusting ionic strength to physiologic conditions prior to determining biologic activity by dialyzing the fraction against the media. The biologic activity was maintained in the aqueous solution following chloroform extraction, indicating the factor is not a lipid. The biologic activity was lost after the 30 to 100 kd fraction was placed in a 100° C. water bath for 5 minutes.

Isolated Nucleic Acids

Tagged genomic DNAS isolated were sequenced by standard methods using Sanger dideoxynucleotide sequencing. The sequences were run through computer databanks in a homology search. These genes can be therapy targets particularly because disruption of one or both alleles results in a viable cell.

What is claimed:

1. A method of identifying a cellular gene necessary for viral growth in a cell and nonessential for cellular survival, comprising
   (a) transferring into a cell culture a vector encoding a selective marker gene lacking a functional promoter,
   (b) selecting cells expressing the marker gene,
   (c) infecting the cell culture with the virus, and
   (d) isolating from the surviving cells a cellular gene within which the marker gene is inserted, thereby identifying a gene necessary for viral growth in a cell and nonessential for cellular survival.

2. A method of screening a compound for antiviral activity, comprising a) administering the compound to a cell containing a cellular gene that is necessary for viral growth in the cell, but not necessary for survival of the cell; b) detecting the level and/or activity of the gene product produced by the cellular gene, a decrease or elimination of the gene product and/or gene product activity indicating a compound with antiviral activity, wherein the cellular gene can be identified by the method comprising:
   a) transferring into a cell culture a vector encoding a selective marker gene lacking a functional promoter;
   b) selecting cells expressing the marker gene;
   c) infecting the cell culture with the virus, and
   d) isolating from the surviving cells a cellular gene within which the marker gene is inserted.

3. A method of screening a compound for antiviral activity, comprising administering the compound to a cell containing a cellular gene comprising the nucleic acid set forth in SEQ ID NO:75 or a cellular gene comprising a nucleic acid that hybridizes to the nucleic acid set forth as SEQ ID NO: 75 under stringent hybridization conditions of hybridization at 68° C. in 6×SSC or 6×SSPE followed by washing at 68° C., and detecting the level and/or activity of the gene product produced, a decrease or elimination of the gene product and/or gene product activity indicating a compound with antiviral activity, wherein the cellular gene functionally encodes a gene product necessary for viral growth in the cell, but not necessary for survival of the cell.

4. A method of screening a compound for antiviral activity comprising:
   a) administering the compound to a cell containing a cellular gene comprising the nucleic acid set forth in SEQ ID NO:75 or a cellular gene comprising a nucleic acid that hybridizes to the nucleic acid set forth as SEQ ID NO: 75 under stringent hybridization conditions of hybridization at 68° C. in 6×SSC or 6×SSPE followed by washing at 68° C., and functionally encoding a gene product necessary viral growth in the cell but not necessary for survival of the cell;
   b) contacting the cell with a virus;
   c) detecting the level of viral infection;
   d) associating the level of viral infection with the level of the gene product and/or gene product activity of the cellular gene of a), a decrease or elimination of viral infection associated with a decrease or elimination of the gene product and/or gene product activity of a cellular gene of a) indicating a compound with antiviral activity.

5. A method of screening a compound for antiviral activity, comprising administering the compound to a cell containing a cellular gene comprising the nucleic acid set forth in SEQ ID NO:75, or a cellular gene comprising a nucleic acid that hybridizes to the nucleic acid set forth as SEQ ID NO: 75 under stringent hybridization conditions of hybridization at 68° C. in 6×SSC or 6×SSPE followed by washing at 68° C., wherein the cellular gene can be identified by the method comprising:
  a) transferring into a cell culture a vector encoding a selective marker gene lacking a functional promoter;
  b) selecting cells expressing the marker gene;
  c) infecting the cell culture with the virus, and
  d) isolating from the surviving cells a cellular gene within which the marker gene is inserted,
and functionally encoding a gene product necessary for viral growth in the cell but not necessary for survival of the cell and detecting the level and/or activity of the gene product produced, a decrease or elimination of the gene product and/or gene product activity indicating a compound with antiviral activity.

6. A method of making an antiviral compound, comprising:
  a) synthesizing a compound;
  b) administering the compound to a cell containing a cellular gene that is necessary for viral growth in the cell, but not necessary for survival of the cell, wherein the cellular gene is identified by the method comprising:
    (i) transferring into a cell culture a vector encoding a selective marker gene lacking a functional promoter;
    (ii) selecting cells expressing the marker gene;
    (iii) infecting the cell culture with the virus, and
    (iv) isolating from the surviving cells a cellular gene within which the marker gene is inserted; and
  c) detecting the level and/or activity of the gene product produced by the cellular gene, a decrease or elimination of the gene product and/or gene product activity indicating that an antiviral compound was made.

7. The method of claim 6, wherein the cell contains a cellular gene comprising the nucleic acid set forth in SEQ ID NO:75 or a cellular gene comprising a nucleic acid that hybridizes to the nucleic acid set forth as SEQ ID NO: 75 under stringent hybridization conditions of hybridization at 68° C. in 6×SSC or 6×SSPE followed by washing at 68° C.

8. A method of making an antiviral compound, comprising:
  a) synthesizing a compound;
  b) administering the compound to a cell containing a cellular gene that is necessary for viral growth in the cell, but not necessary for survival of the cell, wherein the cellular gene is identified by the method comprising:
    (i) transferring into a cell culture a vector encoding a selective marker gene lacking a functional promoter;
    (ii) selecting cells expressing the marker gene;
    (iii) infecting the cell culture with the virus, and
    (iv) isolating from the surviving cells a cellular gene within which the marker gene is inserted,
  c) contacting the cell with a virus;
  d) detecting the level of viral infection; and
  e) associating the level of viral infection with the level of the gene product and/or gene product activity of the cellular gene of b), a decrease or elimination of viral infection associated with a decrease or elimination of the gene product and/or gene product activity of a cellular gene of b) indicating a compound with antiviral activity was made.

9. The method of claim 8, wherein the cell contains a cellular gene comprising the nucleic acid set forth in SEQ ID NO:75 or a cellular gene comprising a nucleic acid that hybridizes to the nucleic acid set forth as SEQ ID NO: 75 under stringent hybridization conditions of hybridization at 68° C. in 6×SSC or 6×SSPE followed by washing at 68° C.

10. A method of making an antiviral composition, comprising:
  a) administering a compound to a cell containing a cellular gene that is necessary for viral growth in the cell, but not necessary for survival of the cell, wherein the cellular gene is identified by the method comprising:
    (i) transferring into a cell culture a vector encoding a selective marker gene lacking a functional promoter;
    (ii) selecting cells expressing the marker gene;
    (iii) infecting the cell culture with the virus, and
    (iv) isolating from the surviving cells a cellular gene within which the marker gene is inserted;
  b) detecting the level and/or activity of the gene product produced by the cellular gene, a decrease or elimination of the gene product and/or gene product activity indicating that the compound is an antiviral compound; and
  c) placing the antiviral compound in a pharmaceutically acceptable carrier.

11. The method of claim 10, wherein the cell contains a cellular gene comprising the nucleic acid set forth in SEQ ID NO:75 or a cellular gene comprising a nucleic acid that hybridizes to the nucleic acid set forth as SEQ ID NO: 75 under stringent hybridization conditions of hybridization at 68° C. in 6×SSC or 6×SSPE followed by washing at 68° C.

12. A method of making an antiviral composition, comprising:
  a) administering a compound to a cell containing a cellular gene that is necessary for viral growth in the cell, but not necessary for survival of the cell, wherein the cellular gene is identified by the method comprising:
    (i) transferring into a cell culture a vector encoding a selective marker gene lacking a functional promoter;
    (ii) selecting cells expressing the marker gene;
    (iii) infecting the cell culture with the virus, and isolating from the surviving cells a cellular gene within which the marker gene is inserted;
  b) contacting the cell with a virus;
  c) detecting the level of viral infection;
  d) associating the level of viral infection with the level of the gene product and/or gene product activity of the cellular gene of b), a decrease or elimination of viral infection associated with a decrease or elimination of the gene product and/or gene product activity of a cellular gene of b) indicating that the compound is an antiviral compound; and
  e) placing the antiviral compound in a pharmaceutical composition.

13. The method of claim 12, wherein the cell contains a cellular gene comprising the nucleic acid set forth in SEQ ID NO:75 or a cellular gene comprising a nucleic acid that hybridizes to the nucleic acid set forth as SEQ ID NO: 75 under stringent hybridization conditions of hybridization at 68° C. in 6×SSC or 6×SSPE followed by washing at 68° C.

* * * * *